United States Patent
Gras-Masse et al.

(10) Patent No.: US 7,476,386 B1
(45) Date of Patent: Jan. 13, 2009

(54) MIXED LIPOPEPTIDE MICELLES FOR INDUCING AN IMMUNE RESPONSE

(75) Inventors: Hélène Gras-Masse, Merignies (FR); Marc Bossus, Lille (FR); Guy Lippens, Santes (FR); Jean-Michel Wieruszeski, Noyelles sous Lens (FR); André Tartar, Artois (FR); Jean-Gérard Guillet, Vanves (FR); Isabelle Bourgault-Villada, Paris (FR)

(73) Assignees: Institut National de la Sante et de la Recherche Medicale (Inserm), Paris cedex (FR); Centre National de la Recherche Scientifique, Paris cedex (FR); Institute Pasteur de Lille, Lille cedex (FR)

( * ) Notice: Subject to any disclaimer, the term of this patent is extended or adjusted under 35 U.S.C. 154(b) by 1015 days.

(21) Appl. No.: 09/555,780

(22) PCT Filed: Dec. 2, 1998

(86) PCT No.: PCT/FR98/02605

§ 371 (c)(1),
(2), (4) Date: Nov. 17, 2000

(87) PCT Pub. No.: WO99/27954

PCT Pub. Date: Jun. 10, 1999

(30) Foreign Application Priority Data

Dec. 3, 1997 (FR) ................... 97 15246

(51) Int. Cl.
- *A61K 39/39* (2006.01)
- *A61K 39/21* (2006.01)
- *A61K 39/29* (2006.01)
- *A61K 39/12* (2006.01)
- *A61K 39/015* (2006.01)
- *A61K 39/00* (2006.01)

(52) U.S. Cl. ............. 424/184.1; 424/188.1; 424/193.1; 424/196.11; 424/277.1; 424/208.1; 424/227.1; 424/204.1; 424/272.1; 424/185.1; 424/278.1

(58) Field of Classification Search ............ 424/9.2, 424/9.3, 184.1, 188.1, 193.1, 278, 420; 435/5, 435/7.24; 502/527.24; 530/300; 536/71
See application file for complete search history.

(56) References Cited

FOREIGN PATENT DOCUMENTS

| EP | 0 491 628 A2 | 6/1992 |
|---|---|---|
| WO | WO 96/17863 | 6/1996 |
| WO | WO 96/40213 | 12/1996 |

OTHER PUBLICATIONS

Desrosiers. Nature Medicine. Mar. 2004; 10 (3): 221-223.*
BenMohamed, et al., "Lipopeptide immunization without adjuvant induces potent and long-lasting B, T helper, and cytotoxic T lymphocyte responses against a malaria liver stage antigen in mice and chimpanzees", *Eur. J. Immunol.* vol. 27, pp. 1242-1253 (1997).
Deprez, et al., "Comparative efficiency of simple lipopeptide constructs for in vivo induction of virus-specific CTL", *Vaccine*, vol. 14, No. 5, pp. 375-382 (1996).
Livingston, et al., "The Hepatitis B Virus-Specific CTL Responses Induced in Humans by Lipopeptide Vaccination are Comparable to Those Elicited by Acute Viral Infection", *The Journal of Immunology*, vol. 159, pp. 1383-1392, (1997).
Vitiello, et al., "Development of a Lipopeptide-based Therapeutic Vaccine to Treat Chronic HBV Infection", *J. Clin. Invest.*, vol. 95, pp. 341-349 (1995).
Gavioli, et al., "Multiple HLA A11-Restricted Cytotoxic T-Lymphocyte Epitopes of Different Immunogenicites in the Epstein-Barr Virus-Encoded Nuclear Antigen 4", *Journal of Virology*, vol. 67, No. 3, pp. 1572-1578 (1993).
Wain-Hobson, et al., "Nucleotide Sequence of the AIDS Virus, LAV", *Cell*, vol. 40, pp. 9-17 (1985).
Zhang, et al., "An HLA-A11-specific motif in nonamer peptides derived from viral and cellular proteins", *Proc. Natl. Acad. Sci. USA*, vol. 90, pp. 2217-2221 (1993).

* cited by examiner

*Primary Examiner*—Mary E Mosher
(74) *Attorney, Agent, or Firm*—Hoffmann & Baron, LLP; Irving N. Feit

(57) ABSTRACT

The invention concerns mixed micelles or micro-aggregates for inducing an immune response containing at least a first lipopeptide comprising a CTL epitope and at least a first lipid motif; and a second lipopeptide comprising at least an auxiliary T epitope and at least a lipid motif, whereof the type can be different from the first lipopeptide motif. Said micelles can be used as medicines and vaccines.

20 Claims, 11 Drawing Sheets

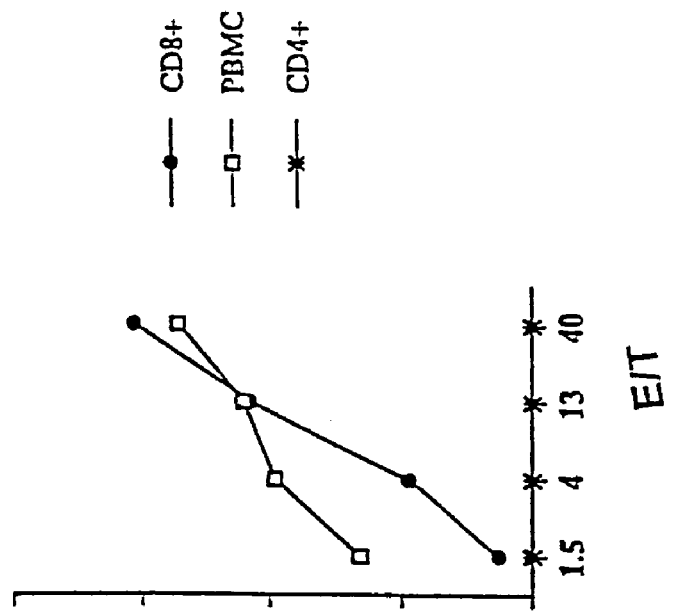
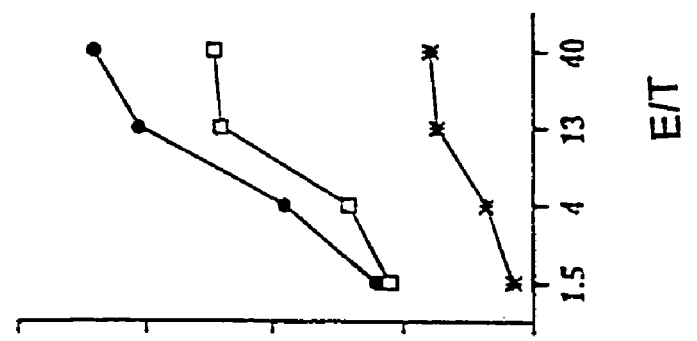
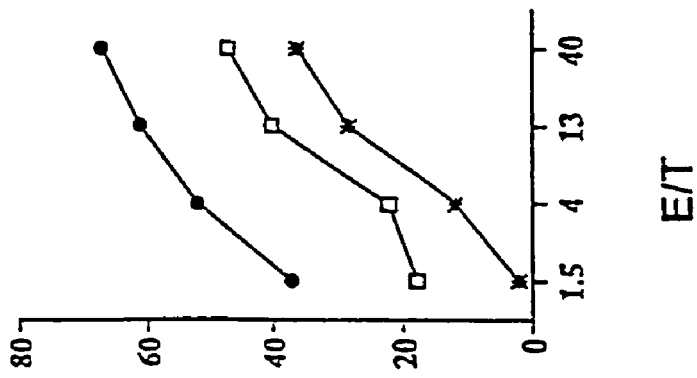

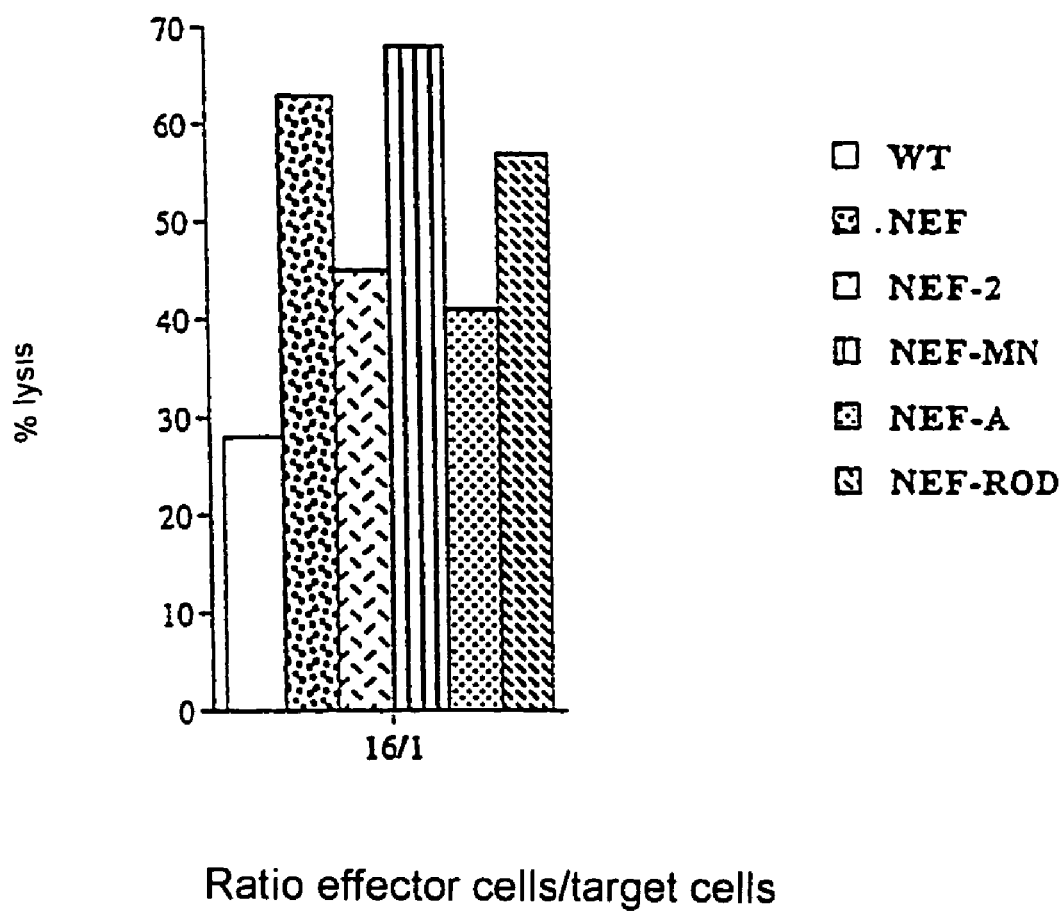

MIXED LIPOPEPTIDE MICELLES FOR INDUCING AN IMMUNE RESPONSE

BACKGROUND OF THE INVENTION

The present invention relates to mixed lipopeptide micelles for inducing an immune response.

A further object is the use of these micelles for therapeutic purposes.

There are two types of effector immune responses: the humoral response due to antibodies, and the cytotoxic response due to $CD8^+$ T lymphocytes.

An effective cytotoxic response requires the presentation of the antigens to the cytotoxic $CD8^+$ T lymphocytes (CTL), in combination with class I molecules of the Major Histocompatibility Complex (MHC), but also to helper $CD4^+$ T lymphocytes (HTL) in combination with class II MHC molecules.

The use of lipopeptides for inducing a cytotoxic response, in other words the in vivo generation of cytotoxic T lymphocytes, has already been described. In particular, application FR-90 15 870 published under the n° 2 670 787 (Institut Pasteur de Lille, Institut Pasteur, INSERM) discloses lipopeptides composed of a peptide portion comprising 10 to 40 amino acids and a lipid portion which may be derived from fatty acids or steroid groups.

These lipopeptides show a good aptitude for inducing a cytotoxic response. However it was advisable to make them able to induce a better quality response by addition of a helper T response whose importance for effective induction and maintenance of the cytotoxic response is known. It was also advisable to make them able to induce a response in as many individuals as possible.

BOURGAULT et al. (1994, J. Immunol., 2530-2537) induced a CTL and HTL response from a mixture of lipopeptides, in the form of an emulsion with an oily adjuvant.

Nevertheless, it was necessary to add incomplete Freund's adjuvant (IFA). The immunogenicity of the vaccine preparation used necessarily involved the functional co-presentation of the HTL and CTL units located in one or more lipopeptides in the mixture. However, the effectiveness of the co-presentation of the different units involved depended on the combination with the incomplete Freund's adjuvant within a very fine emulsion.

An article under the name of VITIELLO et al. (1995, J. Clin. Invest., 95, 341-349) raised the possibility of inducing a CTL response in a selected human population (HLA-A2) by using a lipopeptide containing a sequential combination of a CTL HLA-A2 antigenic determinant and a multivalent helper (HTL) antigenic determinant. It should be noted that this study was carried out on a genetically restricted population.

This article also reports an experiment during which two types of associations between the HTL antigenic determinant and the CTL antigenic determinant were compared: on the one hand, a covalent sequential combination within the same lipopeptide, and on the other an association by simple mixture of a lipopeptide containing the CTL unit with a peptide containing the HTL unit. The results of this study showed a very clear advantage of the covalent combination compared to the mixture, as performed by the authors, in other words by mixture of solutions containing DMSO and PBS buffer (the peptides or lipopeptides were kept in stock solutions at a concentration of 10-20 mg/ml and diluted with PBS just before use).

However, the combination within the same lipopeptide molecule of the cytotoxic and helper antigenic determinants, although able to induce an effective immune response, required the synthesis of long amino acid sequences presenting the multiple antigenic determinants able to combine with several HLA or superfamilies of class I and class II HLA. The covalent combination of all these units within a single molecule presented technical problems not easily overcome, both from the points of view of synthetic methods and analytical characterisation.

In any case, this article mentions the combination of a lipopeptide and a peptide, and not of two lipopeptides. For this reason no mixed micelle formation could take place.

Another article, published by DON DIAMOND et al. (1997, Blood, 90, n° 5), mentions the immunogenicity of a mixture between a peptide carrying a minimal CTL antigenic determinant (pp 65, sequence 495-503 of the cytomegalovirus matrix protein) and a dipalmitoyl peptide containing an HTL antigenic determinant. The mixture was achieved by mixing solutions in dilute acetic acid or in DMSO, using an ultrasonic treatment for 15 to 30 seconds.

This article thus does not describe a mixture of lipopeptides independently containing a CTL antigenic determinant and an HTL antigenic determinant, but the mixture of a lipopeptide containing an HTL antigenic determinant and a nonapeptide corresponding to a minimal CTL antigenic determinant. In addition, there is no mention of the formation of mixed micelles or of micro-aggregates. In this particular case, however, the possibility of direct combination between the nonapeptide and the class I MHC expressed at the surface of the cells could explain the success of the approach followed. The immunogenicity of the preparation indicates that there was effectively co-presentation of the HTL and CTL antigenic determinants by the same antigen-presenting cell; however, the minimal nonapeptide used has the capacity to link directly with the class I MHC at the surface of the antigen-presenting cell, without its presentation by the cell being necessary.

The authors conclude by recognising that there are still several obstacles to long-term immunity, which confirms the experimental character of this study.

The difficulty of obtaining an immune response depending on a double presentation of the peptides separately presenting the HTL and CTL antigenic determinants is now explained by a publication by STUHLER (1997, Proc. Natl. Acad. Sci. USA, 94, 622-627). To be able to observe the induction of a CTL response, it is absolutely necessary that the HTL and CTL antigenic determinants are present on the surface of the same antigen-presenting cell (APC) to be able to be recognised at the same time by the helper T cells recognising the HTL antigenic determinant and the cytotoxic T cells recognising the CTL antigenic determinant.

It follows from the above that compositions containing within the same micelles, or the same micro-aggregates, on the one hand lipopeptides presenting a CTL antigenic determinant and on the other lipopeptides containing an auxiliary T antigenic determinant, i.e. mixed micelles or micro-aggregates, have never, to the knowledge of the applicant, been described.

However, as described above, it is absolutely necessary that the two antigenic determinants, cytotoxic and helper T, are present on the surface of the same antigen-presenting cell.

In addition to the necessity of a co-presentation of the two antigenic determinants on the surface of the same cell, it is also essential to solubilize the lipopeptides, so as to allow their administration to patients, and their sterilisation by filtration.

SUMMARY OF THE INVENTION

The applicant has thus endeavoured to find a solution to these different problems.

He has shown that, in order to obtain micelles individually formed from all the peptides present in the mixture, whether containing HTL or CTL antigenic determinants, it was necessary to combine the different lipopeptides after having previously dispersed them at the molecular level in a suitable solvent.

The object of the present invention is thus micelles or micro-aggregates for inducing an immune response containing at least:
  a first lipopeptide comprising at least one CTL antigenic determinant, or cytotoxic antigenic determinant, and at least one lipid unit, and
  a second lipopeptide comprising at least one helper antigenic determinant and at least one lipid unit, which may be of a different type from the first lipopeptide unit.

BRIEF DESCRIPTION OF THE DRAWINGS

FIGS. 12A, 12B and 12C respectively show the anti-N1, anti-G2 and anti-E cytotoxic activities of PBMC, $CD8^+$ and $CD4^+$ cells of the individual V4.1.

FIG. 13 shows the cytolytic activity of PBMC of individual V4.5 collected twenty weeks after the beginning of immunization, stimulated in vitro with peptide N2 then tested for their CTL activity against wild vaccine (WT), or this same virus expressing a recombinant NEF protein (NEF, NEF-2, NEF-MN, NEF-A, NEF-ROD).

DETAILED DESCRIPTION OF THE INVENTION

Figure 1:
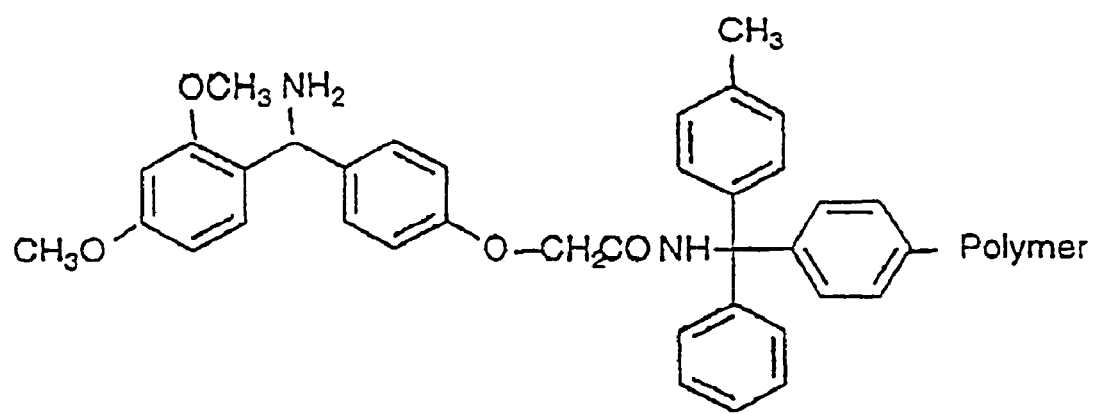
FIG. 1 represents the chemical structure of the resin of type KNORR-MBHA.

In the scope of the present invention, the expression "immune response" means the whole of the induced immune response, which includes the cytotoxic response and the humoral response.

The micelles according to the present invention are not limited to two lipopeptides, but may contain other lipopeptides independently presenting HTL or CTL antigenic determinants.

To understand the present invention, helper T antigenic determinant should be understood as meaning an amino acid sequence able to bind with at least one class II HLA receptor, and able to be recognised by helper T lymphocytes.

CTL antigenic determinant should be understood as meaning an amino acid sequence able to bind with at least one class I HLA receptor and able to be recognised by cytotoxic T lymphocytes.

The helper T antigenic determinants able to bind with several different class II HLA receptors are called multivalent helper antigenic determinants (multivalent HTL).

In addition, by micelles or micro-aggregates should be understood aggregates of lipopeptides with a size making them able to be assimilated simultaneously by any antigen-presenting cell (APC) and preferably with a size less than about 1 µm.

The mixed micelles according to the invention, in other words comprising lipopeptides containing cytotoxic antigenic determinants and lipopeptides containing helper T antigenic determinants, have the advantage of combining, within the same microvolume which can be assimilated by a single APC, a wide variety of CTL and HTL antigenic determinants, without their covalent combination being necessary, while respecting the required criterion of chemical definition. Micelles which each contain a single type of lipopeptide, containing a CTL antigenic determinant or an HTL antigenic determinant, do not result in an effective co-presentation corresponding to the induction of a strong effector response.

In addition, obtaining a CTL response by the use of mixed micro-aggregates or micelles avoids the use of emulsions with oily adjuvants, such as incomplete Freund's adjuvant, whose use is not approved in human therapeutics. The micelles and micro-aggregates according to the present invention are however compatible with the use of emulsions with clinically acceptable oily vehicles.

A further advantage of the mixed micro-aggregates or micelles according to the present invention, each containing at least two types of lipopeptides, is that the solubilization of lipopeptides with a low solubility in water or in clinically acceptable solvents, or insoluble lipopeptides, may be improved by their combination with other lipopeptide(s) with better solubility.

The micelles according to the present invention also show the advantage, compared to lipopeptides in which the HTL and CTL units are combined covalently and whose size is limited, such as those described by VITIELLO et al. (1995, cited above), of allowing the combination of a wide variety of units, and thus can be used for the vaccination of human or animal populations not selected on the basis of genetic restriction.

The micelles according to the present invention may contain a lipopeptide with at least a CTL antigenic determinant and another lipopeptide containing at least a helper antigenic determinant. However, such micelles may also contain several different lipopeptides containing different cytotoxic antigenic determinants and different lipopeptides with different helper antigenic determinants.

The lipid units of the lipopeptides may independently be one or more $C_4$-$C_{18}$ units, and in particular one or more $C_4$-$C_{18}$ chains derived from fatty acids, or fatty alcohols, optionally branched and unsaturated or derived from a steroid.

They may contain one or two $C_4$ to $C_{18}$ lipid chains linked by a covalent bond to one or two amino acids of the peptide part. They may also be composed of two palmitic acid chains linked to the alpha and epsilon $NH_2$ groups of a lysine.

These lipid units may also be composed of, or contain, a residue of palmitic acid, 2-aminohexadecanoic acid, oleic acid, linoleic acid, linolenic acid, pimelautide, trimexautide, or a derivative of cholesterol, or any other natural lipid component of the cell membranes.

The lipopeptides constituting the mixed micelles or micro-aggregates are advantageously water-soluble in a proportion of at least 30% (by weight). These water-soluble lipopeptides have cationic surface-active properties, suitable for providing a solubilizing effect on other lipopeptides in weak acid medium.

The non-lipid part contains between 10 and 100, and preferably between 10 and 50 amino acids. The number of amino acids depends on the number of antigenic determinants constituting the non-lipid part of the lipopeptide and on their sizes, on the nature of the lipid part, and the proportions of the lipid and non-lipid parts.

The HTL and CTL antigenic determinants used are advantageously antigenic determinants able to bind with several different HLA, otherwise called multivalent or promiscuous antigenic determinants.

The HTL antigenic determinant used is preferably composed of the multivalent peptide 830-843 of the tetanus toxin. QYIKANSKFIGITE (SEQ ID NO:1)

The glutamine (Q) of this sequence may optionally be acetylated.

Other multivalent HTL antigenic determinants may be the multivalent antigenic determinant of hemagglutinin (PREVOST-BLONDEL et al., 1995, J. Virol., vol. 62, n° 12, pages 8046-8055) or the PADRE antigenic determinant (ALEXANDER et al., 1994, Immunity, 1, 751).

The CTL antigenic determinant may be any antigenic determinant able to activate cytotoxic CD8$^+$ T lymphocytes.

It is preferably a CTL antigenic determinant of a protein presented by a tumour cell and in particular by a melanoma, a protein from HIV, from hepatitis B virus (HBV) or from papillomavirus, or protein p53.

It may in particular be one of the following antigenic determinants:
   antigenic determinants of protein BCR-ABL, resulting from the BCR-Abelson translocation (chronic myeloid leukemia) such as those listed in table 1.
   antigenic determinants of protein p53, such as those listed in table 2.
   The antigenic determinants of protein p53 may in addition be comprised in the sequences 25-35, 63-73, 129-156, 149-156, 187-205, 187-234, 226-264, or 249-264 of this protein.
   antigenic determinants of proteins $E_6$ or $E_7$ of human papillomavirus (HPV), such as those listed in table 3.
   antigenic determinants of proteins of the HIV-1 virus such as those listed in table 4.
   antigenic determinants of melanoma or other tumours, such as those listed in tables 5, 6 and 7 and in particular antigenic determinants of the melan-A/mart-1 antigen of melanoma.

Other multivalent CTL antigenic determinants with a capacity to bind to class I HLA ma be those included in the peptide 43-57 of HPV (GQAEPDRAHNIVTF (SEQ ID NO:284)) which contains HLA A2, A24, B7 and B18 antigenic determinants.

The CTL antigenic determinants may also be those of parasite antigens, and in particular of *Plasmodium falciparum*.

The mixed lipopeptide micro-aggregates or micelles according to the present invention may be freeze-dried, then taken up into any clinically acceptable buffer to be administered to the patients to be treated, and in particular to patients to be vaccinated.

They may be administered by any administration route used in therapeutics and, as non-limiting examples, by parenteral, percutaneous, oral, or sublingual routes or by intra-pulmonary nebulizer.

A further object of the present invention is thus the use of these lipopeptides for the production of a drug or vaccine for inducing a specific immune response, and in particular, for inducing an immune response against cancers such as melanoma, HIV and HBV viruses, papillomavirus, p53 or malaria.

Another object of the present invention is a pharmaceutical composition characterized in that it contains a pharmacologically active quantity of one or more of the lipopeptides described above, in addition to pharmaceutically compatible vehicles.

The present invention also relates to a method of inducing an immune response against an antigen comprising the administration of micelles or micro-aggregates, such as those described above, to an individual for which such a response is sought.

An additional object is a method of immunization against a pathogenic agent comprising the administration of micelles or micro-aggregates such as those described above to an individual for whom such an immunization is sought. Such pathogenic agents, and antigens, may be those listed above.

The lipopeptides forming the micelles according to the present invention may be produced by any suitable method known to a person skilled in the art. They may in particular be obtained by the Boc-benzyl or Fmoc-tert-butyl methods, in particular as disclosed in the application FR-90 15 870, which patent application is incorporated herein by reference.

The introduction of the lipid chain may be achieved in the solid phase, after selective deprotection of the functional group or groups concerned, as described in the article by DEPREZ et al., (1996, Vaccine, volume 14, n° 5, 375-382). The lipid chain may be introduced onto the $\epsilon$-NH$_2$ function of a lysine protected on the $\alpha$-NH$_2$ function by an F-moc group. The Fmoc-lys (Palm) obtained may then be used in solid-phase synthesis to produce the lipopeptide.

The micelles and micro-aggregates according to the present invention may be obtained by dispersing each lipopeptide in a concentrated acetic acid solution at about 80% concentration, then mixing the solutions thus obtained.

The quality of dissolution, i.e. the effective dispersion at the molecular level of each lipopeptide before the preparation of the mixture, is confirmed by the two-dimensional nuclear magnetic resonance method (2DNMR). The resolution of the signal obtained during homonuclear experiments in two dimensions in a 600 MHz field confirms the complete dispersion, at the molecular level, of the lipopeptides in solution. The clarity of the mixture is not a sufficient criterion: in particular, the taking up of the lipopeptides by DMSO or a DMSO/water mixture does not lead, in most cases, to a sufficient dispersion state, which explains the ineffectiveness of the mixture studied by VITIELLO et al. (1995, cited above). Dissolution by acetic acid/water mixtures which are more dilute in acetic acid also does not lead in all cases to the preparation of a mixture of mixed micro-aggregates or micelles containing a statistical proportion of each constituent of the mixture at the microvolume level. In these two cases, even in the presence of an apparently clear mixture, the sterilizing filtration over a 0.22 μm membrane is either impossible, or irregular, with filtration yields which differ according to the constituents, which indicates that at the scale of a particle of this size, the representation of each constituent of the mixture has not been achieved. This micro-heterogeneity compromises the immunogenicity of the mixture, since it comprises the simultaneous capture and presentation of all constituents by a single antigen-presenting cell (APC), in the case of CTL and HTL antigenic determinants present on separate lipopeptides.

The present invention is illustrated, without in any way being limited, by the following examples.

EXAMPLE 1

Preparation of Micelles or Micro-Aggregates According to the Invention

1—Description of Lipopeptides Used in the Mixture

| Name | Formula | Molecular Weight | SEQ ID NO: |
|---|---|---|---|
| NEF 66 | VGFPVTPQVPLRPMTYKAAVDLSHFLK-EKGGLK(Pam)-NH$_2$ | 3862.77 | 2 |
| NEF 117 | TQGYFPDWQNYTPGPGVRYPLTFGWC-YKLVPK(Pam)-NH$_2$ | 4017.754 | 3 |
| NEF 182 | EWRFDSRLAFHHVARELHPEYFKNK(Pam)-NH$_2$ | 3451.04 | 4 |
| GAG 183 | DLNTMLNTVGGHQAAMQMLKETINEE-AAEWDRK(Pam)-NH$_2$ | 3983.65 | 5 |
| GAG 253 | NPPIPVGEIYKRWIILGLNKIVRMYSPTS-ILDK(Pam)-NH$_2$ | 4063.05 | 6 |
| ENV | TRPNNNTRKSIHIGPGRAFYATGEIIGDI-RQAHK(Pam)-NH$_2$ | 4027.69 | 7 |

CTL antigenic determinants represented:

| | | |
|---|---|---|
| RPNNNTRKSI | SEQ ID NO. 8 | HLA-B27 |
| PPIPVGEIY | SEQ ID NO. 9 | HLA-B35 |
| KRWIILGLNK | SEQ ID NO. 10 | HLA-B27 |
| LGLNKIVRMY | SEQ ID NO. 11 | HLA-B62 |
| QVPLRPMTYK | SEQ ID NO. 12, 168, 174, 215 | HLA-A-3, A11, B27.2 |
| VPLRPMTY | SEQ ID NO. 13 | HLA-B35 |
| AVDLSHFL | SEQ ID NO. 14 | HLA-B62 |
| AVDLSHFLK | SEQ ID NO. 15, 175 | HLA-A11 |
| TQGYFPDWQNY | SEQ ID NO. 16 | HLA-B62 |
| YFPDWQNYT | SEQ ID NO. 17 | HLA-B17, B35 |
| TPGPGVRYPL | SEQ ID NO. 18, 193 | HLA-B7 |
| RYPLTFGW | SEQ ID NO. 19 | HLA-B27.2 |
| YPLTFGWC | SEQ ID NO. 20 | HLA-B18 |
| AFHHVAREL | SEQ ID NO. 21 | HLA-B52 |
| FLKEKGGL | SEQ ID NO. 22, 200 | HLA-B8 |

This set of antigenic determinants shown above should lead to the induction of CTL responses in a large proportion of the human population, on the condition of being able to benefit from the helper effect of HTL antigenic determinants which, although not defined, are very probably present for simple statistical reasons in any one of the lipopeptides on condition however of bringing together all the antigenic determinants, and thus all the peptide constituents of the mixture, in each micro-unit of volume.

2—Synthesis

The solid phase approach was selected, using the Fmoc strategy for protecting the α-amine function, and t-Bu for protecting the side chains. The protocol used was a standard protocol based on the synthetic methods described by ATHERTON (Solid-phase synthesis, a practical approach, IRL Press, 1989) and FIELDS and NOBLE (Int. J. Pept. Prot. Res., 1990, 35, 161-214).

The Fmoc-Lys(Palm)-OH was coupled to a resin of KNORR-MBHA type (FIG. 1). After deprotection of the alpha-amine function, the first amino acid was coupled (for example Fmoc-Leu-OH in the case of NEF 66). The coupling agent was TBTU (3 eq) in the presence of DIPEA (4.5 eq), with verification of coupling by a calorimetric test. A systematic acetylation was performed after a negative reaction had been obtained with this test, to minimize the risk of obtaining peptides by deletion. This succession of operations was repeated until all the amino acids in the sequence had been added.

After the synthesis, and deprotection of the terminal Fmoc group, the peptides were deprotected and cleaved by a TFA/water/DTT mixture (NEF 66, ENV), TFA/water/DTT/Ac-Trp-OH (GAG 183, GAG 253, NEF 117) or TFA/water/EDT/Ac-Trp-OH (NEF 182).

The peptides were each purified on a Vydac C18 column which was exclusively used for this purpose, at ambient temperature, with a water-acetonitrile solvent system, in perchlorate or TFA buffer.

They were then converted into their acetate form by ion exchange on a Dowex SBR column, then freeze-dried in 40% acetic acid.

Each peptide was produced from a single batch of synthesis and purification. No recycling of purification fractions was performed.

3—Studies of the Solubility of the Lipopeptides:

3-1) Use of Pure Water:

The peptides NEF 66, NEF 117, NEF 182 and ENV could be dissolved in pure water, at concentrations of up to 5 mg/ml. Peptide NEF 117 however gave a slightly opalescent solution. Peptides GAG 182 and GAG 253 were not soluble under these conditions.

The mixture of lipopeptides was however soluble in pure water, indicating that the hydrophilic lipopeptides were having a solubilizing effect on the less soluble peptides.

3-1) Use of DMSO:

The dissolution of lipopeptides is often performed using aqueous solutions of DMSO (dimethyl sulfoxide). This very powerful organic solvent is in fact compatible, after dilution, with the majority of biological tests carried out on cells or animals, even humans. The use of DMSO proved effective for good solution of peptides GAG 182 and GAG 253; the solutions obtained could then be diluted with water to reach a final concentration of 1 mg/ml in 20% DMSO/water; in these conditions, most of the peptides gave a clear solution, except GAG 183 for which a suspension was obtained.

It is useful to emphasize that even in the case of the clear solutions, and despite the compatibility of DMSO with Durapore filters, the solutions of lipopeptides in DMSO could not be filtered over filters of porosity 0.22 μm, because they exerted a pressure incompatible with the mechanical resistance of the filters. This observation shows the formation of aggregates of size greater than 0.22 μm. In some cases, we found it impossible to filter over filters resistant to solvents, with porosity 1 μm, because of the formation of gels (this size of filter is in fact used to filter concentrated lipopeptide solutions before purification by RP-HPLC).

3-3) Use of 25% Concentrated Acetic Acid:

The inclusion of the necessary step of sterilizing filtration thus requires the use of an organic solvent more suitable for dissociating the aggregates, compatible after dilution with freeze-drying, and non-toxic at low doses. Acetic acid was tested.

A minimum quantity of this solvent was initially used, defined as the quantity giving clear solutions at concentrations of 5 mg/ml: for peptides GAG 183 and GAG 253, 25% acetic acid was used; for the other peptides, dissolution in pure water was performed.

The solutions were subjected to nuclear magnetic resonance analysis in a 600 MHz field. It was observed that, despite the apparent clarity of the lipopeptide solutions of this series, even the most hydrophilic lipopeptides formed aggregates of significant size which prevented this type of study, in the absence of resolved signals.

Dissolution under these conditions did not lead to statistical dispersion, at the molecular level, of each of the constituents, despite the apparent clarity of the solutions.

3-4) Use of 80% Concentrated Acetic Acid:

The use of 80% concentrated acetic acid was then tested. The peptides were dissolved at a concentration of 1 mM in 1 ml of 80% acetic acid (corresponding to: NEF 66: 3.86 mg/ml; NEF 117: 4.02 mg/ml; NEF 182: 3.45 mg/ml; GAG 183: 3.98 mg/ml; GAG 253: 4.063 mg/ml; ENV: 4.027 mg/ml).

Analysis of the Lipopeptides by Proton NMR at 600 MHz

The lipopeptide samples were prepared by dissolving the lipopeptides in a solution of acetic acid (CD3COOD, 99.5% D atoms, EURISO-TOP, France)/H2O; 80:20 (V:V). 4 µl of a 50 mM solution of TMSP [sodium 3-(trimethylsilyl)propanesulfonate] in D2O were added as chemical shift reference. The final concentration of each peptide was 1 mM in at least 2 ml of solvent, which were transferred into 8 mm diameter NMR tubes (WILMAD 513A-7PP, Interchim, France).

The proton NMR spectra were performed on a BRUKER DMX600 NMR spectrometer fitted with an 8 mm BBI probe with z gradient, at a sample temperature of 310° K.

NOESY (Nuclear-Overhauser effect spectroscopy) experiments in two homonuclear dimensions according to Kumar et al. (1980, Biochem. Biophys. Res. Comm., 95, 1-6) and TOCSY (Total Correlation Spectroscopy) according to Bax and Davis (1985, J. Magn. Reson., 65, 355-360) and Griesinger et al. (1988, J. A. C. S., 110, 7870-7872) were obtained with 2048×512 complex points and processed after multiplication in two dimensions by a sine wave displaced by Π/4 with 2048×1024 points, for a spectral window of 12 ppm. The mixture times were 300 ms for the NOESY and 160 ms for the TOCSY. During the TOCSY mixture time, a MLEV 16 was applied with a B1 field of 7.8 KHz. So as to be under the same temperature conditions, the spin-lock time of the TOCSY was applied without resonance (+ or −1 MHz) in the NOESY. The suppression of water was achieved by using a slight pre-saturation of this signal during the relaxation time and the mixture time of the NOESY.

The high-field NMR analysis of the solutions showed perfectly resolved signals, allowing the TOCSY-NOESY experiments, and the complete sequential attribution of each lipopeptide. This result indicates complete dispersion, at the molecular level, of the lipopeptides in 80% acetic acid.

Figure 2:
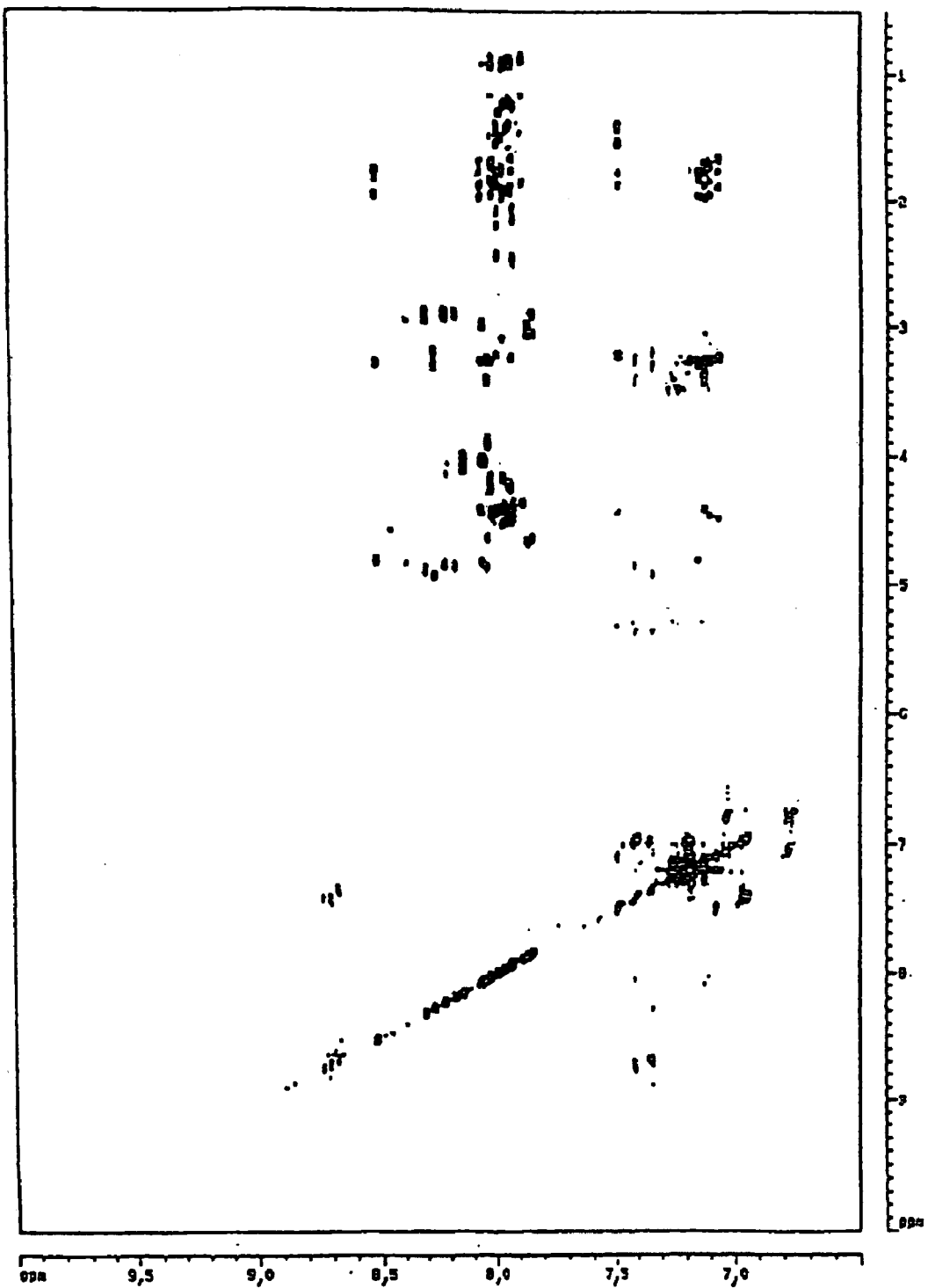
FIGS. 2 and 3 show the two-dimensional nuclear magnetic resonance (2DNMR) spectra of a single lipopeptide (lipopeptide ENV) and a mixture of lipopeptides respectively.
Figure 3:
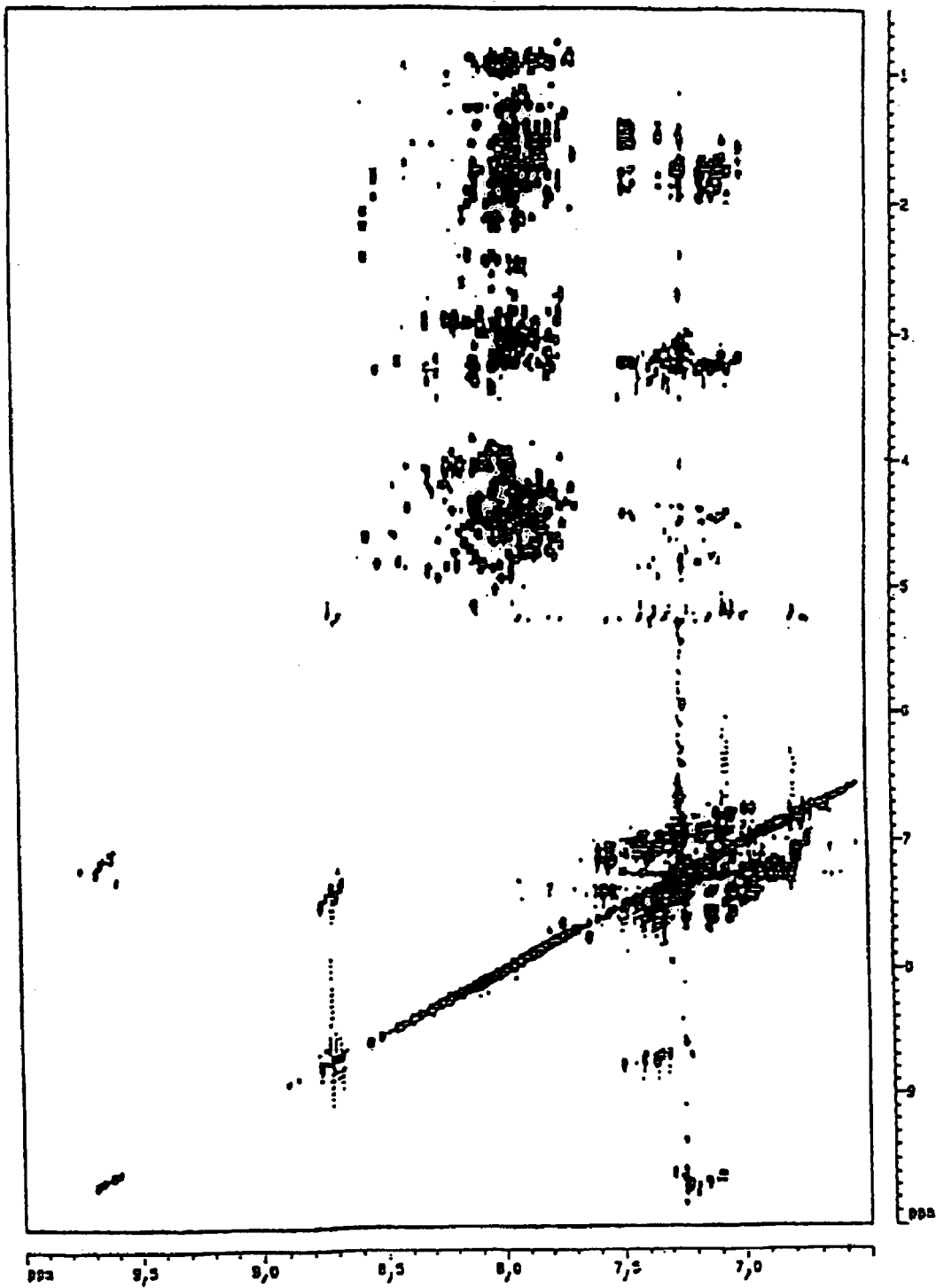

The 2D NMR spectrum of peptide ENV is shown on FIG. 2. The spectra of all the peptides could be obtained under the same conditions and interpreted. In order to verify if the intermixture of the solutions would change the dispersion of the lipopeptides, a 2D NMR spectrum of a virtual mixture was obtained by superimposing the 6 spectra obtained individually onto a single representation. It was compared with the 2D NMR spectrum actually obtained by mixing the solutions (FIG. 3). The resolution of the signals remained comparable, proving that none of the peptides had altered the solubility of the other constituents of the mixture. The sequence analysis required an accumulation of signals over 120 hours for each lipopeptide, during which period no significant alteration of the peptides was detected, either by NMR or by RP-HPLC. This observation thus allows the use of this solvent for the solubilization of the lipopeptides, their mixture, then filtration, even with a residence time of the order of 1 to 2 hours, conceivably necessary for the handling of relatively large volumes.

4—Studies of the Sterilization Filtration Step:

4-1 Isolated Lipopeptides:

Tests on the sterilizing filtration were performed on 5 mg/ml solutions of each lipopeptide in water for peptides NEF 66, NEF 117, NEF 182 and ENV and in 25% acetic acid for peptides GAG 183 and GAG 253. The filtration yields for 1 ml over Millipore Millex GV SLGV 0130S filters (0.22 µm), followed by freeze-drying, are shown in table 8 (to within the precision of the determination).

These results are in agreement with the solution studies performed by NMR, and give information on the size of the aggregates or micelles detected: some peptides form aggregates of size greater than 0.22 µm, and as a result lead to mixtures containing micro-heterogeneities and an improbable simultaneous capture at the scale of the antigen-presenting cell.

4-2) Preparation of Different Lipopeptide Mixtures:

a) Preparation of Batch CK2. Simple Mixture of Solutions, and Production of a Clear But Micro-Heterogeneous Solution:

For the dissolution of the lipopeptides and the preparation of the mixture, solutions of totally clear appearance were intermixed, so as to evaluate the possible contribution of the surface-active character of lipopeptides ENV, NEF 66, NEF 117 and NEF 182. The conditions are summarized in table 9.

The solutions obtained were subjected to ultrasonic action to encourage the dispersion of the aggregates, mixed to give a final volume of 5.5 ml, and the mixture was again subjected to ultrasonic action, then diluted with 9.5 ml of water to obtain a final concentration of about 8% in acetic acid (AcOH), compatible with a good quality freeze-drying. This solution, after a final period in the ultrasonic bath, was filtered over Millipore Millex GV SLGV 0130S filters (0.22 µm). The filtration yields for the peptides in the mixture were calculated for each lipopeptide, to give the results shown in the final column of table 9 (to within the precision of the determination).

The heterogeneity of the yields depending on the peptide showed the heterogeneity of the solution. Each peptide behaved as if it had been filtered individually: this behaviour was particularly evident for the peptide GAG 253, whose filtration yield from this solution in 8% acetic acid was lower than the yield observed when it was filtered alone from a solution of 25% acetic acid. This result confirms that, despite the apparent clarity of the mixture in dilute acetic solution, the mixture between the lipopeptides had not formed mixed micro-aggregates or micelles which contained in particular the more hydrophobic peptides. The exchanges of the lipopeptides between micelles occurs poorly under these conditions, and the surface-active function of lipopeptides ENV, NEF 66, NEF 117 and NEF 182 could not operate.

b) Preparation of Batch CK3: Preparation of Mixed Micelles or Micro-Aggregates not Including Micro-Heterogeneity In order to guarantee complete mixing of the different lipopeptides at the level of each micro-unit of volume, a different strategy was followed:

each lipopeptide was dissolved in 80% acetic acid so as to exploit the dissociating properties of this solvent.

in order to exploit the cationic surface-active properties expected of the peptides ENV, NEF 66, NEF 117 and NEF 182 in weak acid medium during the dilution step, the lipopeptides were dispersed in 80% acetic acid in the following order: 1: ENV, 2: NEF 66, 3: NEF 117, 4; NEF 182, ending with the dispersion of the two most hydrophobic lipopeptides in a solution now concentrated in dissociating agents: acetic acid and cationic detergents.

The fifth lipopeptide introduced was GAG 183 and the sixth GAG 253. An ultrasonic step was used at each stage to ensure effective dispersion of the aggregates.

The solutions were mixed, then filtered over Millex GV SLGV 0130S filters (0.22 µm). The filtration required a lower pressure than during the filtration of the 8% solution. The receiver vessels and the filter were then rinsed with water, in sufficient quantity to give a final acetic acid concentration of 8% (final volume 15 ml as before), so as to ensure the quality of the freeze-drying step. The filtration yields of the peptides in the mixture were calculated for each lipopeptide, to give the results listed in the final column of table 10 (to within the precision of the determination).

The homogeneity of the yields confirms the homogeneity of the solution resulting from the dispersion at the molecular level at the time of filtration in concentrated acetic acid. The subsequent dilution cannot result in a reorganization of each peptide into monovalent entities, by application of the laws of entropy. This method of preparation of the mixture thus gives mixed micelles which each necessarily contain a statistical representation of each lipopeptide. The surface-active properties of the lipopeptides can operate and guarantee the solubility in water of vaccine doses after freeze-drying as well as the stability of the solutions during the handling time.

c) Preparation of Batch CK9

The procedure used was the same as for the previous batch, apart from the quantities. The solution of the peptide (20 mg/ml in 80% acetic acid) was filtered in 4 portions, changing the filter before its saturation, using identical membranes (Durapore STERIVEX GV 0.22 µm sterile units (Millipore)), then made up with the water used for rinsing the filters and for dilution. The final volume was 1516 ml (including 154 ml of acetic acid: 10% in final solution). The portion volume was 1.3 ml per dose. The apportioned doses were freeze-dried, and analysed using a validated HPLC determination method. The filtration yield for each lipopeptide is given below in table 11, and takes into account the determination sensitivity of each lipopeptide.

During the preparation of this batch, we again observed good homogeneity of the filtration yields, confirming the formation of mixed micelles or micro-aggregates, each micro-unit containing an equivalent proportion of each constituent of the mixture.

The mixture after dilution and freeze-drying gave a white powder forming a compact homogeneous cake, which could very easily be taken up into solution in pure water or a solvent able to restore the osmolarity of the solution (5% glucose, 5% mannitol). The solution showed a very slight opalescence. The pH obtained after taking up in a non-buffered solvent was 4.90. Raising the pH by 1 unit caused a slow precipitation: this behaviour contributed to the formation of a deposit during subcutaneous or intramuscular injection.

d) Test of Uniformity of Concentration on Batch CK9

According to the Pharmacopoeia, powders for parenteral use are subjected to a requirement of uniformity of concentration. The test must be performed on 10 random samples, which are analysed individually for the active ingredient using an appropriate analytical method. The preparation satisfies the test if the concentration of each sample is between 85 and 115% of the average concentration.

The test was performed on 15 random samples, taken up in solution and diluted in 80% acetic acid according to a standardized operational procedure, so as always to inject an identical proportion of about 15 µg, defined during preparation of the calibration curve. Each sample was injected three times, the concentration of each active ingredient corresponding to the average of the three values obtained.

The values obtained are given in table 12 below. The distribution of the values is clearly statistical. All the values are within a range defined for a two-sided test with P=0.975 (except for three deviant values, all from flask n° 1, which may correspond to a dilution error). The minimum and maximum values defined are within the limits imposed by the Pharmacopoeia (the difference observed was within 4 and 14.95% depending on the peptide, a variation linked to the inherent imprecision of the analysis method).

The absence of micro-heterogeneity of the solution was confirmed by the fact that the apportioned vaccine doses satisfied the concentration uniformity test.

EXAMPLE 2

Preparation of a Mixture of Lipopeptides (SIV-Mortara 1) and Test of Immunogenicity in Macagues 1) Preparation of the Batch SIV-MORTARA 1

This small batch was prepared in order to perform a pre-clinical test on macaques, to verify the tolerance and immunogenicity. This batch resulted from the mixture of the following lipopeptides:

| Name | Formula | SEQ ID NO: |
|---|---|---|
| NEF 101 | SVRPKVPLRAMTYKLAIDMSHFIKEKK(Pam)-NH$_2$ | 23 |
| NEF 125 | EKGGLEGIYYSARRHRILDMYLEK(Pam)-NH$_2$ | 24 |
| NEF 155 | DWQDYTSGPGIRYPKTFGWLWKLVK(Pam)-NH$_2$ | 25 |
| NEF 201 | SKWDDPWGEVLKAWKFDPTLAYTYEAK(Pam)-NH$_2$ | 26 |
| NEF 221 | YTYEAYARYPEELEASQACQRKRLEEGK(Pam)-NH$_2$ | 27 |
| GAG 165 | KFGAEVVPGFQALSEGCTPYDINQMLNC-VGDK(Pam)-NH$_2$ | 28 |
| GAG 246 | QIQWMYRQQNPIVGNIYRRWIQLGLQKC-VRMYNPTNK(Pam)-NH$_2$ | 29 |
| TT | Ac-QYIKANSKFIGITELKKK(Pam)-NH$_2$ | 30 |

Their mixing was performed from solutions in concentrated acetic acid, as for the preparation of batch CK3.

2) Immunogenicity in Macagues.

a) Materials and Methods

The macaques, respectively numbered 102, 105, 109, 117, 120, 125, 127 and 129 were immunized by subcutaneous injection of the batch prepared above (500 µg), in sterile water, and were reinjected after periods of thirty days and sixty days.

These immunizations were performed in accordance with the directives of the European Union.

Preparation of CTL Lines

Blood cells (PBMC) were isolated by density gradient centrifugation through a lymphocyte separation medium (Pharmacia, Uppsala, Sweden). They were used immediately, or stored at −180° C. in liquid nitrogen. Anti-peptide CTL lines were obtained by cultivating the monkey PBMC ($2\times10^6$ cells/ml) in microtitration plates, in RPMI 1640 supplemented with penicillin (100 U/ml), streptomycin (100 µg/ml), L-glutamine (2 mM), non-essential amino acids (1%), sodium pyruvate (1 mM), HEPES buffer (10 mM), 2-mercaptoethanol ($2\times10^{-5}$ M) and 10% fetal calf serum (FCS) inactivated by heat.

The mixture of the seven free peptides, in other words without the lipid unit (5 µM of each), corresponding to the lipopeptide sequences was added to each well.

The plates were then incubated for three days at 37° C. and interleukin-2 was added to each plate (10 IU/ml).

After seven days and fourteen days, the effector cells were stimulated by addition of new autologous PBMC, which had been in contact with the peptide mixture (5 µM of each) for two hours, then washed and irradiated (4000 rads).

Determination of the Proliferation of T Cells

PBMC cells ($2\times10^5$ in 200 µl per well) were cultivated in plates containing 1 µg/ml of lipopeptide TT (830-846), and 10 µg/ml of the peptide from tetanus toxin (TT).

After five days of culture, 1 µCi of [$^3$H]TdR was added to each well and the incubation was continued for eighteen hours. The cells were then collected using an automatic cell collector then the incorporation of tritiated thymidine was quantified using a scintillation counter.

Phenotypic Analysis of CTL Cell Lines

The phenotype of the cell lines was determined the day that the chromium release assay was performed, by incubating the cells with anti-CD4 conjugated to FITC (OKT4, Ortho Diagnostic Systems, Raritan, N.J.) and with anti-CD8 conjugated to phycoerythrin (Leu-2a, Becton Dickinson, Mountain View, Calif.) for thirty minutes at 4° C. The cells were washed with PBS buffer, then the percentage of coloured cells was determined using an Epics Elite flow cytometer (Coulter, Margency, France). Antibodies presenting a mixture of isotypes were used as controls.

In Vitro Conversion of B (B-LCL) Cell Lines

B (B-LCL) cell lines were obtained by incubating series dilutions of PBMC using the supernatant of cell line S 594. This line is infected by baboon herpes virus which immortalizes the cells (herpes virus papio). The B-LCL were then cultivated in the culture medium supplemented with 10% FCS.

Chromium Release Assay

The target cells were sensitized with the peptides. $10^6$ B-LCL cells were incubated either overnight or for 1 hour, respectively, with the long or short peptides (concentration range $10^{-5}$M-$10^{-8}$M) at 37° C. in a humid atmosphere with 5% $CO_2$. In order to obtain the target cells presenting the products of the SIVmac gene, the B-LCL were incubated at a concentration of $10^6$ cells/ml with a recombinant vaccine virus (20 PFU/cell) for eighteen hours under the same conditions. The B-LCL were then washed and marked with 100 µCi Na$_2$$^{51}$CrO$_4$ (NEN Life Science Products, Courtaboeuf Les Ullis, France) for 1 hour, washed twice and used as target cells. The $^{51}$Cr release was performed in microtitration plates. The cytolytic activity of the anti-SIV cell lines was measured by mixing $5\times10^3$ target cells marked with chromium with the effector cells, at various ratios of effector cells to target cells, in a final volume of 200 µl/well. The plates were incubated for 4 hours at 37° C., then 100 µl of supernatant was taken from each well and analysed in a gamma radiation counter.

The spontaneous release of chromium was determined by incubating the target cells with medium alone. It never exceeded 20% of the total chromium incorporated.

The specific release of chromium was measured as follows:

100×(experimental *cpm*–spontaneous *cpm*)/(maximum *cpm*–spontaneous *cpm*).

The variation within a sample never exceeded 5%.

b) Results

Figure 4:
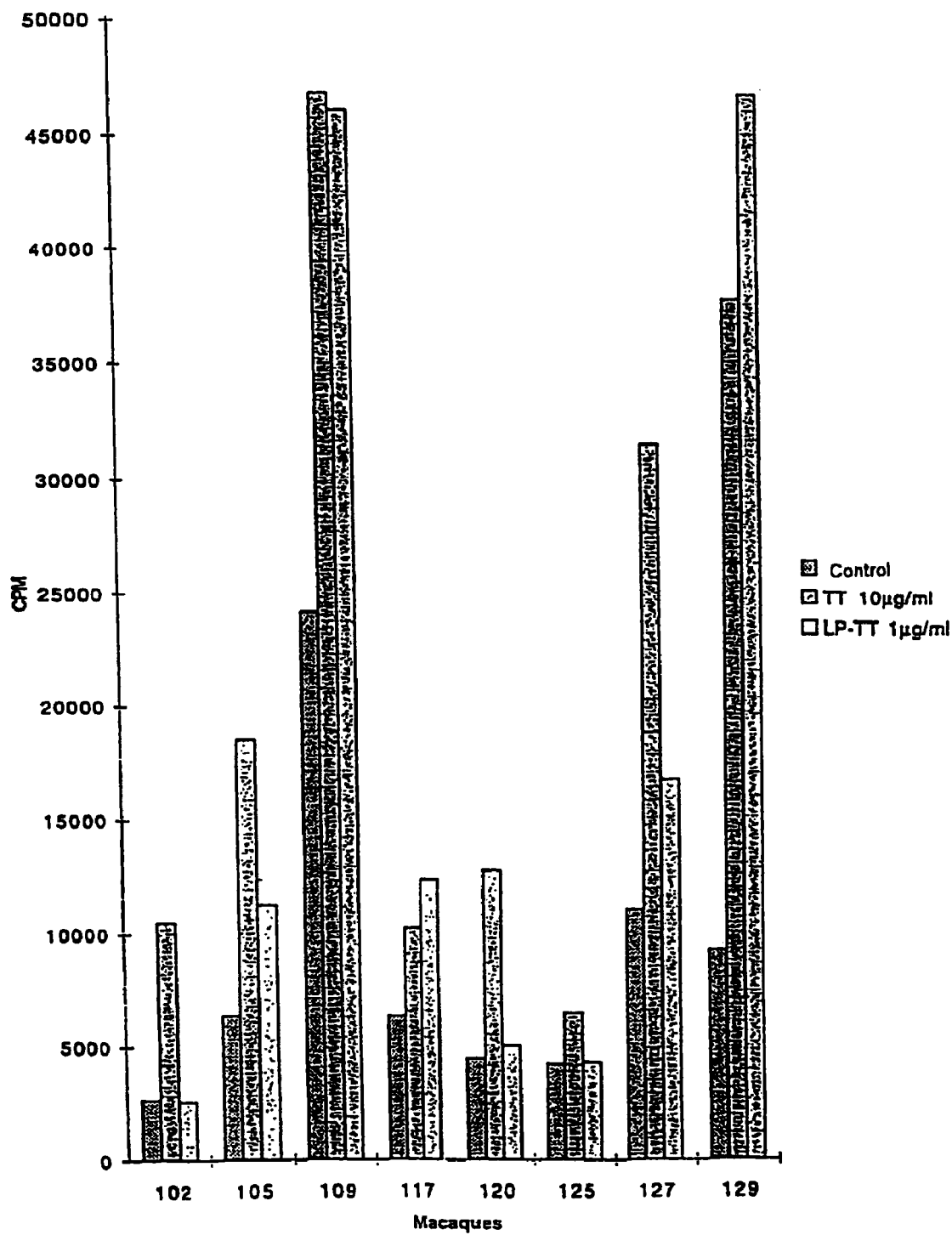
FIG. 4 shows the helper response of eight macaques immunized with a mixture of lipopeptides.
Figure 5A:
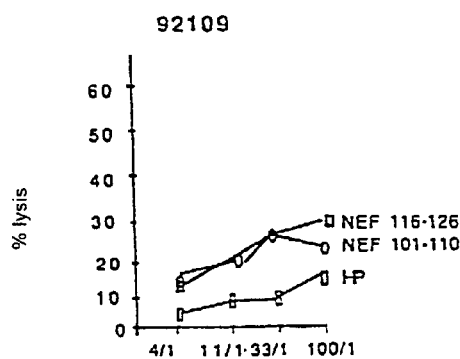
FIGS. 5A to 5F show the cytotoxic response of macaque n° 109.
Figure 5B:
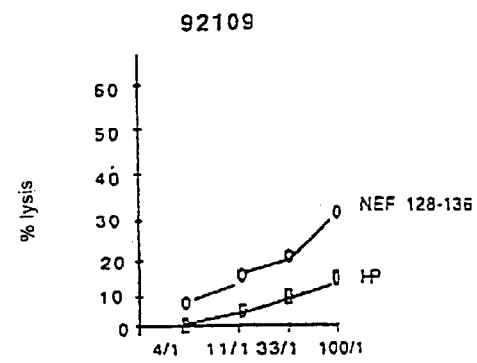
Figure 5C:
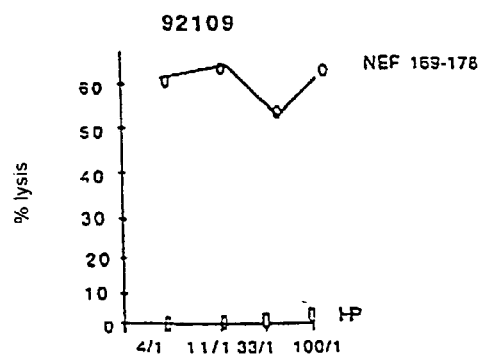
Figure 5D:
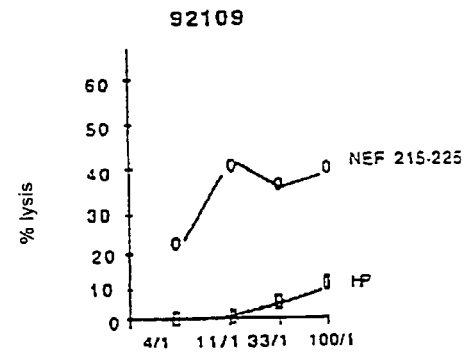
Figure 5E:
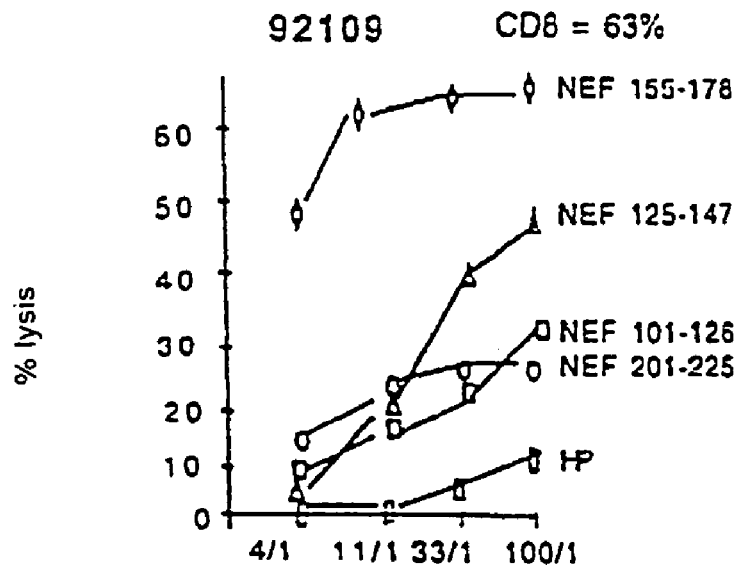
Figure 5F:
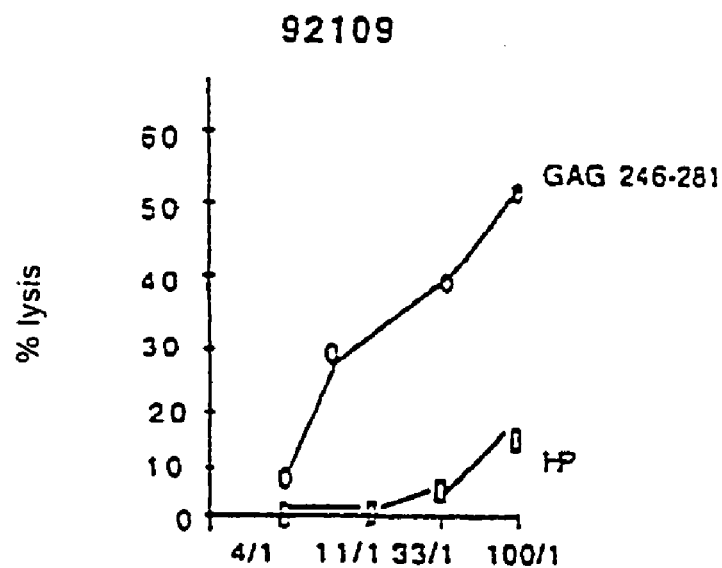
Figure 6A:
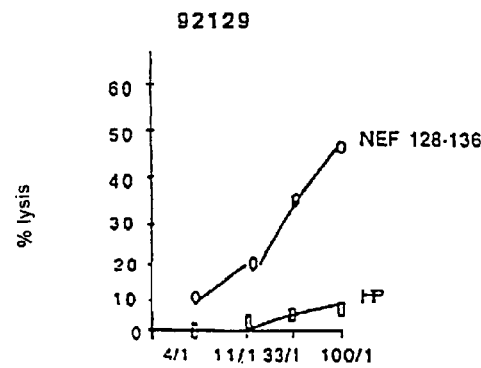
FIGS. 6A to 6D show the cytotoxic response of macaque n° 129.
Figure 6B:
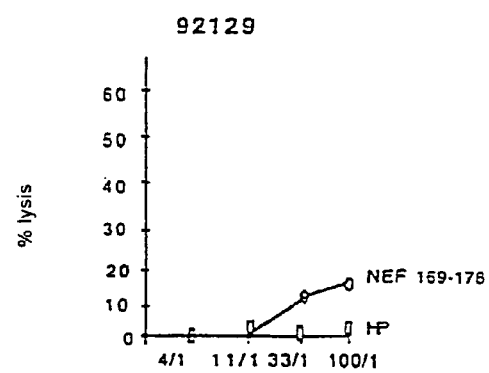
Figure 6C:
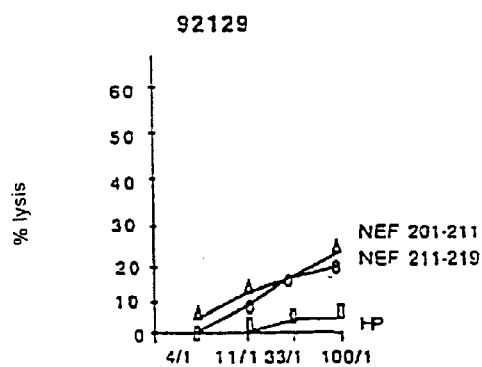
Figure 6D:
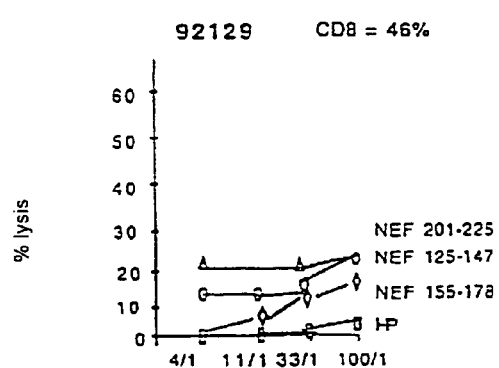
Figure 7A:
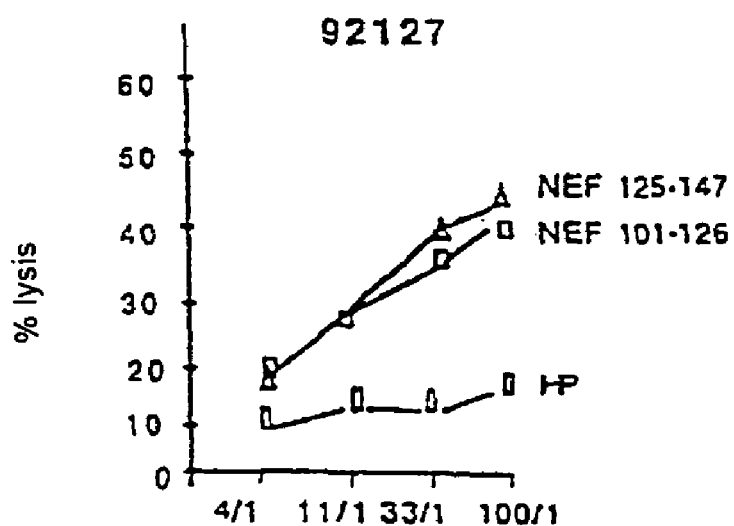
FIGS. 7A and 7B show the cytotoxic response of macaque n° 127.
Figure 7B:
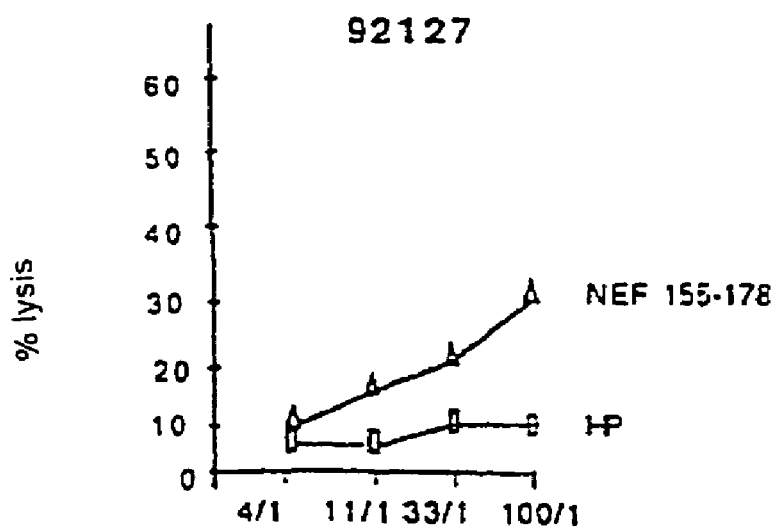
Figure 8:
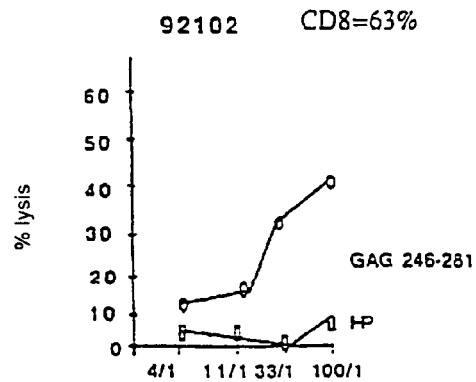
FIGS. 8, 9, 10 and 11 respectively show the cytotoxic responses of macaques n° 102, 105, 120 and 125.
Figure 9:
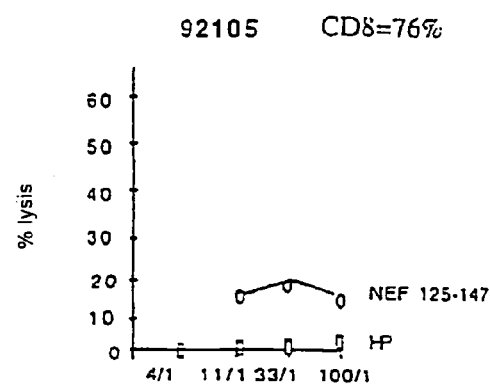
Figure 10:
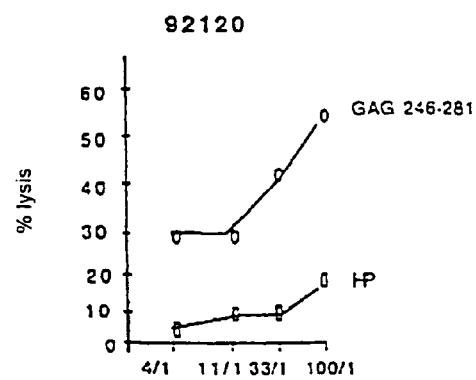
Figure 11:
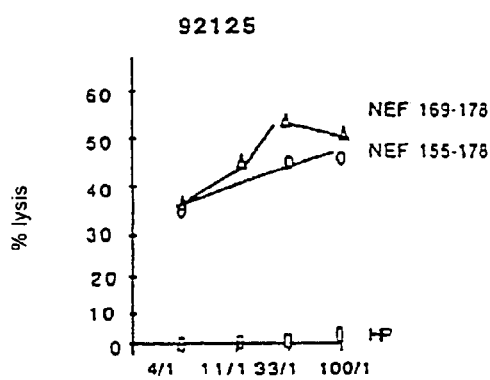

FIG. 4 shows the helper T response of the eight macaques.

FIGS. 5 to 11 show the cytotoxic response of the macaques.

The results of the immunizations with different peptides are summarized in table 13.

They show that seven of the eight macaques tested recognized different peptides, with macaques n° 109, 129 and 127 showing a particularly strong response.

The effectiveness of the induction of a CTL response confirms that the APC of the animals were able to capture and present one or more CTL antigenic determinants, and simultaneously the strong helper antigenic determinant present in the tetanus anatoxin and recognized by some of the animals.

EXAMPLE 3

Preparation of a Lipopeptide Mixture (Batch HG 1) for Clinical Tests in Man

A mixture of lipopeptides was defined for performing a clinical test (VAC 10), combining within the micelles the same peptide TT with sequences selected on the selection principle developed for VAC 04 (existence of one or more CTL antigenic determinants per sequence).

- the cysteine of peptide NEF 117 was replaced by a leucine: after synthesis and tests on cellular tests of several analogs of the CTL antigenic determinant nonapeptide containing this amino acid, it was observed that this replacement was possible; this modification avoided the stability problems due to the formation of a disulfide bridge.
- the peptide GAG 17 was selected from among other candidates for its strong cationic surface-active character, able to help to keep the other peptides in solution, and in particular GAG 253, which was retained in the mixture because of its immunogenicity in man.

The composition of this mixture, in which Pam represents a unit derived from palmitic acid and Ac the acetyl group, was the following:

| Name | Formula | SEQ ID NO: |
|------|---------|------------|
| GAG 17 | EKIRLRPGGKKKYKLKHIVK(Pam)-NH$_2$ | 31 |
| GAG 253 | NPPIPVGEIYKRWIILGLNKIVRMYSPTSIL-DK(Pam)-NH$_2$ | 6 |
| POL 325 | AIFQSSMTKILEPFRKQNPDIVIYQYMDDL-YK(Pam)-NH$_2$ | 32 |
| NEF 66 | VGFPVTPQVPLRPMTYKAAVDLSHFLKE-KGGLK(Pam)-NH$_2$ | 2 |
| NEF 116 | HTQGYFPDWQNYTPGPGVRYPLTFGWL-YKLK(Pam)-NH$_2$ | 33 |
| TT | Ac-QYIKANSKFIGITELKKK(Pam)-NH$_2$ | 30 |

This set of peptides was synthesized as described in the previous examples. The mixture of solutions was performed on a sample of 5 mg of each peptide, dissolved at a concentration of 20 mg/ml in 80% acetic acid then mixed in the following order: 1: GAG 17; 2: NEF 66; 3: NEF 116; 4: TT; 5: GAG 253; 6: POL 325.

The yields from the operation of filtering the concentrated acetic acid solutions, followed by a dilution with water, proved comparable to the yields observed for the same operations with the mixture CK3 (to within the precision of the determination). The homogeneity of the solubilities and the behaviour during the sterilizing filtration despite the heterogeneities of their individual chemical behaviour indicated the formation of mixed micelles.

EXAMPLE 4

Preparation of a Mixture of Lipopeptides Derived from Antigen LSA3 for Pre-Clinical Vaccination Tests Against the Intrahepatic Stage of *Plasmodium falciparum*, Performed in Mice and Chimpanzees, then a Clinical Test in Man

| Name | Formula | SEQ ID NO: |
|---|---|---|
| LSA3 CT1 | LLSNIEEPKENIIDNLLNNIK(Pam)-NH$_2$ | 34 |
| LSA3 NRI | Ac-DELFNELLNSVDVNGEVKENILEES-QK(Pam)-NH$_2$ | 35 |
| LSA3 NRII | Ac-LEESQVNDDIFNSLVKSVQQEQQHN-VK(Pam)-NH$_2$ | 36 |
| LSA3 RE | K(Pam)VESVAPSVEESVAPSVEESVAEN-VEESVAENV-NH$_2$ | 37 |

This set of peptides was synthesized as described in example 1. The mixture of solutions was performed on a sample of 5 mg of each peptide previously dissolved at a concentration of 20 mg/ml in 80% acetic acid then mixed in the following order: 1: LSA3 NRI; 2: LSA3 NRII; 3: LSA3 CT1; 4 LSA3 RE. The yields from the operation of filtering the concentrated acetic acid solutions, followed by a dilution with water, proved comparable for all the lipopeptides.

EXAMPLE 5

Study of the Immune Response in Man after Injection of Micelles from Batch CK9

1. Materials and Methods
Micelles Used:
The micelles which were injected were obtained as described in example 1 for batch CK9.
Long and Short Peptides.
The following long peptides corresponding to the immunogenic lipopeptides were synthesized (the positions of the amino acids on proteins NEF, GAG and ENV are given in parentheses): N1 (NEF 66 to 97), N2 (NEF 117 to 147), N3 (NEF 182 to 205), G1 (GAG 183 to 214), G2 (GAG 253 to 284) and E (ENV 303 to 335).
The following short peptides, including the lipopeptide sequences already known to be the minimal CTL antigenic determinants, were synthesized by Neosystem (Strasbourg, France):
NEF 121-128, NEF 137-145, NEF 184-191 and NEF 195-202 restricted to HLA-A1.
NEF 136-145, NEF 190-198 and GAG 183-191 restricted to HLA-A2.
NEF 73-82, NEF 84-92 and EBNA 4 (SEQ ID NO:225) 416-424HLA restricted to HLA-A11.
NEF 90-97 and NEF 182-189 restricted to HLA-B8.
NEF 134-141 and GAG 263-272 (SEQ ID NO:10) restricted to HLA-B27.
NEF 135-143 restricted to HLA-B18.
Immunization Protocol:
Volunteers were immunized by subcutaneous injection of the micelles, or the six corresponding lipopeptides, in the presence of QS21 adjuvant. The lipopeptides or micelles were injected in different ways depending on the individual.
Volunteers V4.6, V4.15, V4.16, V4.17, V4.18, and V4.28 were immunized with the six lipopeptides in the form of micelles.
Volunteer V4.6 received 250 μg of each of the lipopeptides.
Volunteers V4.15, 4.16, V4.17, V4.18, and V4.28 were immunized with 500 μg of each of the six lipopeptides.
Volunteers V4.5, V4.1, V4.19, V4.21, V4.32 and V4.34 were immunized with the six lipopeptides in the presence of QS21 adjuvant.
Volunteer V4.5 received 100 μg of the 6 lipopeptides, while volunteers V4.1, V4.19, V4.21, V4.32 and V4.34 each received 500 μg of the six lipopeptides.
All the volunteers were immunized three times with the mixture of the six lipopeptides, the two later injections being performed 4 weeks and 16 weeks respectively after the first injection.
Blood samples were taken after the first injection (hereafter referred to as week 0) and 20 weeks after the first injection (week 20).
Peripheral blood mononuclear cells (PBMC) and serum were isolated by conventional methods, and frozen.
ELISA Detection of HIV Anti-Peptide Antibodies of Immunoglobulin G (IgG) Type.
Wells of polystyrene plates were covered with 5 μg/ml of the peptides (N1, N2, N3, G1, G2 or E) overnight at 4° C. Saturation was performed using a PBS solution containing 0.1% Tween 20 and 3% bovine serum albumin (BSA). Diluted serums (1/100) were incubated in the covered wells overnight at 4° C. and the bound antibodies were detected using goat anti-human IgG conjugated with alkaline phosphatase (1/5000, Sigma). The phosphatase activity was measured using 4-methyl umbelliferyl phosphate as substrate (Sigma), and the fluorescence measurement was performed at 360/460 nm in a Cytofluor 230.0 (Millipore).
Measurement of the T Cell Responses Directed Against HIV Peptides.
PBMC ($10^5$ per well) were cultivated in complete medium with 1 μg/ml or 0.2 μg/ml of the soluble peptides (N1, N2, N3, G1, G2 or E). The proliferation was determined after 5 days culture by added 1 μCi/well of tritiated thymidine (NEN, Paris) 12 hours before their collection.
The capacity of the PBMC to proliferate in vitro was verified using independent cultures performed over 5 days with phytohemagglutinin A (PHA) of PPD (Tuberculin purified derivative Reference Statens Serumins Institute n° 2390), tetanus toxin (TT) and SEB (enterotoxin B of *Staphylococcus golden*, Reference Sigma S4881), at 1 μg/ml and 10 μg/ml respectively.
Removal of the CD4$^+$ and CD8$^+$ T cells of the PBMC was performed with anti-mouse immunoglobulins and by complement activation. To summarize, $10^7$ PBMC were incubated in 1 ml of medium lacking bovine serum albumin for 30 minutes at 4° C. with 2 μg of monoclonal antibody OKT4 or OKT8 (Ortho Diagnostic Systems).
1 ml of diluted rabbit serum complement (Hoechst Behring, Reuil, France) was added over 45 minutes at 37° C. The cell suspension was washed twice so as to remove the unbound complement. The resuspended cells were analysed using flow cytometry. Analysis of the phenotypes using anti-CD4$^+$ and anti-CD8$^+$ antibodies was performed to verify the enrichment. Finally, the cells resulting from the removal of the CD4$^+$ and CD8$^+$ cells were tested in a proliferation test.
Preparation of CTL Cell Lines
In vitro stimulation of the PBMC was performed by mixing 106 PBMC (responsive cells) with 106 irradiated stimulant cells (autologous PBMC incubated for 2 hours with different peptides) in complete RPMI culture medium (RPMI 1640 supplemented with 100 U/ml of penicillin, 100 μg/ml of streptomycin, 2 mM L-glutamine, 1 mM sodium pyruvate, 10 mM Hepes, nonessential amino acids and 10% heat-inactivated bovine serum albumin).

10 U/ml of interleukin-2 were added after 3 days. The responsive cells were restimulated each week for 3 or 4 weeks using peptides incubated with autologous PBMC (prepared in the same way as on day 0), in a medium supplemented with 10 U/ml of interleukin-2. After 3 or 4 stimulations, the CTL cells were tested using the EBV autologous cell line as target overnight with 10 μg of the different peptides (N1, N2, N3, G1, G2 or E) for $10^6$ cells.

In order to obtain the target cells presenting the products of the HIV gene, EBV target cells were infected, at a rate of $10^6$ cells/ml, with a wild type (WT) vaccine virus or with HIV-1/LAI, HIV-1/MN, HIV/A or HIV/ROD NEF recombinant vaccine viruses overnight (20 PFU/cell).

The different target cells were then washed and marked with 100 μCi of $Na_2^{51}CrO_4$ (NEN Life Science Products, Les Ullis, France).

The cytolytic activity was measured in a $^{51}Cr$ release test, over 4 hours. The average spontaneous release did not exceed 20% of the total $^{51}Cr$ incorporation.

The results are expressed as follows:

specific release of chromium=100×(measured *cpm*/spontaneous *cpm*)/(maximum *cpm*−spontaneous *cpm*).

The removal of the $CD4^+$ and $CD8^+$ cells from the PBMC was performed as described above.

ELISPOT γ-Interferon Test

96-Well microcells plates (MultiScreen-HA, Millipore S.A., Molsheim, France) were covered with 5 μg/ml of mouse anti-human-γ-interferon antibody, as capture antibody (Genzyme Corporation, Cambridge, Mass., USA) overnight at 4° C.

After washing, the wells were saturated with complete RMPI medium and PBMC which had been freshly isolated, or kept cold, were added ($2 \times 10^5$ cells per well) with different peptides corresponding to the minimal $CD8^+$ antigenic determinants (10 μg/ml).

After 24 hours incubation at 37° C. in an incubator (5% $CO_2$), the plates were washed and incubated for 2 hours with 100 μl rabbit anti-human-γ-interferon polyclonal antibody (1/250, Genzyme). After washing, a rabbit anti-IgG-biotin conjugate (1/500, Boehringer Mannheim France S.A., Meylan, France) was incubated for 1 hour. Finally, extravidine marked with alkaline phosphatase (Sigma-Aldrich Chimie S.A.R.L., St Quentin Fallavier, France) was added over 1 hour.

100 μl of alkaline phosphatase chromogenic substrate (Bio Rad Laboratories, Hercules, Calif., USA) were added to develop the spots. The blue spots were then counted using a microscope.

The negative control consisted of PBMC incubated alone in the medium, or incubated with a peptide corresponding to a $CD8^+$ antigenic determinant derived from the HIV virus presented by adapted HLA.

The positive control consisted of activating the PBMC with 50 mg/ml of PMA (Phorbol myristate acetate, reference Sigma P 8139) and 500 ng/ml of ionomycin (100 to 300 PBMC per well were added).

This strong mitogen stimulation allowed measurement of the viability of the T lymphocytes, and verification of the quality of the storage in the cold.

2. Results

Tolerance of the Treatment.

The secondary effects from the injection of the lipopeptides were not serious. An epidermal reaction was observed at the injection site. Local reactions consisted of small erythemas lasting only 24 to 48 hours. These effects were in no case associated with systemic symptoms. These observations show that the lipopeptides are well tolerated in normal individuals.

Specific Induction of a Humoral Response Against HIV-1 Peptides

Serum samples were collected before the start of the vaccinations (week 0) and at the twentieth week, after the third injection.

The serums from the immunized volunteers were tested by ELISA for the presence of IgG antibody directed against the NEF (N1, N2, N3), GAG (G1, G2), and ENV (E) peptides No IgG specific for the HIV peptides was detected before the injection in the twelve subjects listed in table 14.

At the twentieth week, anti-N1 IgG antibodies were detected in five of the vaccinated subjects (V4.6, V4.28, V4.1 (SQ21), V4.32 (QS21), and V4.34 (QS21)), and anti-N2 IgG antibodies were detected in the serums of ten of the subjects, among the twelve vaccinated. No antibody of type anti-N3 IgG was detected. The titration in anti-N2 antibody was negative in the serums of individuals V4.17 and V4.18. The antibody titration was three to five times 1 greater than that of the negative control in the serums of V4.15, V4.16, V4.1 (QS21), V4.5 (QS21) and V4.21 (QS21). The antibody titration was five to ten times greater than that of the negative control in the serums of V4.6, V4.19 (QS21), and V4.28. Finally, the serums of patients V4.32 (QS21) and V4.34 (QS21) showed antibody titration at least 10 times greater than that of the negative control.

After 3 injections, no anti-G1 IgG antibody was detected, but anti-G2 IgG antibodies were detected in the serums of the 12 individuals vaccinated. The anti-G2 antibody titration was 2 to 3 times greater than that of the negative control for patient V4.18 (QS21), the antibody titration was 5 to 10 times greater than that of the negative control for individuals V4.16, V4.17, V4.5 (QS21), V4.19 (QS21) and V4.21 (QS21). The serums of patients V4.6, V4.15, V4.28, V4.1 (QS21), V4.32 (QS21) and V4.34 (QS21) had an antibody titration more than ten times greater than that of the negative control. The serums of 6 of the 12 individuals tested, V4.28, V4.1 (QS21), V4.5 (QS21), V4.19 (QS21), V4.32 (QS21) and V4.34 (QS21) contained specific anti-E antibodies.

Specific Helper T Cell Response of the HIV-1 Virus Peptides.

The proliferative responses with respect to the soluble peptides obtained with the PBMC cells of the different individuals vaccinated are shown in table 15.

The NEF, GAG and ENV peptides caused proliferation of the donor PBMC only, after the vaccination. The PBMC of the individuals immunized with the lipopeptides (with or without QS21 adjuvant) proliferated against at least one peptide after 20 weeks (4 weeks after the third injection, for 8 subjects out of 10 given in table 15).

No proliferation was observed for the PBMC of individuals V4.15 and V4.17.

The PBMC of individual V4.6 proliferated in response to peptides N3, G1 and G2 with a proliferation index of between 4 and 10. An induction of the proliferation in response to G1, G2 and E was observed with the PBMC of individual V4.16. The PBMC of individual V4.28 were able to proliferate in response to peptides N1, N3, G2 and E. A proliferative response against peptides N1, G2 and E was observed for the PBMC of vaccinated individual V4.5.

A strong proliferation was observed in response to peptides N1, G2 and E with the PBMC of individual V4.19 (QS21), which in addition were able to proliferate in the presence of N2 and N3.

The PBMC of individual V4.21 proliferated in the presence of N1 and G2, while those of individuals V4.32 proliferated only in the presence of G2.

A proliferative response was observed in the presence of N1, N3, G2 and E with the PBMC of individual V4.34 (QS21).

Overall the third immunization with the lipopeptides induced a proliferative response against peptide N1 for five of the ten subjects treated, against N2 for one of the ten subjects treated, N3 for four of the ten subjects treated, G1 for two of the ten subjects treated, G2 for eight of the ten subjects treated, and finally E for five of the ten subjects treated.

The removal experiments performed with the PBMC from the different individuals vaccinated showed that the proliferation of the PBMC recovered after twenty weeks occurred preferentially via the helper $CD4^+$ T cells.

Induction of CTL Activity Specific to HIV

The PBMC obtained before and after the immunizations were stimulated in vitro and tested for their CTL activity specific to HIV.

The results of representative experiments are given in table 16.

The specific CTL activity was tested against the EBV autologous cell line, incubated with or without the NEF, GAG and ENV peptides. No anti-HIV response was detected with the PBMC recovered before the immunization. A specific CTL activity was detected in the PBMC collected three weeks after the immunization for nine of the twelve individuals.

Table 16 summarizes the cytotoxic activity of eight of the vaccinated individuals, the activity of one other individual being shown in FIG. 12.

At least one peptide contained in the lipopeptide vaccine induced specific CTL effector cells recognizing the HIV peptides.

For example, the PBMC of individual V4.6 recognized in a cytotoxic test the EBV autologous cells stimulated with peptides G2 and E. The PBMC of individual V4.16 recognized peptide N3 and E. The percentage of lysis was variable, weak for individual V4.16 recognizing peptide N3, intermediate for individual V4.18 with peptide N1 and strong for individual V4.5 (QS21) with peptides N2 and G2.

A specific CTL activity was also generated against peptides containing a minimal $CD8^+$ HIV antigenic determinant (individuals V4.16 and V4.28).

In order to evaluate whether the effector cells are $CD8^+$ T cells, as might be expected for the CTL specific for class-I restricted antigens, the $CD8^+$ or $CD4^+$ T lymphocytes were removed from the PBC and a cytotoxicity test was performed.

In representative experiments performed with the PBMC of individual V4.1 (FIG. 12), an effective lysis was observed of the autologous EBV cells incubated with the HIV peptides, for the PBMC and the $CD8^+$ cells. Enrichment in $CD8^+$ cells increased the percentage of specific lysis. These results confirm that the anti-HIV cytotoxic activity operates via $CD8^+$ T cells.

It was also important to determine whether the cytotoxic T cells (CTL) recognized and lysed cells infected with the virus.

PBMC from individual V4.5, collected 20 weeks after immunization, and stimulated in vitro with peptide N2, were thus tested for their CTL activity against autologous targets infected with different viruses expressing the recombinant NEF protein. The results of representative experiments are given in FIG. 13. Anti-peptide N2 CTL obtained from individual V4.5 (QS21) recognized an antigen naturally modified by autologous EBV-LCL infected with recombinant viruses of the vaccine coding for the HIV-NEF genes obtained from different strains of HIV.

For the same effector/target ratio, CTL specific to the HIV virus recognized NEF-LAI and NEF-MN with the same effectiveness. A lower percentage of specific lysis was obtained for the NEF-A protein or the NEF-ROD protein.

These results show that the CTL obtained after vaccination with the lipopeptides are able to recognize different strains of the HIV virus.

$CD8^+$ T Cells Secreting γ-Interferon Ex-Vivo, Specific to the HIV Virus

Effector $CD8^+$ T cells may exercise a lytic activity and/or produce lymphokines. The quantity of $CD8^+$ T cells secreting γ-interferon was thus evaluated by a specific ELISPOT test.

A recent study has shown that the intracellular inactivation of the hepatitis B virus occurs via $CD8^+$ T cells secreting specific and cytotoxic γ-interferon, which induced a protective immunity. This approach was used to identify the minimal antigenic determinants of $CD8^+$ T cells by sensitization of PBMC with the short peptides. All the short peptides used have already been described as being CTL antigenic determinants (see above).

An ELISPOT has also been used to quantify ex vivo the number of $CD8^+$ T cells secreting γ-interferon specific to HIV peptides in the PBMC of the vaccinated subjects (table 17).

CONCLUSION

This study has shown that a lipopeptide vaccine in the form of micelles, and without adjuvant, containing different HIV antigenic determinants contained in the viral proteins NEF, GAG and ENV of the HIV virus, is able to induce a strong and persistent multi-antigenic determinant B and T response in man.

TABLE 1

Antigenic determinants of BCR-ABL

| Peptide | | Sequence | Seq. I.D. No. | Fixation to HLA |
|---|---|---|---|---|
| 247-255 | | EDAELNPRF | 38 | B44 |
| 488-496 | | SELDLEKGL | 39 | B44 |
| 768-776 | | DELEAVPNI | 40 | B44 |
| 901-934 | b2a2 | KEDALQRPV | 41 | B44 |
| 902-935 | b2a2 | EDALQRPVA | 42 | B44 |
| 986-994 | | GEKLRVLGY | 43 | B44 |
| 1176-1184 | | EDTMEVEEF | 44 | B44 |
| 1252-1260 | | MEYLEKKNF | 45 | B44 |
| 1691-1699 | | NEEAADEVF | 46 | B44 |
| 49-57 | | VNQERFRMI | 47 | B8 |
| 580-588 | | LFQKLASQL | 48 | B8 |
| 722-730 | | ARKLRHVFL | 49 | B8 |
| 786-794 | | ALKIKISQI | 50 | B8 |
| 886-893 | | CVKLQTVH | 51 | B8 |
| 928-936 | b3a2 | KALQRPVAS | 52 | B8 |
| 1830-1838 | | GAKTKATSL | 53 | B8 |
| 1975-1983 | | IQQMRNKFA | 54 | B8 |
| 1977-1984 | | QMRNKFAF | 55 | B8 |
| 252-260 | | NPRFLKDNL | 56 | B7 |
| 329-338 | | TPDCSSNENL | 57 | B7 |
| 693-701 | | TPRRQSMTV | 58 | B7 |
| 1058-1066 | | SPGQRSISL | 59 | B7 |
| 1196-1205 | | HPNLVQLLGV | 60 | B7 |
| 1560-1569 | | SPKPSNGAGV | 61 | B7 |
| 1717-1725 | | KPLRRQVTV | 62 | B7 |
| 1878-1884 | | SPAPVPSTL | 63 | B7 |

TABLE 1-continued

Antigenic determinants of BCR-ABL

| Peptide | | Sequence | Seq. I.D. No. | Fixation to HLA |
|---|---|---|---|---|
| 36-44 | | ERCKASIRR | 64 | B27 |
| 71-79 | | DRQRWGFFRR | 65 | B27 |
| 575-583 | | QRVGDLFQK | 66 | B27 |
| 834-842 | | FRVHSRNGK | 67 | B27 |
| 642-650 | | LLYKPVDRV | 68 | A2 |
| 684-692 | | FLSSINEEI | 69 | A2 |
| 708-716 | | QLLKDSFMV | 70 | A2 |
| 714-722 | | FMVELVEGA | 71 | A2 |
| 817-825 | | KLSEQESLL | 72 | A2 |
| 881-889 | | MLTNSCVKL | 73 | A2 |
| 908-917 | | GLYGFLNVIV | 74 | A2 |
| 912-920 | | FLNVTVHSA | 75 | A2 |
| 1240-1248 | | VLLYMATQI | 76 | A2 |
| 1903-1911 | | FIPLISTRV | 77 | A2 |
| 1932-1940 | | VVLDSTEAL | 78 | A2 |
| 50-58 | | NQERFRMIY | 79 | A1 |
| 223-231 | | VGDASRPPY | 80 | A1 |
| 549-558 | | KVPELYEIHK | 81 | A3/A11 |
| 583-591 | | KLASQLGVY | 82 | A3/A11 |
| 715-724 | | MVELVEGARK | 83 | A3/A11 |
| 916-923 | | IVHSATGFK | 84 | A3/A11 |
| 920-928 | b3a2 | ATGFKQSSK | 85 | A3/A11 |
| 924-932 | b3a2 | KQSSKALQR | 86 | A3/A11 |
| 1156-1165 | | EVYEGVWKKY | 87 | A3/A11 |
| 1311-1320 | | SLAYNKFSIK | 88 | A3/A11 |
| 1499-1509 | | NLFSALIKK | 89 | A3/A11 |
| 1724-1734 | | TVAPASGLPHK | 90 | A3/A11 |
| 1905-1914 | | LISTRVSLRK | 91 | A3/A11 |
| 1922-1930 | | RIASGAITK | 92 | A3/A11 |
| 924-936 | b3a2 | KQSSKALQRPVAS | 93 | DR4 |

TABLE 2

Antigenic determinants of p53

| | SEQ ID NO: |
|---|---|
| antigenic determinants of p53 binding to HLA-A1: | |
| RVEGNLARVEY (196-205) | 94 |
| GSDCTTIHY (226-234) | 95 |
| antigenic determinants of p53 binding to HLA-A2: | |
| LLPENNVLSPL (25-35) | 96 |
| RMPEAAPPV (65-73) | 97 |
| RMPEAAPRV | 98 |
| ALNKMFCQL (129-137) | 99 |
| STPPPGTRV (149-157) | 100 |
| GLAPPQHLIRV (187-197) | 101 |
| LLGRNSFEV (264-272) | 102 |
| PLDGEYFTL (322-330) | 103 |
| antigenic determinants of p53 binding to HLA-A3: | |
| RVRAMAIYK (156-164) | 104 |
| RRTEEENLR (282-290) | 105 |
| ELPPGSTKR (298-306) | 106 |
| antigenic determinants of p53 binding to HLA-B7: | |
| LPENNVLSPL (26-35) | 107 |
| APRMPEAAPPV (63-73) | 108 |
| APRMPEAAPRV | 109 |
| APPQHLIRV (189-197) | 110 |
| RPILTIITL (249-257) | 111 |
| KPLDGETYFTL (321-330) | 112 |
| antigenic determinants of p53 binding to HLA-B8: | |
| CQLAKTCPV (135-143) | 113 |
| GLAPPQHLI (187-195) | 114 |
| NTFRHSVVV (210-218) | 115 |

TABLE 2-continued

Antigenic determinants of p53

| | SEQ ID NO: |
|---|---|
| antigenic determinants of p53 binding to HLA-B51: | |
| LLPENNVLSPL (25-35) | 116 |
| RMPEAAPPV (65-73) | 117 |
| LIRVEGNLRV (194-203) | 118 |

TABLE 3

Antigenic determinants of proteins $E_6$ and $E_7$

| | |
|---|---|
| YMLDLQPETT (E7 11-20) | SEQ ID NO: 119 |
| LLMGTLGIV (E7 82-90) | SEQ ID NO: 120 |
| TLGIVCPI (E7 86-93) | SEQ ID NO: 121 |
| TIHDIILECV (E6 29-38) | SEQ ID NO: 122 |
| KLPQLCTEL (E6 18-26) | SEQ ID NO: 123 |
| RPPKLPQL (E6 8-15) | SEQ ID NO: 124 |
| LRREVYDFAFRDLCIVYRDGNPY (E6 45-67) | SEQ ID NO: 125 |
| ISEYRHYCY (E6 80-88) | SEQ ID NO: 126 |
| EKQRHLDKKQRFHNIRGRWT (E6 121-140) | SEQ ID NO: 127 |
| GQAEPDRAHYNIVTF (E7 43-57) | SEQ ID NO: 284 |
| QAEPDRAHY (E7 44-52) | SEQ ID NO: 128 |
| EPDRAHYNIV (E7 46-55) | SEQ ID NO: 129 |

TABLE 4

Antigenic determinants of the HIV-1 virus

| HLA-A1 | |
|---|---|
| (Nef 96-106: GLEGLIHSQRR | SEQ ID NO: 130 |
| (Nef 121-128: FPDWQNYT | SEQ ID NO: 131 |
| (Nef 137-145: LTFGWCYKL | SEQ ID NO: 132 |
| (Nef 184-191: RFDSRLAF | SEQ ID NO: 133 |
| (Nef 195-202: ARELHPEY | SEQ ID NO: 134 |
| HLA-A2 | |
| Gp120 121-129: KLTPLCVTL | SEQ ID NO: 135 |
| P17 77-85: SLYNTVATL | SEQ ID NO: 136 |
| RT 200-208: ALVEICTEM | SEQ ID NO: 137 |
| RT 275-285: VLDVGDAYFSV | SEQ ID NO: 138 |
| RT 346-354: KIYQYMDDL | SEQ ID NO: 139 |
| RT 368-376: KIEELRQHL | SEQ ID NO: 140 |
| RT 376-387: LLRWGLTTPDK | SEQ ID NO: 141 |
| RT 476-484: ILKEPVHGV | SEQ ID NO: 142 |
| RT 588-596: PLVKLWYQL | SEQ ID NO: 143 |
| RT 683-692: ELVNQIIEQL | SEQ ID NO: 144 |
| Nef 136-145: PLTFGWCFKL | SEQ ID NO: 145 |
| Nef 180-189: VLQWRFDSRL | SEQ ID NO: 146 |
| Nef 190-198: ALHHVAREL | SEQ ID NO: 147 |
| Gp41 818-826: SLLNATVDI | SEQ ID NO: 148 |
| P24 183-191: DLNTMLNTV | SEQ ID NO: 149 |
| RT 346-354: VIYQYMDDL | SEQ ID NO: 150 |
| RT 588-596: PLVKLWYQL | SEQ ID NO: 152 |
| Pro 143-152: VLVGPTPVNI | SEQ ID NO: 151 |
| (Gp120 37-44: TVYYGVPV | SEQ ID NO: 153 |
| (Gp120 115-122: SLKPCVKL | SEQ ID NO: 154 |
| (Gp120 313-321: RIQRGPGRA | SEQ ID NO: 155 |
| (Gp120 197-205: TLTSCNTSV | SEQ ID NO: 156 |
| (Gp120 428-435: FINMWQEV | SEQ ID NO: 157 |
| (Gp 41 836-844: VVQGAYRAI | SEQ ID NO: 158 |
| (p24 219-228: HAGPIAPGQM | SEQ ID NO: 159 |
| (p15 422-431: QMKDCTERQA | SEQ ID NO: 160 |
| (p15 448-456: FLQSRPETA | SEQ ID NO: 161 |
| (RT 681-691: ESELVNQIIEG | SEQ ID NO: 162 |
| HLA-A3 | |
| P17 18-26: KIRLRPGGK | SEQ ID NO: 163 |
| P17 20-28: RLRPGGKKK | SEQ ID NO: 164 |
| RT 200-210: ALVEICTEMEK | SEQ ID NO: 165 |
| RT 325-333: AIFQSSMTK | SEQ ID NO: 166 |

TABLE 4-continued

Antigenic determinants of the HIV-1 virus

| | |
|---|---|
| RT 359-368: DLEIGQHRTK | SEQ ID NO: 167 |
| Nef 73-82: QVPLRPMTYK | SEQ ID NO: 168, 174, 12, 215 |
| Gp120 37-46: TVYYGVPVWK | SEQ ID NO: 169 |
| Gp41 775-785: RLRDLLLIVTR | SEQ ID NO: 170 |
| P17 18-26: KIRLRPGGK | SEQ ID NO: 171 |
| HLA-A11 | |
| | |
| RT 325-333: AIFQSSMTK | SEQ ID NO: 172 |
| RT 507-517: QIYQEPFKNLK | SEQ TD NO: 173 |
| Nef 73-82: QVPLRPMTYK | SEQ ID NO: 174, 12, 215, 168 |
| Nef 84-92: AVDLSHFLK | SEQ ID NO: 175, 15 |
| p24 349-359: ACQVGPGHK | SEQ ID NO: 176 |
| P17 83-91: ATLYCVHQR | SEQ ID NO: 177 |
| HLA-A24 (A9) | |
| | |
| Gp120 52-61: LFCASDAKAY | SEQ ID NO: 178 |
| Gp41 591-598: YLKDQQLL | SEQ ID NO: 180 |
| or 590-597 RYLKDQQL | SEQ ID NO: 179 |
| (RT 484-492: VYYDPSKDL | SEQ ID NO: 181 |
| (RT 508-516: IYQEPFKNL | SEQ ID NO: 182 |
| (RT 681-691: ESELVNQIIEG | SEQ ID NO: 183 |
| HLA-A25 (A10) | |
| | |
| P24 203-212: ETINEEAAEW | SEQ ID NO: 184 |
| HLA-A26 (A10) | |
| | |
| P24 167-175: EVIPMFSAL | SEQ ID NO: 185 |
| HLA-A30 (A19) | |
| | |
| (Gp41 845-852: RAIRHIPRR | SEQ ID NO: 186 |
| HLA-A31 (A19) | |
| | |
| (Gp41 775-785: RLRDLLLIVTR | SEQ ID NO: 187 |
| HLA-A32 (A19) | |
| | |
| Gp120 424-432: RIKQIINMW | SEQ ID NO: 188 |
| (Gp41 774-785: HRLRDLLLI | SEQ ID NO: 189 |
| RT 559-568: PIQKETWETW | SEQ ID NO: 190 |
| HLA-A33 (A19) | |
| | |
| (P24 266-275 :IILGLNKIVR | SEQ ID NO: 191 |
| HLA-B7 | |
| | |
| RT 699-707: YLAWVPAHK | SEQ ID NO: 192, 197 |
| Nef 68-77: FPVTQVPLR | SEQ ID NO: 194 |
| Nef 128-137: TPGPGVRYPL | SEQ ID NO: 193 |
| Gp120 303-312: RPNNNTRKSI | SEQ ID NO: 195 |
| Gp41 848-856: IPRRIRQGL | SEQ ID NO: 196 |
| RT 699-707: YLAWVPAHK | SEQ ID NO: 197, 192 |
| HLA-B8 | |
| | |
| Gp120 2-10: RVKEKYQHL | SEQ ID NO: 198 |
| P17 24-32 :GGKKKYKLK | SEQ ID NO: 199 |
| Nef 90-97: FLKEKGGL | SEQ ID NO: 200, 22 |
| P24 259-267: GEIYKRWII | SEQ ID NO: 201 |
| Gp41 591-598: YLKDQQLL | SEQ ID NO: 202 |
| (Gp41 849-856: PRRIRQGL | SEQ ID NO: 203 |
| or 851-859: RIRQGLERIL | SEQ ID NO: 204 |
| (P24 329-337: DCKTILKAL | SEQ ID NO: 205 |
| (RT 185-193: GPKVKQWPL | SEQ ID NO: 206 |
| (Nef 182-189: EWRFDSRL | SEQ ID NO: 207 |
| HLA-B14 | |
| | |
| Gp41 589-597: ERYLKDQQL | SEQ ID NO: 208 |
| P24 298-306: DRFYKTLRA | SEQ ID NO: 210 |
| (P24 183-191?: DLNTMLNTV | SEQ ID NO: 209 |
| (p24 304-313: LRAEQASVQEV | SEQ ID NO: 211 |
| (p24 305-313: RAEQASVQEV | SEQ ID NO: 212 |
| HLA-B18 | |
| | |
| (Nef 135-143:YPLTFGWCY | SEQ ID NO: 213 |
| (Nef 135-143:YPLTFGWCF | SEQ ID NO: 214 |
| HLA-B27 | |
| | |
| P24 263-272: KRWIILGLNK | SEQ ID NO: 10 |
| | |
| Nef 73-82: QVPLRPMTYK | SEQ ID NO: 215, 12, 174, 168 |
| Nef 134-141: RYPLTFGW | SEQ ID NO: 19 |
| or 133-141: YPLTFGW | SEQ ID NO: 216 |
| Gp41 589-597 ERYLKDQQL | SEQ ID NO: 217 |
| (Gp41 791-800: GRRGWEALKY | SEQ ID NO: 218 |
| HLA-B35 | |
| | |
| Gp120 78-86: DPNPQEVVL | SEQ ID NO: 219 |
| Gp120 257-265: RPVVSTQLL | SEQ ID NO: 220 |
| RT 285-294: VPLDKDFRKY | SEQ ID NO: 221 |
| RT 323-331: SPAIFQSSM | SEQ ID NO: 222 |
| RT 342-350: NPDIVTYQY (consensus clade B) | SEQ ID NO: 223 |
| RT 460-468: IPLTEEAEL | SEQ ID NO: 224 |
| RT 598-608: EPIVGAETFY | SEQ ID NO: 225 |
| Nef 68-76: FPVRPQVPL | SEQ ID NO: 226 |
| Nef 74-81: VPLRPMTY | SEQ ID NO: 13 |
| Gp41 611-619: TAVPWNASW | SEQ ID NO: 227 |
| Gp120 42-52: VPVWKEATTTL | SEQ ID NO: 228 |
| P17 124-132: NSSQVSQNY (consensus clade B) | SEQ ID NO: 229 |
| P24 254-262: PPIPVGEIY(consensus clade B) | SEQ ID NO: 9 |
| HLA-B37 | |
| | |
| Nef 120-128: YFPDWQNYT | SEQ ID NO: 17 |
| HLA-B44 (B12) | |
| | |
| P24 178-186: SEGATPQDL | SEQ ID NO: 230 |
| (p24 175-184: LESGATPQDL | SEQ ID NO: 231 |
| HLA-B51 (B5) | |
| | |
| gp41 562-570: RAIEAQQHL | SEQ ID NO: 232 |
| RT 200-208: ALVEICTEM | SEQ ID NO: 233 |
| RT 209-217: EKEGKISKI | SEQ ID NO: 234 |
| RT 295-302: TAFTIPSI | SEQ ID NO: 235 |
| HLA-B52 (B5) | |
| | |
| Nef 190-198: AFHHVAREL | SEQ ID NO: 21 |
| HLA-B55 (B22) | |
| | |
| Gp120 42-51: VPVWKEATTT | SEQ ID NO: 236 |
| HLA-B57 and B58 (B17) | |
| | |
| P24 240-249: TSLTQEQIGW | SEQ ID NO: 237 |
| Nef 116-125: HTQGYFPDWQ | SEQ ID NO: 238 |
| or 116-124: HTQGYFPDW | SEQ ID NO: 239 |
| Nef 120-128: YFPDWQNYT | SEQ ID NO: 17 |
| (P24 147-155: ISPRTLNAW | SEQ ID NO: 240 |
| (P24 164-172: FSPEVIPMF | SEQ ID NO: 241 |
| HLA-Bw62 (B15) | |
| | |
| P17 20-29: RLRPGGKKKY | SEQ ID NO: 242 |
| P24 268-277: LGLNKIVRMY | SEQ ID NO: 11 |
| RT 427-438: LVGKLNWASQIY | SEQ ID NO: 243 |
| Nef 84-91: AVDLSHFL | SEQ ID NO: 14 |
| Nef 117-127: TQGYFPDWQNY | SEQ ID NO: 16 |
| HLA-Cw4 | |
| | |
| gp120 380-388: SFNCGGEFF | SEQ ID NO: 244 |
| HLA-Cw8 | |
| | |
| RT 663-672: VTDSQYALGI | SEQ ID NO: 245 |
| P24 305-313: RAEQASQEV | SEQ ID NO: 246 |
| Nef 82-91: KAALDLSHPL | SEQ ID NO: 247 |
| HLA-Cw? | |
| | |
| P24 308-316: QATQEVKNW | SEQ ID NO: 248 |

TABLE 5

Antigenic determinants of human melanoma

| Gene/ protein | MHC restriction | Peptide | Amino acid positions | SEQ ID NO: |
|---|---|---|---|---|
| | HLA-A2 | MLLAVLYCL | 1-9 | 249 |
| | HLA-A2 | YMNGTMSQV | 369-377 | 250 |
| | | YMDGTMSQV | | 252 |
| | HLA-A24 | AFLPWHRLF | 206-214 | 251 |
| | HLA-B44 | SEIWRDIDF | 192-200 | 253 |
| | HLA-DR4 | QNILLSNAPLGPQFP | 56-70 | 254 |
| | | SYLQDSDPDSFQD | 450-462 | 255 |
| Pmel17<sup>gp100</sup> | HLA-A2 | KTWGQYWQV | 154-162 | 256 |
| | HLA-A2 | AMLGTHTMEV | 177-186 | 257 |
| | HLA-A2 | MLGTHTMEV | 178-186 | 258 |
| | HLA-A2 | ITDQVPFSV | 209-217 | 259 |
| | HLA-A2 | YLEPGPVTA | 280-288 | 260 |
| | HLA-A2 | LLDGTATLRL | 457-466 | 261 |
| | HLA-A2 | VLYRYGSFSV | 476-485 | 262 |
| | HLA-A2 | SLADTNSLAV | 570-579 | 263 |
| | HLA-A3 | ALLAVGATK | 17-25 | 264 |
| Melan-A<sup>MART-1</sup> | HLA-A2 | (E)AAGIGILTV | 26(7)-35 | 266, 265 |
| | HLA-A2 | ILTVILGVL | 32-40 | 267 |
| GP75<sup>TRP-1</sup> | HLA-A31 | MSLQRQFLR | | 268 |
| TRP-2 | HLA-A31 | LLGPGRPYR | 197-205 | 269 |

TABLE 6

Tumour Antigenic determinants resulting from de mutations

| Gene/ protein | Tumour | MHC restriction | Peptide | Amino acid positions | SEQ ID NO: |
|---|---|---|---|---|---|
| MUM-1 | Melanoma | HLA-B44 | EEKLIVVLF | 30-38 | 270 |
| CDK4 | Melanoma | HLA-A2 | ACDPHSGHFV | 23-32 | 271 |
| β-catenine | Melanoma | HLA-A24 | SYLDSGIIF | 29-37 | 272 |
| HLA-A2 | Renal carcinoma | | | | — |
| CASP-8 | Squamous carcinoma of head and neck | HLA-B35 | FPSDSWCYF | 476-484 | 273 |

TABLE 7

Antigens common to different tumours

| Gene | Normal expression tissue | MHC restriction | Antigenic peptide | Amino acid positions | SEQ ID NO: |
|---|---|---|---|---|---|
| MAGE-1 | Testicles | HLA-A1 | EADPTGHSY | 161-169 | 274 |
| | | HLA-Cw16 | SAYGEPRKL | 230-238 | 275 |
| MAGE-3 | Testicles | HLA-A1 | EVDPIGHLY | 168-176 | 276 |
| | | HLA-A2 | FLWGPRALV | 271-279 | 277 |
| | | HLA-B44 | MEVDPIGHLY | 167-176 | 278 |
| BAGE | Testicles | HLA-Cw16 | AARAVFLAL | 2-10 | 279 |
| GAGE-1/2 | Testicles | HLA-Cw6 | YRPRPRRY | 9-16 | 280 |
| RAGE-1 | Retina | HLA-B7 | SPSSNRIRNT | 11-20 | 281 |
| GnTV | None | HLA-A2 | VLPDVFLRC | 38-64 | 282 |
| Mucin | Breasts during lactation | no restriction | PDTRPAPGSTAPPA HGVTSA* | | 283 |

*Aberrant transcript of the N-acetyl glucosaminyl transferase V (GnTV) found only in melanomas

TABLE 8

| LIPOPEPTIDES | FILTRATION YIELD |
|---|---|
| NEF 66 | quantitative |
| NEF 117 | 80% |
| NEF 182 | quantitative |
| GAG 183 | 80% |
| GAG 253 | 77% |
| ENV | quantitative |

TABLE 9

| Peptide | Solvent | Concentration (mg/ml) | Volume removed (ml) | Filtration yield (%) after mixing |
|---|---|---|---|---|
| NEF 66 | water | 5 | 1 | 95 |
| NEF 117 | AcOH 25% | 5 | 1 | 81 |
| NEF 182 | AcOH 25% | 5 | 1 | 92 |
| GAG 183 | AcOH 80% | 10 | 0.5 | 73 |
| GAG 253 | AcOH 25% | 5 | 1 | 31 |
| ENV | water | 5 | 1 | 95 |

TABLE 10

| Peptide | Solvent | Concentration (mg/ml) | Volume removed (ml) | Filtration yield (%) after mixing* |
|---|---|---|---|---|
| NEF 66 | AcOH 80% | 20 | 0.250 | quantitative |
| NEF 117 | AcOH 80% | 20 | 0.250 | quantitative |
| NEF 182 | AcOH 80% | 20 | 0.250 | quantitative |
| GAG 183 | AcOH 80% | 20 | 0.250 | quantitative |
| GAG 253 | AcOH 80% | 20 | 0.250 | quantitative |
| ENV | AcOH 80% | 20 | 0.250 | quantitative |

*to within the precision of the determination

TABLE 11

| Peptide | Exact weight*** (mg) | Peptide net | Quantity expected* (μg per dose) | Quantity obtained*** (μg per dose) | yield** (%) |
|---|---|---|---|---|---|
| NEF 66 | 764 | 641 | 550 | 505 ± 15 | 89.14-94.6 |

TABLE 11-continued

| Peptide | Exact weight*** (mg) | Peptide net | Quantity expected* (µg per dose) | Quantity obtained*** (µg per dose) | yield** (%) |
|---|---|---|---|---|---|
| NEF 117 | 739 | 641 | 550 | 621 ± 21 | 109.08-116.72 |
| NEF 182 | 742 | 641 | 550 | 545 ± 16 | 96.23-102.05 |
| GAG 183 | 741 | 642 | 550 | 478 ± 13 | 84.50-89.23 |
| GAG 253 | 780 | 641 | 550 | 571 ± 28 | 98.76-108.95 |
| ENV | 810 | 642 | 550 | 593 ± 17 | 104.71-110.89 |

*the target dose was 500 µg per peptide: an overdose of 10% was deliberately included at the time of weighing, given the yields obtained during the preparation of batch CK6

**the yield ranges reflect the precision of the determination, and not a significant variation from one flask to another
***the values in excess are due to imprecisions in the weighings of electrostatic powders by an operator wearing a standard pressure suit

TABLE 12

Test of uniformity of concentration

| | nef 66 | nef 117 | nef 182 | gag 183 | gag 253 | env 303 |
|---|---|---|---|---|---|---|
| | 14.40 | 17.74 | 16.19 | 13.28 | 16.74 | 17.53 |
| | 14.38 | 17.75 | 16.21 | 13.27 | 17.27 | 17.63 |
| | 14.67 | 16.36 | 16.61 | 13.41 | 16.89 | 18.36 |
| sample 1 | 14.49 | 17.28 | 16.34 | 13.32 | 16.97 | 17.84 |
| | 13.42 | 17.11 | 15.32 | 12.66 | 15.56 | 16.36 |
| | 13.81 | 17.04 | 15.32 | 12.67 | 15.89 | 16.51 |
| | 13.77 | 17.06 | 15.33 | 12.45 | 15.16 | 16.41 |
| sample 2 | 13.67 | 17.07 | 15.32 | 12.59 | 15.54 | 16.43 |
| | 13.58 | 17.08 | 15.33 | 12.68 | 15.64 | 16.29 |
| | 13.70 | 17.08 | 15.31 | 12.62 | 15.82 | 16.28 |
| | 13.59 | 17.05 | 15.31 | 12.32 | 14.85 | 16.37 |
| sample 3 | 13.62 | 17.07 | 15.32 | 12.54 | 15.44 | 16.31 |
| | 13.20 | 16.80 | 15.14 | 12.23 | 16.05 | 16.15 |
| | 14.53 | 17.34 | 15.74 | 13.06 | 15.93 | 17.17 |
| | 13.49 | 16.86 | 15.17 | 12.31 | 15.44 | 16.15 |
| sample 4 | 13.74 | 17.00 | 15.35 | 12.53 | 15.80 | 16.49 |
| | 13.88 | 17.21 | 15.40 | 12.52 | 14.78 | 16.80 |
| | 13.94 | 17.17 | 15.39 | 12.59 | 15.20 | 16.72 |
| | 13.98 | 17.19 | 15.47 | 12.96 | 15.49 | 16.71 |
| sample 5 | 13.94 | 17.19 | 15.42 | 12.69 | 15.16 | 16.74 |
| | 14.03 | 17.26 | 15.75 | 11.62 | 15.78 | 16.97 |
| | 13.99 | 17.20 | 15.73 | 11.39 | 15.77 | 17.02 |
| | 14.20 | 17.26 | 15.74 | 12.19 | 15.90 | 16.80 |
| sample 6 | 14.07 | 17.24 | 15.74 | 11.73 | 15.81 | 16.93 |
| | 13.78 | 17.29 | 15.67 | 12.69 | 16.13 | 18.04 |
| | 13.94 | 17.22 | 15.57 | 12.67 | 16.40 | 17.50 |
| | 13.95 | 17.23 | 15.55 | 12.28 | 16.19 | 17.37 |
| sample 7 | 13.89 | 17.25 | 15.60 | 12.55 | 16.24 | 17.64 |
| | 13.84 | 17.06 | 15.38 | 12.50 | 15.62 | 17.90 |
| | 13.65 | 17.09 | 15.45 | 12.44 | 16.02 | 17.73 |
| | 13.73 | 16.94 | 15.37 | nd | 16.21 | 17.54 |
| sample 8 | 13.74 | 17.03 | 15.40 | 12.47 | 15.95 | 17.73 |
| | 14.03 | 17.40 | 15.66 | 12.77 | 16.46 | 18.56 |
| | 14.07 | 17.33 | 15.72 | 11.92 | 16.61 | 18.41 |
| | 13.89 | 17.39 | 15.72 | 12.68 | 15.94 | 18.37 |
| sample 9 | 14.00 | 17.37 | 15.70 | 12.46 | 16.34 | 18.45 |
| | 13.34 | 16.88 | 15.33 | 12.07 | 14.70 | 17.92 |
| | 13.71 | 17.24 | 15.66 | 12.36 | 15.12 | 18.50 |
| | 13.53 | 16.93 | 15.44 | 12.28 | 14.44 | 18.01 |
| sample 10 | 13.53 | 17.02 | 15.48 | 12.24 | 14.76 | 18.14 |
| | 13.72 | 17.22 | 15.64 | 12.41 | 14.89 | 18.32 |
| | 13.75 | 17.33 | 15.72 | 12.36 | 14.82 | 18.31 |
| | 13.67 | 17.21 | 15.72 | 11.86 | 14.61 | 18.69 |
| sample 11 | 13.71 | 17.25 | 15.69 | 12.21 | 14.77 | 18.44 |
| | 13.62 | 17.11 | 15.60 | 12.28 | 14.75 | 18.42 |
| | 13.74 | 17.13 | 15.70 | 12.44 | 14.98 | 18.31 |
| | 13.75 | 17.16 | 15.63 | 12.51 | 15.37 | 18.32 |
| sample 12 | 13.70 | 17.13 | 15.65 | 12.41 | 15.03 | 18.35 |
| | 13.32 | 16.36 | 14.74 | 12.47 | 16.17 | 15.44 |

TABLE 12-continued

Test of uniformity of concentration

| | | | | | | |
|---|---|---|---|---|---|---|
| | 13.31 | 16.41 | 14.68 | 12.51 | 16.26 | 15.56 |
| | 13.34 | 16.38 | 14.67 | 12.53 | 16.17 | 15.43 |
| sample 13 | 13.32 | 16.38 | 14.70 | 12.50 | 16.20 | 15.48 |
| | 13.76 | 16.72 | 14.75 | 12.67 | 16.10 | 15.59 |
| | 13.56 | 16.35 | 14.75 | 12.64 | 16.16 | 15.64 |
| | 13.60 | 16.67 | 14.76 | 12.64 | 16.06 | 15.64 |
| sample 14 | 13.64 | 16.58 | 14.76 | 12.65 | 16.10 | 15.62 |
| | 13.36 | 16.40 | 14.53 | 12.48 | 15.90 | 15.64 |
| | 13.41 | 16.35 | 14.57 | 12.52 | 15.84 | 15.80 |
| | 13.44 | 16.43 | 14.50 | 12.46 | 15.77 | 15.60 |
| sample 15 | 13.40 | 16.39 | 14.53 | 12.49 | 15.84 | 15.68 |
| m | 13.69 | 16.91 | 15.28 | 12.49 | 15.81 | 16.82 |
| standard deviation | 0.27 | 0.37 | 0.42 | 0.28 | 0.59 | 1.19 |
| t's | 0.58 | 0.79 | 0.89 | 0.59 | 1.24 | 2.51 |
| min | 13.11 | 16.12 | 14.39 | 11.91 | 14.57 | 14.30 |
| max | 14.27 | 17.70 | 16.18 | 13.08 | 17.05 | 19.33 |
| Min accepted (−15%) | 11.64 | 14.37 | 12.99 | 10.62 | 13.44 | 14.29 |
| Max accepted (+15%) | 15.74 | 19.45 | 17.58 | 14.37 | 18.18 | 19.34 |
| Observed deviation | 4.23% | 4.67% | 5.84% | 4.70% | 7.84% | 14.95% | t = 2.110 3 deviant values on sample 1 (probably dilution error)

TABLE 13

| anti-7 peptide CTL lines | Peptides recognized | Short peptides recognized |
|---|---|---|
| 92102 | GAG 246-281 | |
| 92105 | NEF 125-147 | |
| 92109 | NEF 101-126 | NEF 101-110 |
| | | NEF 116-126 |
| | NEF 125-147 | NEF 128-136 |
| | NEF 155-178 | NEF 169-178 |
| | NEF 201-225 | NEF 215-225 |
| | GAG 246-281 | |
| 92120 | GAG 246-281 | |
| 92125 | NEF 155-178 | NEF 169-178 |
| 92129 | NEF 125-147 | NEF 128-136 |
| | NEF 155-178 | NEF 169-178 |
| | NEF 201-225 | NEF 201-211 |
| | | NEF 211-219 |
| 92117 | negative | |
| 92127 | NEF 101-126 | |
| | NEF 125-147 | |
| | NEF 155-178 | |

TABLE 14

Detection of specific antibodies of peptides of proteins NEF, GAG and ENV of the HIV virus, in the serum of volunteers immunized with a mixture of six lipopeptides

| | | Peptide recognized | | | | | |
|---|---|---|---|---|---|---|---|
| Volunteer[a] | Recovery period | N1 | N2 | N3 | G1 | G2 | E |
| V4.6 | W20 | 2.1 | 7.2 | 1.0 | 1.0 | 10.2 | 1.2 |
| V4.15 | W20 | 1.3 | 4.8 | 1.2 | 1.3 | 11.2 | 1.5 |
| V4.16 | W20 | 1.2 | 4.7 | 1.2 | 1.1 | 9.7 | 1.3 |
| V4.17 | W20 | 1.7 | 1.8 | 1.0 | 1.1 | 8.0 | 1.2 |
| V4.18 | W20 | 1.1 | 1.2 | 1.0 | 1.3 | 2.2 | 1.1 |
| V4.28 | W20 | 7.8 | 8.8 | 1.5 | 1 | 15 | 5.7 |
| V4.1 (QS21) | W20 | 3.1 | 3.2 | 1.1 | 1.2 | 11.5 | 4.7 |
| V4.5 (QS21) | W20 | 1.2 | 4.2 | 1.3 | 1.1 | 8.1 | 2.1 |
| V4.19 (QS21) | W20 | 1.2 | 5.3 | 1.2 | 1.3 | 5.1 | 3.8 |
| V4.21 (QS21) | W20 | 1.2 | 4.7 | 1.0 | 1.2 | 9.3 | 1.9 |

TABLE 14-continued

Detection of specific antibodies of peptides of proteins NEF, GAG and ENV of the HIV virus, in the serum of volunteers immunized with a mixture of six lipopeptides

| Volunteer[a] | Recovery period | Peptide recognized | | | | | |
|---|---|---|---|---|---|---|---|
| | | N1 | N2 | N3 | G1 | G2 | E |
| V4.32 (QS21) | W20 | 6.6 | 14 | 1.8 | 1.9 | 21 | 4 |
| V4.34 (QS21) | W20 | 7.1 | 21.2 | 1.2 | 1.8 | 36 | 8 |

[a]The volunteers were immunized with six lipopeptides in the form of micelles, or with an adjuvant (QS21)
[b]The serums of the volunteers were recovered before injection of the lipopeptides, and twenty weeks after. The three injections of the six lipopeptides were administered at 0.4 and 16 weeks.
[c]The detection of the specific antibodies of the peptides of the HIV virus was performed using an ELISA assay with serum dilution to 1/100. The ELISA assay plates were covered with NEF 66-97 (N1), NEF 117-147 (N2), NEF 182-205 (N3), GAG 183-214 (G1), GAG 253-284 (G2) or V3 ENV 303-335 (E).

TABLE 15

Proliferative responses of the PBMC of the volunteers with lipopeptides NEF, GAG and ENV

| Volunteer[a] | Recovery period | Proliferation index[c] | | | | | | Proliferation induced by the culture medium[d] |
|---|---|---|---|---|---|---|---|---|
| | | N1 | N2 | N3 | G1 | G2 | E | |
| V4.6 | W0 | 1.3 | 1.0 | 1.0 | 1.3 | 1.0 | 1 | 871 (±25) |
| | W20 | 2.4 | 3.1 (±1) | 10 (±7) | 4.5 (±1.1) | 7.2 (±0.7) | 3.6 (±0.9) | 280 (±32) |
| V4.15 | W0 | 1.0 | 1.0 | 1.3 | 1.0 | 1.4 | 1.5 | 1657 (±182) |
| | W20 | 1.9 | 2.2 | 1.6 | 1.2 | 1.6 | 2.1 | 252 (±30) |
| V4.16 | W0 | 1.0 | 1.2 | 1.3 | 1.3 | 1.8 | 1.5 | 3830 (±232) |
| | W20 | 1.1 | 1.1 | 2.2 | 4.6 (±0.6) | 3.6 (±0.5) | 3.9 (±0.7) | 1000 (±168) |
| V4.17 | W0 | 2.5 | 1.3 | 1.4 | 1.9 | 2.0 | 2.3 | 5708 (±470) |
| | W20 | 1.5 | 1.1 | 1.6 | 2.0 | 2.0 | 2.8 | 1228 (±54) |
| V4.18 | W0 | 1.0 | 1.3 | 1.5 | 1.8 | 3.3 (±0.7) | 1.3 | 460 (±49) |
| | W20 | nd | nd | nd | nd | nd | nd | nd |
| V4.28 | W0 | 1.3 | 2.2 | 1.7 | 1.2 | 1.2 | 1.2 | 869 (±36) |
| | W20 | 3.8 (±0.6) | 1.2 | 21 (±2) | 1.2 | 8.2 (±1.6) | 7.6 (±2.2) | 2558 (±186) |
| V4.1 (QS21) | W0 | 1.0 | 1.1 | 1.0 | 1.1 | 1.0 | 1.0 | 3107 (±521) |
| | W20 | nd | nd | nd | nd | nd | nd | nd |
| V4.5 (QS21) | W0 | 1.5 | 1.6 | 1.5 | 1.6 | 1.5 | 1.3 | 341 (±20) |
| | W20 | 4.6 (±1.2) | 3.1 (±0.3) | 1.5 | 2.0 | 3.9 (±0.3) | 5.0 (±2.2) | 776 (±60) |
| V4.19 (QS21) | W0 | 1.0 | 1.1 | 1.2 | 1.1 | 1.0 | 1.0 | 918 (±102) |
| | W20 | 24.3 (±3.1) | 8.5 (±5) | 4.4 (±1.2) | 3.1 (±2.5) | 11.0 (±2.7) | 9.4 (±2.8) | 497 (±168) |
| V4.21 (QS21) | W0 | 1.3 | 1.3 | 1.2 | 3.9 (±1) | 1.3 | 1.4 | 322 (±21) |
| | W20 | 6.5 (±3) | 1.4 | 2.3 | 2.8 | 11.3 (±4) | 3.3 (±1.9) | 1052 (±82) |
| V4.32 (QS21) | W0 | 1.0 | 1.0 | 1.1 | 1.3 | 1.2 | 1.2 | 4448 (±75) |
| | W20 | 1.0 | 1.0 | 1.7 | 1.2 | 10.1 (±1.5) | 0.9 | 245 (±30) |
| V4.34 (QS21) | W0 | 1.0 | 1.1 | 1.1 | 1.2 | 1.2 | 1.2 | 5383 (±309) |
| | W20 | 3.4 (±0.2) | 1.1 | 3.3 (±0.1) | 2.2 | 4.4 (±0.6) | 3.1 (±0.1) | 7381 (±280) |

[a]The volunteers were immunized with six lipopeptides in the form of micelles, or with an adjuvant (QS21).
[b]The PBMC of the volunteers were recovered before injection of the lipopeptides (W0), and during the twentieth week (W20).
[c]$2 \times 10^5$ cells were cultivated with 1 µg/ml of the HIV lipopeptides and the proliferation was measured by incorporation of tritiated thymidine at day 6. The lipopeptides were N1, N2, N3, G1, G2, and E. The proliferation index obtained with the culture medium only was equal to 1.
[d]The proliferative response (cpm) of the PBMC of the volunteers cultivated in the medium alone is given. All the PBMC samples proliferated in response to 1 µg/ml of PHA, PPD and SEB.

TABLE 16

Specificity of the CTL in the immunized volunteers
% of specific lysis of the cells

| Lipopeptide incubated with target cells | V4.6[a] | | V4.16 | | V4.18 | | V4.28 | |
|---|---|---|---|---|---|---|---|---|
| | W0 | W20 | W0 | W20 | W0 | W20 | W0 | W20 |
| E/T Ratio | 70/1 | 70/1 | 50/1 | 50/1 | 80/1 | 80/1 | 10/1 | 10/1 |
| None | 5% | 11% | 2% | 12% | 8% | 14% | 5% | 8% |
| NEF 66-97 | 9% | 17% | 8% | 18% | 11% | 40% | 12% | 19% |
| NEF 117-147 | 9% | 16% | 2% | 13% | 6% | 6% | 19% | 12% |
| NEF 182-205 | 4% | 15% | 2% | 24% | 6% | 6% | 2% | 4% |
| E/T Ratio | 70/1 | 70/1 | 30/1 | 30/1 | 55/1 | 55/1 | 10/1 | 10/1 |
| None | 4% | 18% | 5% | 5% | 8% | 6% | 2% | 2% |
| GAG 183-214 | 7% | 14% | 9% | 10% | nd | nd | 2% | 2% |
| GAG 253-284 | 9% | 49% | 11% | 20% | 6% | 26% | 2% | 2% |

TABLE 16-continued

Specificity of the CTL in the immunized volunteers
% of specific lysis of the cells

| Lipopeptide incubated with | V4.5 (QS21) | | V4.19 (QS21) | | V4.21 (QS21) | | V4.34 (QS21) | |
|---|---|---|---|---|---|---|---|---|
| target cells | W0 | W20 | W0 | W20 | W0 | W20 | W0 | W20 |
| E/T Ratio | 100/1 | 100/1 | 60/1 | 60/1 | 40/1 | 40/1 | 35/1 | 35/1 |
| None | 16% | 31% | 2% | 6% | 2% | 2% | 10% | 2% |
| NEF 66-97 | 10% | 23% | 0% | 15% | 2% | 2% | 2% | 2% |
| NEF 117-147 | 18% | 47% | 2% | 27% | 2% | 2% | 2% | 2% |
| NEF 182-205 | 10% | 31% | 0% | 0% | 2% | 2% | 2% | 2% |
| E/T Ratio | 140/1 | 140/1 | 60/1 | 60/1 | 46/1 | 46/1 | 35/1 | 35/1 |
| None | 23% | 11% | 0% | 0% | 2% | 2% | 2% | 2% |
| GAG 183-214 | 21% | 11% | 0% | 0% | 2% | 2% | 2% | 23% |
| GAG 253-284 | 20% | 68% | 0% | 9% | 2% | 2% | 5% | 5% |

| Lipopeptide incubated with | V4.6ᵃ | | V4.16 | | V4.18 | | V4.28 | |
|---|---|---|---|---|---|---|---|---|
| target cells | W0 | W20 | W0 | W20 | W0 | W20 | W0 | W20 |
| E/T Ratio | 70/1 | 70/1 | 25/1 | 25/1 | | | 10/1 | 10/1 |
| None | 3% | 6% | 32% | 23% | nd | nd | 2% | 2% |
| V3 ENV 303-335 | 2% | 36% | 12% | 49% | nd | nd | 2% | 17% |
| E/T Ratio | | | 50/1 | 50/1 | | | 10/1 | 10/1 |
| None | | | 13% | 23% | | | 2% | 2% |
| anti-A1 | | | 2% | 48% | | | 5% | 34% |
| anti-A3 | | | nd | nd | | | nd | nd |

| Lipopeptide incubated with | V4.5 (QS21) | | V4.19 (QS21) | | V4.21 (QS21) | | V4.34 (QS21) | |
|---|---|---|---|---|---|---|---|---|
| target cells | W0 | W20 | W0 | W20 | W0 | W20 | W0 | W20 |
| E/T Ratio | 60/1 | 60/1 | 60/1 | 60/1 | 86/1 | 86/1 | 35/1 | 35/1 |
| None | 22% | 14% | 0% | 2% | 7% | 13% | 5% | 3% |
| V3 ENV 303-335 | 24% | 16% | 2% | 6% | 2% | 23% | 3% | 3% |
| E/T Ratio | | | | | | | 35/1 | 35/1 |
| None | | | | | | | 2% | 2% |
| anti-A1 | | | | | | | nd | nd |
| anti-A3 | | | | | | | 2% | 2% |

ᵃThe volunteers were immunized with six lipopeptides in the form of micelles, or with an adjuvant (QS21).
ᵇThe target cells were autologous PBMC sensitized with 10 μM of each of the lipopeptides, irradiated and marked with $^{51}$Cr.
ᶜThe chromium release assay was performed after three in vitro stimulations. The cytotoxic activity against autologous EBV cells incubated with the peptides or without peptides was measured in a release assay of 4 hours. The cytotoxic activity was considered as positive when the chromium release was 10% greater than that observed with the target cells alone. A1 and A3 correspond to EBV cells incubated with a group of peptides A1 (n 137-145, n 195-202, n 184-191, n 121-128 for V4.16 or n 183-191, n 121-128 for V4.28) and peptide A3 (n 73-82).
ᵈThe E/T ratio (ratio effector cells/target cells) corresponds to $5 \times 10^3$ marked target cells, incubated with varying quantities of effector cells.

TABLE 17

CD8⁺ T cells secreting γ-interferon/ex vivo assay
Number of cells secreting γ-interferon/1 × 10⁶ cells

| | | | V4.18 A2/11 B44/60 | | V4.5 (QS21) A2/11 B18/27 | | V4.21 (QS21) A1 B8 | |
|---|---|---|---|---|---|---|---|---|
| SEQ ID NO: | | | W0 | W20 | W0 | W20 | W0 | W20 |
| 131 | HLA-A1 | NEF 121-128 | | | | | 1 | 41 |
| 132 | | NEF 137-145 | | | | | 1 | 6 |
| 133 | | NEF 184-191 | | | | | 6 | 26 |
| 134 | | NEF 195-202 | | | | | 1 | 1 |
| 145 | HLA-A2 | NEF 136-145 | 0 | 0 | 0 | 4 | | |
| 147 | | NEF 190-198 | nd | nd | 4 | 16 | | |
| 149 | | GAG 183-191 | nd | nd | 2 | 16 | | |
| 174 | HLA-A11 | NEF 73-82ᶜ | 0 | 15 | 0 | 0 | | |
| 175 | | NEF 84-92 | 0 | 55 | nd | nd | | |
| | | EBN 416-424 | 500 | 500 | 66 | 63 | | |
| 200 | HLA-B8 | NEF 90-97 | | | | | 1 | 51 |
| 207 | | NEF 182-189 | | | | | 1 | 26 |
| 19 | HLA-B27 | NEF 134-141 | | | 2 | 14 | | |
| 10 | | GAG 263-272 | | | 0 | 9 | | |
| 214 | HLA-B18 | NEF 135-143 | | | 0 | 9 | | |

The invention claimed is:

1. A composition for inducing an immune response, comprising micelles or micro-aggregates wherein each micelle or micro-aggregate comprises:
   more than one first lipopeptide comprising at least one CTL antigenic determinant and at least one lipid unit, and
   a second lipopeptide comprising at least one helper T antigenic determinant and at least one lipid unit.

2. A composition according to claim 1 wherein the first and second lipopeptides each comprise one or more $C_4$-$C_{18}$ lipid units.

3. A composition according to claim 1 wherein the first and second lipopeptides each comprise one or two $C_4$-$C_{18}$ lipid chains linked by a covalent bond to one or two amino acids of the respective lipopeptide.

4. A composition according to claim 1 wherein the lipid units of the lipopeptides each comprise two palmitic acid chains linked to a lysine through an $NH_2$ group of said lysine.

5. A composition according to claim 1 wherein the lipid units of each lipopeptide comprises one or more of: a residue of palmitic acid, 2-aminohexadecanoic acid, oleic acid, linoleic acid, linolenic acid, pimelautide, trimexautide, or a derivative of cholesterol.

6. A composition according to claim 1 wherein the non-lipid part of the each of the first and second lipopeptides comprises between 10 and 100 amino acids.

7. A composition according to claim 1 wherein the helper T antigenic determinant is a multivalent antigenic determinant.

8. A composition according to claim 1, wherein the helper T antigenic determinant is the peptide 830-843 of the tetanus toxin with the following sequence:
   QYIKANSKFIGITE (SEQ ID NO: 1).

9. A composition according to claim 1 wherein the helper T antigenic determinant comprises the antigenic determinant of hemagglutinin or the PADRE antigenic determinant.

10. A composition according to claim 1 wherein the lipopeptides comprise at least one CTL antigenic determinant selected from the group consisting of a specific protein of melanoma, a protein from HIV, a protein from HBV, a protein from papillomavirus, protein p53 and a specific protein of *Plasmodium falciparum*.

11. A composition according to claim 1 wherein said micelles or micro-aggregates comprise one or more of the following lipopeptides:
   GAG 17 EKIRLRPGGKKKYKLKHIVK(Pam)-$NH_2$ (SEQ ID No: 31)
   GAG 253 NPPIPVGEIYKRWIILGLNKIVRMYSPT-SILDK(Pam)-$NH_2$ (SEQ ID No: 6)
   POL 325 AIFQSSMTKILEPFRKQNPDIVIYQYMD-DLYK(Pam)-$NH_2$ (SEQ ID No: 32)
   NEF 66 VGFPVTPQVPLRPMTYKAAVDLSH-FLKEKGGLK(Pam)-$NH_2$ (SEQ ID No: 2)
   NEF 116 HTQGYFPDWQNYTPGPGVRYPLTFGW-LYKLK(Pam)-$NH_2$ (SEQ ID No: 33)
   TT Ac-QYIKANSKFIGITELKKK(Pam)-$NH_2$ (SEQ ID No: 30).

12. A composition according to claim 1 wherein said micelles or micro-aggregates comprise one of more of the following lipopeptides:
   LSA3 CT 1 LLSNIEEPKENIIDNLLNNIK(Pam)-$NH_2$ (SEQ ID NO.34)
   LSA3 NRI Ac-DELFNELLNSVDVNGEVKENI-LEESQK(Pam)-$NH_2$ (SEQ ID NO. 35)
   LSA3 NRII Ac-LEESQVNDDIFNSLVKSVQQEQQH-NVK(Pam)-$NH_2$ (SEQ ID NO. 36)
   LSA3 RE K(Pam)VESVAPSVEESVAPSVEESVAEN-VEESVAENV-$NH_2$ (SEQ ID NO. 37).

13. A pharmaceutical composition comprising a pharmacologically effective dose of micelles or micro-aggregates according to claim 1 and a pharmaceutically compatible vehicle.

14. A method for producing micelles or micro-aggregates according to claim 1, comprising the following steps:
   dispersing each of the constituent lipopeptides in a solution of concentrated acetic acid of about 80% concentration then
   mixing the solutions thus obtained.

15. A method according to claim 14 wherein the dispersing of the lipopeptides dissolved in acetic acid is confirmed by a two-dimensional nuclear magnetic resonance method.

16. A method for inducing an immune response against a particular antigen in an individual comprising administering micelles or micro-aggregates according to claim 1 to the individual.

17. A composition according to claim 1, wherein the at least one lipid unit in the second lipopeptide is different from any lipid unit in the first lipopeptide.

18. A composition according to claim 6, wherein the non-lipid part of the lipopeptides, comprising the antigenic determinants, comprises between 10 and 50 amino acids.

19. A composition according to claim 1, wherein the helper T antigenic determinant is the peptide 830-843 of the tetanus toxin with the following sequence:
   QYIKANSKFIGITE (SEQ ID No: 1).

20. A method according to claim 16, wherein the antigen is an antigen from HIV, HBV, papillomavirus, melanoma, *Plasmodium falciparum*, or p53.

* * * * *

UNITED STATES PATENT AND TRADEMARK OFFICE
CERTIFICATE OF CORRECTION

PATENT NO.         : 7,476,386 B1
APPLICATION NO. : 09/555780
DATED              : January 13, 2009
INVENTOR(S)       : Gras-Masse et al.

It is certified that error appears in the above-identified patent and that said Letters Patent is hereby corrected as shown below:

IN THE PATENT:

Column 5, line 52:

Now reads:    "HLA ma be those"

Should read:  -- HLA may be those --

Column 15, line 58

Now reads:    "SEQ ID NO: 225"

Should read:  -- SEQ ID NO: 285 --

Column 16, line 67

Now reads:    "106 PBMC (responsive cells) with 106 irradiated stimulant"

Should read:  -- $10^6$ PBMC (responsive cells) with $10^6$ irradiated stimulant --

Column 18, line 27

Now reads:    "three to five times 1 greater"

Should read:  -- three to five times greater --

Signed and Sealed this

Eleventh Day of August, 2009

David J. Kappos
*Director of the United States Patent and Trademark Office*

SEQUENCE LISTING

<160> NUMBER OF SEQ ID NOS: 285

<210> SEQ ID NO 1
<211> LENGTH: 14
<212> TYPE: PRT
<213> ORGANISM: Clostridium tetani

<400> SEQUENCE: 1

```
Gln Tyr Ile Lys Ala Asn Ser Lys Phe Ile Gly Ile Thr Glu
  1               5                  10
```

<210> SEQ ID NO 2
<211> LENGTH: 33
<212> TYPE: PRT
<213> ORGANISM: Human immunodeficiency virus
<220> FEATURE:
<221> NAME/KEY: LIPID
<222> LOCATION: (33)
<223> OTHER INFORMATION: PALMITOYL DERIVATIVE

<400> SEQUENCE: 2

```
Val Gly Phe Pro Val Thr Pro Gln Val Pro Leu Arg Pro Met Thr Tyr
  1               5                  10                  15

Lys Ala Ala Val Asp Leu Ser His Phe Leu Lys Glu Lys Gly Gly Leu
             20                  25                  30

Lys
```

<210> SEQ ID NO 3
<211> LENGTH: 32
<212> TYPE: PRT
<213> ORGANISM: Human immunodeficiency virus
<220> FEATURE:
<221> NAME/KEY: LIPID
<222> LOCATION: (32)
<223> OTHER INFORMATION: PALMITOYL DERIVATIVE

<400> SEQUENCE: 3

```
Thr Gln Gly Tyr Phe Pro Asp Trp Gln Asn Tyr Thr Pro Gly Pro Gly
  1               5                  10                  15

Val Arg Tyr Pro Leu Thr Phe Gly Trp Cys Tyr Lys Leu Val Pro Lys
             20                  25                  30
```

<210> SEQ ID NO 4
<211> LENGTH: 25
<212> TYPE: PRT
<213> ORGANISM: Human immunodeficiency virus
<220> FEATURE:
<221> NAME/KEY: LIPID
<222> LOCATION: (25)
<223> OTHER INFORMATION: PALMITOYL DERIVATIVE

<400> SEQUENCE: 4

```
Glu Trp Arg Phe Asp Ser Arg Leu Ala Phe His His Val Ala Arg Glu
  1               5                  10                  15

Leu His Pro Glu Tyr Phe Lys Asn Lys
             20                  25
```

<210> SEQ ID NO 5
<211> LENGTH: 33
<212> TYPE: PRT
<213> ORGANISM: Human immunodeficiency virus
<220> FEATURE:
<221> NAME/KEY: LIPID
<222> LOCATION: (33)

```
<223> OTHER INFORMATION: PALMITOYL DERIVATIVE

<400> SEQUENCE: 5

Asp Leu Asn Thr Met Leu Asn Thr Val Gly Gly His Gln Ala Ala Met
 1               5                  10                  15

Gln Met Leu Lys Glu Thr Ile Asn Glu Glu Ala Ala Glu Trp Asp Arg
            20                  25                  30

Lys

<210> SEQ ID NO 6
<211> LENGTH: 33
<212> TYPE: PRT
<213> ORGANISM: Human immunodeficiency virus
<220> FEATURE:
<221> NAME/KEY: LIPID
<222> LOCATION: (33)
<223> OTHER INFORMATION: PALMITOYL DERIVATIVE

<400> SEQUENCE: 6

Asn Pro Pro Ile Pro Val Gly Glu Ile Tyr Lys Arg Trp Ile Ile Leu
 1               5                  10                  15

Gly Leu Asn Lys Ile Val Arg Met Tyr Ser Pro Thr Ser Ile Leu Asp
            20                  25                  30

Lys

<210> SEQ ID NO 7
<211> LENGTH: 34
<212> TYPE: PRT
<213> ORGANISM: Human immunodeficiency virus
<220> FEATURE:
<221> NAME/KEY: LIPID
<222> LOCATION: (34)
<223> OTHER INFORMATION: PALMITOYL DERIVATIVE

<400> SEQUENCE: 7

Thr Arg Pro Asn Asn Asn Thr Arg Lys Ser Ile His Ile Gly Pro Gly
 1               5                  10                  15

Arg Ala Phe Tyr Ala Thr Gly Glu Ile Ile Gly Asp Ile Arg Gln Ala
            20                  25                  30

His Lys

<210> SEQ ID NO 8
<211> LENGTH: 10
<212> TYPE: PRT
<213> ORGANISM: Human immunodeficiency virus

<400> SEQUENCE: 8

Arg Pro Asn Asn Asn Thr Arg Lys Ser Ile
 1               5                  10

<210> SEQ ID NO 9
<211> LENGTH: 9
<212> TYPE: PRT
<213> ORGANISM: Human immunodeficiency virus

<400> SEQUENCE: 9

Pro Pro Ile Pro Val Gly Glu Ile Tyr
 1               5

<210> SEQ ID NO 10
<211> LENGTH: 10
<212> TYPE: PRT
<213> ORGANISM: Human immunodeficiency virus
```

```
<400> SEQUENCE: 10

Lys Arg Trp Ile Ile Leu Gly Leu Asn Lys
1               5                   10

<210> SEQ ID NO 11
<211> LENGTH: 10
<212> TYPE: PRT
<213> ORGANISM: Human immunodeficiency virus

<400> SEQUENCE: 11

Leu Gly Leu Asn Lys Ile Val Arg Met Tyr
1               5                   10

<210> SEQ ID NO 12
<211> LENGTH: 10
<212> TYPE: PRT
<213> ORGANISM: Human immunodeficiency virus

<400> SEQUENCE: 12

Gln Val Pro Leu Arg Pro Met Thr Tyr Lys
1               5                   10

<210> SEQ ID NO 13
<211> LENGTH: 8
<212> TYPE: PRT
<213> ORGANISM: Human immunodeficiency virus

<400> SEQUENCE: 13

Val Pro Leu Arg Pro Met Thr Tyr
1               5

<210> SEQ ID NO 14
<211> LENGTH: 8
<212> TYPE: PRT
<213> ORGANISM: Human immunodeficiency virus

<400> SEQUENCE: 14

Ala Val Asp Leu Ser His Phe Leu
1               5

<210> SEQ ID NO 15
<211> LENGTH: 9
<212> TYPE: PRT
<213> ORGANISM: Human immunodeficiency virus

<400> SEQUENCE: 15

Ala Val Asp Leu Ser His Phe Leu Lys
1               5

<210> SEQ ID NO 16
<211> LENGTH: 11
<212> TYPE: PRT
<213> ORGANISM: Human immunodeficiency virus

<400> SEQUENCE: 16

Thr Gln Gly Tyr Phe Pro Asp Trp Gln Asn Tyr
1               5                   10

<210> SEQ ID NO 17
<211> LENGTH: 9
<212> TYPE: PRT
<213> ORGANISM: Human immunodeficiency virus

<400> SEQUENCE: 17
```

```
Tyr Phe Pro Asp Trp Gln Asn Tyr Thr
  1               5

<210> SEQ ID NO 18
<211> LENGTH: 10
<212> TYPE: PRT
<213> ORGANISM: Human immunodeficiency virus

<400> SEQUENCE: 18

Thr Pro Gly Pro Gly Val Arg Tyr Pro Leu
  1               5                  10

<210> SEQ ID NO 19
<211> LENGTH: 8
<212> TYPE: PRT
<213> ORGANISM: Human immunodeficiency virus

<400> SEQUENCE: 19

Arg Tyr Pro Leu Thr Phe Gly Trp
  1               5

<210> SEQ ID NO 20
<211> LENGTH: 8
<212> TYPE: PRT
<213> ORGANISM: Human immunodeficiency virus

<400> SEQUENCE: 20

Tyr Pro Leu Thr Phe Gly Trp Cys
  1               5

<210> SEQ ID NO 21
<211> LENGTH: 9
<212> TYPE: PRT
<213> ORGANISM: Human immunodeficiency virus

<400> SEQUENCE: 21

Ala Phe His His Val Ala Arg Glu Leu
  1               5

<210> SEQ ID NO 22
<211> LENGTH: 8
<212> TYPE: PRT
<213> ORGANISM: Human immunodeficiency virus

<400> SEQUENCE: 22

Phe Leu Lys Glu Lys Gly Gly Leu
  1               5

<210> SEQ ID NO 23
<211> LENGTH: 27
<212> TYPE: PRT
<213> ORGANISM: Simian immunodeficiency virus
<220> FEATURE:
<221> NAME/KEY: LIPID
<222> LOCATION: (27)
<223> OTHER INFORMATION: PALMITOYL DERIVATIVE

<400> SEQUENCE: 23

Ser Val Arg Pro Lys Val Pro Leu Arg Ala Met Thr Tyr Lys Leu Ala
  1               5                  10                  15

Ile Asp Met Ser His Phe Ile Lys Glu Lys Lys
             20                  25

<210> SEQ ID NO 24
```

```
<211> LENGTH: 24
<212> TYPE: PRT
<213> ORGANISM: Simian immunodeficiency virus
<220> FEATURE:
<221> NAME/KEY: LIPID
<222> LOCATION: (24)
<223> OTHER INFORMATION: PALMITOYL DERIVATIVE

<400> SEQUENCE: 24

Glu Lys Gly Gly Leu Glu Gly Ile Tyr Tyr Ser Ala Arg Arg His Arg
 1               5                  10                  15

Ile Leu Asp Met Tyr Leu Glu Lys
            20

<210> SEQ ID NO 25
<211> LENGTH: 25
<212> TYPE: PRT
<213> ORGANISM: Simian immunodeficiency virus
<220> FEATURE:
<221> NAME/KEY: LIPID
<222> LOCATION: (25)
<223> OTHER INFORMATION: PALMITOYL DERIVATIVE

<400> SEQUENCE: 25

Asp Trp Gln Asp Tyr Thr Ser Gly Pro Gly Ile Arg Tyr Pro Lys Thr
 1               5                  10                  15

Phe Gly Trp Leu Trp Lys Leu Val Lys
            20                  25

<210> SEQ ID NO 26
<211> LENGTH: 26
<212> TYPE: PRT
<213> ORGANISM: Simian immunodeficiency virus
<220> FEATURE:
<221> NAME/KEY: LIPID
<222> LOCATION: (26)
<223> OTHER INFORMATION: PALMITOYL DERIVATIVE

<400> SEQUENCE: 26

Ser Lys Trp Asp Asp Pro Trp Gly Glu Val Leu Ala Trp Lys Phe Asp
 1               5                  10                  15

Pro Thr Leu Ala Tyr Thr Tyr Glu Ala Lys
            20                  25

<210> SEQ ID NO 27
<211> LENGTH: 28
<212> TYPE: PRT
<213> ORGANISM: Simian immunodeficiency virus
<220> FEATURE:
<221> NAME/KEY: LIPID
<222> LOCATION: (28)
<223> OTHER INFORMATION: PALMITOYL DERIVATIVE

<400> SEQUENCE: 27

Tyr Thr Tyr Glu Ala Tyr Ala Arg Tyr Pro Glu Glu Leu Glu Ala Ser
 1               5                  10                  15

Gln Ala Cys Gln Arg Lys Arg Leu Glu Glu Gly Lys
            20                  25

<210> SEQ ID NO 28
<211> LENGTH: 32
<212> TYPE: PRT
<213> ORGANISM: Simian immunodeficiency virus
<220> FEATURE:
<221> NAME/KEY: LIPID
<222> LOCATION: (32)
<223> OTHER INFORMATION: PALMITOYL DERIVATIVE
```

```
<400> SEQUENCE: 28

Lys Phe Gly Ala Glu Val Val Pro Gly Phe Gln Ala Leu Ser Glu Gly
 1               5                  10                  15

Cys Thr Pro Tyr Asp Ile Asn Gln Met Leu Asn Cys Val Gly Asp Lys
                20                  25                  30

<210> SEQ ID NO 29
<211> LENGTH: 37
<212> TYPE: PRT
<213> ORGANISM: Simian immunodeficiency virus
<220> FEATURE:
<221> NAME/KEY: LIPID
<222> LOCATION: (37)
<223> OTHER INFORMATION: PALMITOYL DERIVATIVE

<400> SEQUENCE: 29

Gln Ile Gln Trp Met Tyr Arg Gln Gln Asn Pro Ile Val Gly Asn Ile
 1               5                  10                  15

Tyr Arg Arg Trp Ile Gln Leu Gly Leu Gln Lys Cys Val Arg Met Tyr
                20                  25                  30

Asn Pro Thr Asn Lys
            35

<210> SEQ ID NO 30
<211> LENGTH: 18
<212> TYPE: PRT
<213> ORGANISM: Simian immunodeficiency virus
<220> FEATURE:
<221> NAME/KEY: LIPID
<222> LOCATION: (18)
<223> OTHER INFORMATION: PALMITOYL DERIVATIVE
<221> NAME/KEY: MOD_RES
<222> LOCATION: (1)
<223> OTHER INFORMATION: ACETYLATION

<400> SEQUENCE: 30

Gln Tyr Ile Lys Ala Asn Ser Lys Phe Ile Gly Ile Thr Glu Leu Lys
 1               5                  10                  15

Lys Lys

<210> SEQ ID NO 31
<211> LENGTH: 20
<212> TYPE: PRT
<213> ORGANISM: Human immunodeficiency virus
<220> FEATURE:
<221> NAME/KEY: LIPID
<222> LOCATION: (20)
<223> OTHER INFORMATION: PALMITOYL DERIVATIVE

<400> SEQUENCE: 31

Glu Lys Ile Arg Leu Arg Pro Gly Gly Lys Lys Lys Tyr Lys Leu Lys
 1               5                  10                  15

His Ile Val Lys
            20

<210> SEQ ID NO 32
<211> LENGTH: 32
<212> TYPE: PRT
<213> ORGANISM: Human immunodeficiency virus
<220> FEATURE:
<221> NAME/KEY: LIPID
<222> LOCATION: (32)
<223> OTHER INFORMATION: PALMITOYL DERIVATIVE

<400> SEQUENCE: 32
```

```
Ala Ile Phe Gln Ser Ser Met Thr Lys Ile Leu Glu Pro Phe Arg Lys
 1               5                  10                  15

Gln Asn Pro Asp Ile Val Ile Tyr Gln Tyr Met Asp Asp Leu Tyr Lys
             20                  25                  30
```

<210> SEQ ID NO 33
<211> LENGTH: 31
<212> TYPE: PRT
<213> ORGANISM: Human immunodeficiency virus
<220> FEATURE:
<221> NAME/KEY: LIPID
<222> LOCATION: (31)
<223> OTHER INFORMATION: PALMITOYL DERIVATIVE

<400> SEQUENCE: 33

```
His Thr Gln Gly Tyr Phe Pro Asp Trp Gln Asn Tyr Thr Pro Gly Pro
 1               5                  10                  15

Gly Val Arg Tyr Pro Leu Thr Phe Gly Trp Leu Tyr Lys Leu Lys
             20                  25                  30
```

<210> SEQ ID NO 34
<211> LENGTH: 21
<212> TYPE: PRT
<213> ORGANISM: Plasmodium falciparum
<220> FEATURE:
<221> NAME/KEY: LIPID
<222> LOCATION: (21)
<223> OTHER INFORMATION: PALMITOYL DERIVATIVE

<400> SEQUENCE: 34

```
Leu Leu Ser Asn Ile Glu Glu Pro Lys Glu Asn Ile Ile Asp Asn Leu
 1               5                  10                  15

Leu Asn Asn Ile Lys
             20
```

<210> SEQ ID NO 35
<211> LENGTH: 27
<212> TYPE: PRT
<213> ORGANISM: Plasmodium falciparum
<220> FEATURE:
<221> NAME/KEY: LIPID
<222> LOCATION: (27)
<223> OTHER INFORMATION: PALMITOYL DERIVATIVE
<221> NAME/KEY: MOD_RES
<222> LOCATION: (1)
<223> OTHER INFORMATION: ACETYLATION

<400> SEQUENCE: 35

```
Asp Glu Leu Phe Asn Glu Leu Leu Asn Ser Val Asp Val Asn Gly Glu
 1               5                  10                  15

Val Lys Glu Asn Ile Leu Glu Glu Ser Gln Lys
             20                  25
```

<210> SEQ ID NO 36
<211> LENGTH: 27
<212> TYPE: PRT
<213> ORGANISM: Plasmodium falciparum
<220> FEATURE:
<221> NAME/KEY: LIPID
<222> LOCATION: (27)
<223> OTHER INFORMATION: PALMITOYL DERIVATIVE
<221> NAME/KEY: MOD_RES
<222> LOCATION: (1)
<223> OTHER INFORMATION: ACETYLATION

<400> SEQUENCE: 36

-continued

```
Leu Glu Glu Ser Gln Val Asn Asp Asp Ile Phe Asn Ser Leu Val Lys
 1               5                  10                  15

Ser Val Gln Gln Glu Gln Gln His Asn Val Lys
                20                  25

<210> SEQ ID NO 37
<211> LENGTH: 33
<212> TYPE: PRT
<213> ORGANISM: Plasmodium falciparum
<220> FEATURE:
<221> NAME/KEY: LIPID
<222> LOCATION: (1)
<223> OTHER INFORMATION: PALMITOYL DERIVATIVE

<400> SEQUENCE: 37

Lys Val Glu Ser Val Ala Pro Ser Val Glu Glu Ser Val Ala Pro Ser
 1               5                  10                  15

Val Glu Glu Ser Val Ala Glu Asn Val Glu Glu Ser Val Ala Glu Asn
                20                  25                  30

Val

<210> SEQ ID NO 38
<211> LENGTH: 9
<212> TYPE: PRT
<213> ORGANISM: Homo sapiens

<400> SEQUENCE: 38

Glu Asp Ala Glu Leu Asn Pro Arg Phe
 1               5

<210> SEQ ID NO 39
<211> LENGTH: 9
<212> TYPE: PRT
<213> ORGANISM: Homo sapiens

<400> SEQUENCE: 39

Ser Glu Leu Asp Leu Glu Lys Gly Leu
 1               5

<210> SEQ ID NO 40
<211> LENGTH: 9
<212> TYPE: PRT
<213> ORGANISM: Homo sapiens

<400> SEQUENCE: 40

Asp Glu Leu Glu Ala Val Pro Asn Ile
 1               5

<210> SEQ ID NO 41
<211> LENGTH: 9
<212> TYPE: PRT
<213> ORGANISM: Homo sapiens

<400> SEQUENCE: 41

Lys Glu Asp Ala Leu Gln Arg Pro Val
 1               5

<210> SEQ ID NO 42
<211> LENGTH: 9
<212> TYPE: PRT
<213> ORGANISM: Homo sapiens

<400> SEQUENCE: 42

Glu Asp Ala Leu Gln Arg Pro Val Ala
```

-continued

```
<210> SEQ ID NO 43
<211> LENGTH: 9
<212> TYPE: PRT
<213> ORGANISM: Homo sapiens

<400> SEQUENCE: 43

Gly Glu Lys Leu Arg Val Leu Gly Tyr
 1               5

<210> SEQ ID NO 44
<211> LENGTH: 9
<212> TYPE: PRT
<213> ORGANISM: Homo sapiens

<400> SEQUENCE: 44

Glu Asp Thr Met Glu Val Glu Glu Phe
 1               5

<210> SEQ ID NO 45
<211> LENGTH: 9
<212> TYPE: PRT
<213> ORGANISM: Homo sapiens

<400> SEQUENCE: 45

Met Glu Tyr Leu Glu Lys Lys Asn Phe
 1               5

<210> SEQ ID NO 46
<211> LENGTH: 9
<212> TYPE: PRT
<213> ORGANISM: Homo sapiens

<400> SEQUENCE: 46

Asn Glu Glu Ala Ala Asp Glu Val Phe
 1               5

<210> SEQ ID NO 47
<211> LENGTH: 9
<212> TYPE: PRT
<213> ORGANISM: Homo sapiens

<400> SEQUENCE: 47

Val Asn Gln Glu Arg Phe Arg Met Ile
 1               5

<210> SEQ ID NO 48
<211> LENGTH: 9
<212> TYPE: PRT
<213> ORGANISM: Homo sapiens

<400> SEQUENCE: 48

Leu Phe Gln Lys Leu Ala Ser Gln Leu
 1               5

<210> SEQ ID NO 49
<211> LENGTH: 9
<212> TYPE: PRT
<213> ORGANISM: Homo sapiens

<400> SEQUENCE: 49

Ala Arg Lys Leu Arg His Val Phe Leu
 1               5
```

```
<210> SEQ ID NO 50
<211> LENGTH: 9
<212> TYPE: PRT
<213> ORGANISM: Homo sapiens

<400> SEQUENCE: 50

Ala Leu Lys Ile Lys Ile Ser Gln Ile
 1               5

<210> SEQ ID NO 51
<211> LENGTH: 8
<212> TYPE: PRT
<213> ORGANISM: Homo sapiens

<400> SEQUENCE: 51

Cys Val Lys Leu Gln Thr Val His
 1               5

<210> SEQ ID NO 52
<211> LENGTH: 9
<212> TYPE: PRT
<213> ORGANISM: Homo sapiens

<400> SEQUENCE: 52

Lys Ala Leu Gln Arg Pro Val Ala Ser
 1               5

<210> SEQ ID NO 53
<211> LENGTH: 9
<212> TYPE: PRT
<213> ORGANISM: Homo sapiens

<400> SEQUENCE: 53

Gly Ala Lys Thr Lys Ala Thr Ser Leu
 1               5

<210> SEQ ID NO 54
<211> LENGTH: 9
<212> TYPE: PRT
<213> ORGANISM: Homo sapiens

<400> SEQUENCE: 54

Ile Gln Gln Met Arg Asn Lys Phe Ala
 1               5

<210> SEQ ID NO 55
<211> LENGTH: 8
<212> TYPE: PRT
<213> ORGANISM: Homo sapiens

<400> SEQUENCE: 55

Gln Met Arg Asn Lys Phe Ala Phe
 1               5

<210> SEQ ID NO 56
<211> LENGTH: 9
<212> TYPE: PRT
<213> ORGANISM: Homo sapiens

<400> SEQUENCE: 56

Asn Pro Arg Phe Leu Lys Asp Asn Leu
 1               5

<210> SEQ ID NO 57
```

```
<211> LENGTH: 10
<212> TYPE: PRT
<213> ORGANISM: Homo sapiens

<400> SEQUENCE: 57

Thr Pro Asp Cys Ser Ser Asn Glu Asn Leu
 1               5                  10

<210> SEQ ID NO 58
<211> LENGTH: 9
<212> TYPE: PRT
<213> ORGANISM: Homo sapiens

<400> SEQUENCE: 58

Thr Pro Arg Arg Gln Ser Met Thr Val
 1               5

<210> SEQ ID NO 59
<211> LENGTH: 9
<212> TYPE: PRT
<213> ORGANISM: Homo sapiens

<400> SEQUENCE: 59

Ser Pro Gly Gln Arg Ser Ile Ser Leu
 1               5

<210> SEQ ID NO 60
<211> LENGTH: 10
<212> TYPE: PRT
<213> ORGANISM: Homo sapiens

<400> SEQUENCE: 60

His Pro Asn Leu Val Gln Leu Leu Gly Val
 1               5                  10

<210> SEQ ID NO 61
<211> LENGTH: 10
<212> TYPE: PRT
<213> ORGANISM: Homo sapiens

<400> SEQUENCE: 61

Ser Pro Lys Pro Ser Asn Gly Ala Gly Val
 1               5                  10

<210> SEQ ID NO 62
<211> LENGTH: 9
<212> TYPE: PRT
<213> ORGANISM: Homo sapiens

<400> SEQUENCE: 62

Lys Pro Leu Arg Arg Gln Val Thr Val
 1               5

<210> SEQ ID NO 63
<211> LENGTH: 9
<212> TYPE: PRT
<213> ORGANISM: Homo sapiens

<400> SEQUENCE: 63

Ser Pro Ala Pro Val Pro Ser Thr Leu
 1               5

<210> SEQ ID NO 64
<211> LENGTH: 9
<212> TYPE: PRT
```

-continued

<213> ORGANISM: Homo sapiens

<400> SEQUENCE: 64

Glu Arg Cys Lys Ala Ser Ile Arg Arg
 1               5

<210> SEQ ID NO 65
<211> LENGTH: 10
<212> TYPE: PRT
<213> ORGANISM: Homo sapiens

<400> SEQUENCE: 65

Asp Arg Gln Arg Trp Gly Phe Phe Arg Arg
 1               5                  10

<210> SEQ ID NO 66
<211> LENGTH: 9
<212> TYPE: PRT
<213> ORGANISM: Homo sapiens

<400> SEQUENCE: 66

Gln Arg Val Gly Asp Leu Phe Gln Lys
 1               5

<210> SEQ ID NO 67
<211> LENGTH: 9
<212> TYPE: PRT
<213> ORGANISM: Homo sapiens

<400> SEQUENCE: 67

Phe Arg Val His Ser Arg Asn Gly Lys
 1               5

<210> SEQ ID NO 68
<211> LENGTH: 9
<212> TYPE: PRT
<213> ORGANISM: Homo sapiens

<400> SEQUENCE: 68

Leu Leu Tyr Lys Pro Val Asp Arg Val
 1               5

<210> SEQ ID NO 69
<211> LENGTH: 9
<212> TYPE: PRT
<213> ORGANISM: Homo sapiens

<400> SEQUENCE: 69

Phe Leu Ser Ser Ile Asn Glu Glu Ile
 1               5

<210> SEQ ID NO 70
<211> LENGTH: 9
<212> TYPE: PRT
<213> ORGANISM: Homo sapiens

<400> SEQUENCE: 70

Gln Leu Leu Lys Asp Ser Phe Met Val
 1               5

<210> SEQ ID NO 71
<211> LENGTH: 9
<212> TYPE: PRT
<213> ORGANISM: Homo sapiens

```
<400> SEQUENCE: 71

Phe Met Val Glu Leu Val Glu Gly Ala
 1               5

<210> SEQ ID NO 72
<211> LENGTH: 9
<212> TYPE: PRT
<213> ORGANISM: Homo sapiens

<400> SEQUENCE: 72

Lys Leu Ser Glu Gln Glu Ser Leu Leu
 1               5

<210> SEQ ID NO 73
<211> LENGTH: 9
<212> TYPE: PRT
<213> ORGANISM: Homo sapiens

<400> SEQUENCE: 73

Met Leu Thr Asn Ser Cys Val Lys Leu
 1               5

<210> SEQ ID NO 74
<211> LENGTH: 10
<212> TYPE: PRT
<213> ORGANISM: Homo sapiens

<400> SEQUENCE: 74

Gly Leu Tyr Gly Phe Leu Asn Val Ile Val
 1               5                  10

<210> SEQ ID NO 75
<211> LENGTH: 9
<212> TYPE: PRT
<213> ORGANISM: Homo sapiens

<400> SEQUENCE: 75

Phe Leu Asn Val Ile Val His Ser Ala
 1               5

<210> SEQ ID NO 76
<211> LENGTH: 9
<212> TYPE: PRT
<213> ORGANISM: Homo sapiens

<400> SEQUENCE: 76

Val Leu Leu Tyr Met Ala Thr Gln Ile
 1               5

<210> SEQ ID NO 77
<211> LENGTH: 9
<212> TYPE: PRT
<213> ORGANISM: Homo sapiens

<400> SEQUENCE: 77

Phe Ile Pro Leu Ile Ser Thr Arg Val
 1               5

<210> SEQ ID NO 78
<211> LENGTH: 9
<212> TYPE: PRT
<213> ORGANISM: Homo sapiens

<400> SEQUENCE: 78
```

Val Val Leu Asp Ser Thr Glu Ala Leu
1               5

<210> SEQ ID NO 79
<211> LENGTH: 9
<212> TYPE: PRT
<213> ORGANISM: Homo sapiens

<400> SEQUENCE: 79

Asn Gln Glu Arg Phe Arg Met Ile Tyr
1               5

<210> SEQ ID NO 80
<211> LENGTH: 9
<212> TYPE: PRT
<213> ORGANISM: Homo sapiens

<400> SEQUENCE: 80

Val Gly Asp Ala Ser Arg Pro Pro Tyr
1               5

<210> SEQ ID NO 81
<211> LENGTH: 10
<212> TYPE: PRT
<213> ORGANISM: Homo sapiens

<400> SEQUENCE: 81

Lys Val Pro Glu Leu Tyr Glu Ile His Lys
1               5                   10

<210> SEQ ID NO 82
<211> LENGTH: 9
<212> TYPE: PRT
<213> ORGANISM: Homo sapiens

<400> SEQUENCE: 82

Lys Leu Ala Ser Gln Leu Gly Val Tyr
1               5

<210> SEQ ID NO 83
<211> LENGTH: 10
<212> TYPE: PRT
<213> ORGANISM: Homo sapiens

<400> SEQUENCE: 83

Met Val Glu Leu Val Glu Gly Ala Arg Lys
1               5                   10

<210> SEQ ID NO 84
<211> LENGTH: 9
<212> TYPE: PRT
<213> ORGANISM: Homo sapiens

<400> SEQUENCE: 84

Ile Val His Ser Ala Thr Gly Phe Lys
1               5

<210> SEQ ID NO 85
<211> LENGTH: 9
<212> TYPE: PRT
<213> ORGANISM: Homo sapiens

<400> SEQUENCE: 85

Ala Thr Gly Phe Lys Gln Ser Ser Lys
1               5

```
<210> SEQ ID NO 86
<211> LENGTH: 9
<212> TYPE: PRT
<213> ORGANISM: Homo sapiens

<400> SEQUENCE: 86

Lys Gln Ser Ser Lys Ala Leu Gln Arg
  1               5

<210> SEQ ID NO 87
<211> LENGTH: 10
<212> TYPE: PRT
<213> ORGANISM: Homo sapiens

<400> SEQUENCE: 87

Glu Val Tyr Glu Gly Val Trp Lys Lys Tyr
  1               5                  10

<210> SEQ ID NO 88
<211> LENGTH: 10
<212> TYPE: PRT
<213> ORGANISM: Homo sapiens

<400> SEQUENCE: 88

Ser Leu Ala Tyr Asn Lys Phe Ser Ile Lys
  1               5                  10

<210> SEQ ID NO 89
<211> LENGTH: 9
<212> TYPE: PRT
<213> ORGANISM: Homo sapiens

<400> SEQUENCE: 89

Asn Leu Phe Ser Ala Leu Ile Lys Lys
  1               5

<210> SEQ ID NO 90
<211> LENGTH: 11
<212> TYPE: PRT
<213> ORGANISM: Homo sapiens

<400> SEQUENCE: 90

Thr Val Ala Pro Ala Ser Gly Leu Pro His Lys
  1               5                  10

<210> SEQ ID NO 91
<211> LENGTH: 10
<212> TYPE: PRT
<213> ORGANISM: Homo sapiens

<400> SEQUENCE: 91

Leu Ile Ser Thr Arg Val Ser Leu Arg Lys
  1               5                  10

<210> SEQ ID NO 92
<211> LENGTH: 9
<212> TYPE: PRT
<213> ORGANISM: Homo sapiens

<400> SEQUENCE: 92

Arg Ile Ala Ser Gly Ala Ile Thr Lys
  1               5
```

<210> SEQ ID NO 93
<211> LENGTH: 13
<212> TYPE: PRT
<213> ORGANISM: Homo sapiens

<400> SEQUENCE: 93

Lys Gln Ser Ser Lys Ala Leu Gln Arg Pro Val Ala Ser
 1               5                  10

<210> SEQ ID NO 94
<211> LENGTH: 11
<212> TYPE: PRT
<213> ORGANISM: Homo sapiens

<400> SEQUENCE: 94

Arg Val Glu Gly Asn Leu Ala Arg Val Glu Tyr
 1               5                  10

<210> SEQ ID NO 95
<211> LENGTH: 9
<212> TYPE: PRT
<213> ORGANISM: Homo sapiens

<400> SEQUENCE: 95

Gly Ser Asp Cys Thr Thr Ile His Tyr
 1               5

<210> SEQ ID NO 96
<211> LENGTH: 11
<212> TYPE: PRT
<213> ORGANISM: Homo sapiens

<400> SEQUENCE: 96

Leu Leu Pro Glu Asn Asn Val Leu Ser Pro Leu
 1               5                  10

<210> SEQ ID NO 97
<211> LENGTH: 9
<212> TYPE: PRT
<213> ORGANISM: Homo sapiens

<400> SEQUENCE: 97

Arg Met Pro Glu Ala Ala Pro Pro Val
 1               5

<210> SEQ ID NO 98
<211> LENGTH: 9
<212> TYPE: PRT
<213> ORGANISM: Homo sapiens

<400> SEQUENCE: 98

Arg Met Pro Glu Ala Ala Pro Arg Val
 1               5

<210> SEQ ID NO 99
<211> LENGTH: 9
<212> TYPE: PRT
<213> ORGANISM: Homo sapiens

<400> SEQUENCE: 99

Ala Leu Asn Lys Met Phe Cys Gln Leu
 1               5

<210> SEQ ID NO 100
<211> LENGTH: 9

<212> TYPE: PRT
<213> ORGANISM: Homo sapiens

<400> SEQUENCE: 100

Ser Thr Pro Pro Gly Thr Arg Val
 1               5

<210> SEQ ID NO 101
<211> LENGTH: 11
<212> TYPE: PRT
<213> ORGANISM: Homo sapiens

<400> SEQUENCE: 101

Gly Leu Ala Pro Pro Gln His Leu Ile Arg Val
 1               5                  10

<210> SEQ ID NO 102
<211> LENGTH: 9
<212> TYPE: PRT
<213> ORGANISM: Homo sapiens

<400> SEQUENCE: 102

Leu Leu Gly Arg Asn Ser Phe Glu Val
 1               5

<210> SEQ ID NO 103
<211> LENGTH: 9
<212> TYPE: PRT
<213> ORGANISM: Homo sapiens

<400> SEQUENCE: 103

Pro Leu Asp Gly Glu Tyr Phe Thr Leu
 1               5

<210> SEQ ID NO 104
<211> LENGTH: 9
<212> TYPE: PRT
<213> ORGANISM: Homo sapiens

<400> SEQUENCE: 104

Arg Val Arg Ala Met Ala Ile Tyr Lys
 1               5

<210> SEQ ID NO 105
<211> LENGTH: 9
<212> TYPE: PRT
<213> ORGANISM: Homo sapiens

<400> SEQUENCE: 105

Arg Arg Thr Glu Glu Glu Asn Leu Arg
 1               5

<210> SEQ ID NO 106
<211> LENGTH: 9
<212> TYPE: PRT
<213> ORGANISM: Homo sapiens

<400> SEQUENCE: 106

Glu Leu Pro Pro Gly Ser Thr Lys Arg
 1               5

<210> SEQ ID NO 107
<211> LENGTH: 10
<212> TYPE: PRT
<213> ORGANISM: Homo sapiens -continued

<400> SEQUENCE: 107

Leu Pro Glu Asn Asn Val Leu Ser Pro Leu
 1               5                   10

<210> SEQ ID NO 108
<211> LENGTH: 11
<212> TYPE: PRT
<213> ORGANISM: Homo sapiens

<400> SEQUENCE: 108

Ala Pro Arg Met Pro Glu Ala Ala Pro Pro Val
 1               5                   10

<210> SEQ ID NO 109
<211> LENGTH: 11
<212> TYPE: PRT
<213> ORGANISM: Homo sapiens

<400> SEQUENCE: 109

Ala Pro Arg Met Pro Glu Ala Ala Pro Arg Val
 1               5                   10

<210> SEQ ID NO 110
<211> LENGTH: 9
<212> TYPE: PRT
<213> ORGANISM: Homo sapiens

<400> SEQUENCE: 110

Ala Pro Pro Gln His Leu Ile Arg Val
 1               5

<210> SEQ ID NO 111
<211> LENGTH: 9
<212> TYPE: PRT
<213> ORGANISM: Homo sapiens

<400> SEQUENCE: 111

Arg Pro Ile Leu Thr Ile Ile Thr Leu
 1               5

<210> SEQ ID NO 112
<211> LENGTH: 11
<212> TYPE: PRT
<213> ORGANISM: Homo sapiens

<400> SEQUENCE: 112

Lys Pro Leu Asp Gly Glu Thr Tyr Phe Thr Leu
 1               5                   10

<210> SEQ ID NO 113
<211> LENGTH: 9
<212> TYPE: PRT
<213> ORGANISM: Homo sapiens

<400> SEQUENCE: 113

Cys Gln Leu Ala Lys Thr Cys Pro Val
 1               5

<210> SEQ ID NO 114
<211> LENGTH: 9
<212> TYPE: PRT
<213> ORGANISM: Homo sapiens

<400> SEQUENCE: 114

```
Gly Leu Ala Pro Pro Gln His Leu Ile
  1               5
```

<210> SEQ ID NO 115
<211> LENGTH: 9
<212> TYPE: PRT
<213> ORGANISM: Homo sapiens

<400> SEQUENCE: 115

```
Asn Thr Phe Arg His Ser Val Val Val
  1               5
```

<210> SEQ ID NO 116
<211> LENGTH: 11
<212> TYPE: PRT
<213> ORGANISM: Homo sapiens

<400> SEQUENCE: 116

```
Leu Leu Pro Glu Asn Asn Val Leu Ser Pro Leu
  1               5                  10
```

<210> SEQ ID NO 117
<211> LENGTH: 9
<212> TYPE: PRT
<213> ORGANISM: Homo sapiens

<400> SEQUENCE: 117

```
Arg Met Pro Glu Ala Ala Pro Pro Val
  1               5
```

<210> SEQ ID NO 118
<211> LENGTH: 10
<212> TYPE: PRT
<213> ORGANISM: Homo sapiens

<400> SEQUENCE: 118

```
Leu Ile Arg Val Glu Gly Asn Leu Arg Val
  1               5                  10
```

<210> SEQ ID NO 119
<211> LENGTH: 10
<212> TYPE: PRT
<213> ORGANISM: Human papillomavirus

<400> SEQUENCE: 119

```
Tyr Met Leu Asp Leu Gln Pro Glu Thr Thr
  1               5                  10
```

<210> SEQ ID NO 120
<211> LENGTH: 9
<212> TYPE: PRT
<213> ORGANISM: Human papillomavirus

<400> SEQUENCE: 120

```
Leu Leu Met Gly Thr Leu Gly Ile Val
  1               5
```

<210> SEQ ID NO 121
<211> LENGTH: 8
<212> TYPE: PRT
<213> ORGANISM: Human papillomavirus

<400> SEQUENCE: 121

```
Thr Leu Gly Ile Val Cys Pro Ile
```

```
<210> SEQ ID NO 122
<211> LENGTH: 10
<212> TYPE: PRT
<213> ORGANISM: Human papillomavirus

<400> SEQUENCE: 122

Thr Ile His Asp Ile Ile Leu Glu Cys Val
 1               5                  10

<210> SEQ ID NO 123
<211> LENGTH: 9
<212> TYPE: PRT
<213> ORGANISM: Human papillomavirus

<400> SEQUENCE: 123

Lys Leu Pro Gln Leu Cys Thr Glu Leu
 1               5

<210> SEQ ID NO 124
<211> LENGTH: 8
<212> TYPE: PRT
<213> ORGANISM: Human papillomavirus

<400> SEQUENCE: 124

Arg Pro Pro Lys Leu Pro Gln Leu
 1               5

<210> SEQ ID NO 125
<211> LENGTH: 23
<212> TYPE: PRT
<213> ORGANISM: Human papillomavirus

<400> SEQUENCE: 125

Leu Arg Arg Glu Val Tyr Asp Phe Ala Phe Arg Asp Leu Cys Ile Val
 1               5                  10                  15

Tyr Arg Asp Gly Asn Pro Tyr
            20

<210> SEQ ID NO 126
<211> LENGTH: 9
<212> TYPE: PRT
<213> ORGANISM: Human papillomavirus

<400> SEQUENCE: 126

Ile Ser Glu Tyr Arg His Tyr Cys Tyr
 1               5

<210> SEQ ID NO 127
<211> LENGTH: 20
<212> TYPE: PRT
<213> ORGANISM: Human papillomavirus

<400> SEQUENCE: 127

Glu Lys Gln Arg His Leu Asp Lys Lys Gln Arg Phe His Asn Ile Arg
 1               5                  10                  15

Gly Arg Trp Thr
            20

<210> SEQ ID NO 128
<211> LENGTH: 9
<212> TYPE: PRT
<213> ORGANISM: Human papillomavirus
```

<400> SEQUENCE: 128

Gln Ala Glu Pro Asp Arg Ala His Tyr
 1               5

<210> SEQ ID NO 129
<211> LENGTH: 10
<212> TYPE: PRT
<213> ORGANISM: Human papillomavirus

<400> SEQUENCE: 129

Glu Pro Asp Arg Ala His Tyr Asn Ile Val
 1               5                  10

<210> SEQ ID NO 130
<211> LENGTH: 11
<212> TYPE: PRT
<213> ORGANISM: Human immunodeficiency virus type 1

<400> SEQUENCE: 130

Gly Leu Glu Gly Leu Ile His Ser Gln Arg Arg
 1               5                  10

<210> SEQ ID NO 131
<211> LENGTH: 8
<212> TYPE: PRT
<213> ORGANISM: Human immunodeficiency virus type 1

<400> SEQUENCE: 131

Phe Pro Asp Trp Gln Asn Tyr Thr
 1               5

<210> SEQ ID NO 132
<211> LENGTH: 9
<212> TYPE: PRT
<213> ORGANISM: Human immunodeficiency virus type 1

<400> SEQUENCE: 132

Leu Thr Phe Gly Trp Cys Tyr Lys Leu
 1               5

<210> SEQ ID NO 133
<211> LENGTH: 8
<212> TYPE: PRT
<213> ORGANISM: Human immunodeficiency virus type 1

<400> SEQUENCE: 133

Arg Phe Asp Ser Arg Leu Ala Phe
 1               5

<210> SEQ ID NO 134
<211> LENGTH: 8
<212> TYPE: PRT
<213> ORGANISM: Human immunodeficiency virus type 1

<400> SEQUENCE: 134

Ala Arg Glu Leu His Pro Glu Tyr
 1               5

<210> SEQ ID NO 135
<211> LENGTH: 9
<212> TYPE: PRT
<213> ORGANISM: Human immunodeficiency virus type 1

<400> SEQUENCE: 135

```
Lys Leu Thr Pro Leu Cys Val Thr Leu
 1               5

<210> SEQ ID NO 136
<211> LENGTH: 9
<212> TYPE: PRT
<213> ORGANISM: Human immunodeficiency virus type 1

<400> SEQUENCE: 136

Ser Leu Tyr Asn Thr Val Ala Thr Leu
 1               5

<210> SEQ ID NO 137
<211> LENGTH: 9
<212> TYPE: PRT
<213> ORGANISM: Human immunodeficiency virus type 1

<400> SEQUENCE: 137

Ala Leu Val Glu Ile Cys Thr Glu Met
 1               5

<210> SEQ ID NO 138
<211> LENGTH: 11
<212> TYPE: PRT
<213> ORGANISM: Human immunodeficiency virus type 1

<400> SEQUENCE: 138

Val Leu Asp Val Gly Asp Ala Tyr Phe Ser Val
 1               5                   10

<210> SEQ ID NO 139
<211> LENGTH: 9
<212> TYPE: PRT
<213> ORGANISM: Human immunodeficiency virus type 1

<400> SEQUENCE: 139

Lys Ile Tyr Gln Tyr Met Asp Asp Leu
 1               5

<210> SEQ ID NO 140
<211> LENGTH: 9
<212> TYPE: PRT
<213> ORGANISM: Human immunodeficiency virus type 1

<400> SEQUENCE: 140

Lys Ile Glu Glu Leu Arg Gln His Leu
 1               5

<210> SEQ ID NO 141
<211> LENGTH: 11
<212> TYPE: PRT
<213> ORGANISM: Human immunodeficiency virus type 1

<400> SEQUENCE: 141

Leu Leu Arg Trp Gly Leu Thr Thr Pro Asp Lys
 1               5                   10

<210> SEQ ID NO 142
<211> LENGTH: 9
<212> TYPE: PRT
<213> ORGANISM: Human immunodeficiency virus type 1

<400> SEQUENCE: 142

Ile Leu Lys Glu Pro Val His Gly Val
```

-continued

```
                1               5

<210> SEQ ID NO 143
<211> LENGTH: 9
<212> TYPE: PRT
<213> ORGANISM: Human immunodeficiency virus type 1

<400> SEQUENCE: 143

Pro Leu Val Lys Leu Trp Tyr Gln Leu
                1               5

<210> SEQ ID NO 144
<211> LENGTH: 10
<212> TYPE: PRT
<213> ORGANISM: Human immunodeficiency virus type 1

<400> SEQUENCE: 144

Glu Leu Val Asn Gln Ile Ile Glu Gln Leu
                1               5                   10

<210> SEQ ID NO 145
<211> LENGTH: 10
<212> TYPE: PRT
<213> ORGANISM: Human immunodeficiency virus type 1

<400> SEQUENCE: 145

Pro Leu Thr Phe Gly Trp Cys Phe Lys Leu
                1               5                   10

<210> SEQ ID NO 146
<211> LENGTH: 10
<212> TYPE: PRT
<213> ORGANISM: Human immunodeficiency virus type 1

<400> SEQUENCE: 146

Val Leu Gln Trp Arg Phe Asp Ser Arg Leu
                1               5                   10

<210> SEQ ID NO 147
<211> LENGTH: 9
<212> TYPE: PRT
<213> ORGANISM: Human immunodeficiency virus type 1

<400> SEQUENCE: 147

Ala Leu His His Val Ala Arg Glu Leu
                1               5

<210> SEQ ID NO 148
<211> LENGTH: 9
<212> TYPE: PRT
<213> ORGANISM: Human immunodeficiency virus type 1

<400> SEQUENCE: 148

Ser Leu Leu Asn Ala Thr Val Asp Ile
                1               5

<210> SEQ ID NO 149
<211> LENGTH: 9
<212> TYPE: PRT
<213> ORGANISM: Human immunodeficiency virus type 1

<400> SEQUENCE: 149

Asp Leu Asn Thr Met Leu Asn Thr Val
                1               5
```

```
<210> SEQ ID NO 150
<211> LENGTH: 9
<212> TYPE: PRT
<213> ORGANISM: Human immunodeficiency virus type 1

<400> SEQUENCE: 150

Val Ile Tyr Gln Tyr Met Asp Asp Leu
 1               5

<210> SEQ ID NO 151
<211> LENGTH: 10
<212> TYPE: PRT
<213> ORGANISM: Human immunodeficiency virus type 1

<400> SEQUENCE: 151

Val Leu Val Gly Pro Thr Pro Val Asn Ile
 1               5                  10

<210> SEQ ID NO 152
<211> LENGTH: 9
<212> TYPE: PRT
<213> ORGANISM: Human immunodeficiency virus type 1

<400> SEQUENCE: 152

Pro Leu Val Lys Leu Trp Tyr Gln Leu
 1               5

<210> SEQ ID NO 153
<211> LENGTH: 8
<212> TYPE: PRT
<213> ORGANISM: Human immunodeficiency virus type 1

<400> SEQUENCE: 153

Thr Val Tyr Tyr Gly Val Pro Val
 1               5

<210> SEQ ID NO 154
<211> LENGTH: 8
<212> TYPE: PRT
<213> ORGANISM: Human immunodeficiency virus type 1

<400> SEQUENCE: 154

Ser Leu Lys Pro Cys Val Lys Leu
 1               5

<210> SEQ ID NO 155
<211> LENGTH: 9
<212> TYPE: PRT
<213> ORGANISM: Human immunodeficiency virus type 1

<400> SEQUENCE: 155

Arg Ile Gln Arg Gly Pro Gly Arg Ala
 1               5

<210> SEQ ID NO 156
<211> LENGTH: 9
<212> TYPE: PRT
<213> ORGANISM: Human immunodeficiency virus type 1

<400> SEQUENCE: 156

Thr Leu Thr Ser Cys Asn Thr Ser Val
 1               5

<210> SEQ ID NO 157
```

```
<211> LENGTH: 8
<212> TYPE: PRT
<213> ORGANISM: Human immunodeficiency virus type 1

<400> SEQUENCE: 157

Phe Ile Asn Met Trp Gln Glu Val
 1               5

<210> SEQ ID NO 158
<211> LENGTH: 9
<212> TYPE: PRT
<213> ORGANISM: Human immunodeficiency virus type 1

<400> SEQUENCE: 158

Val Val Gln Gly Ala Tyr Arg Ala Ile
 1               5

<210> SEQ ID NO 159
<211> LENGTH: 10
<212> TYPE: PRT
<213> ORGANISM: Human immunodeficiency virus type 1

<400> SEQUENCE: 159

His Ala Gly Pro Ile Ala Pro Gly Gln Met
 1               5                   10

<210> SEQ ID NO 160
<211> LENGTH: 10
<212> TYPE: PRT
<213> ORGANISM: Human immunodeficiency virus type 1

<400> SEQUENCE: 160

Gln Met Lys Asp Cys Thr Glu Arg Gln Ala
 1               5                   10

<210> SEQ ID NO 161
<211> LENGTH: 9
<212> TYPE: PRT
<213> ORGANISM: Human immunodeficiency virus type 1

<400> SEQUENCE: 161

Phe Leu Gln Ser Arg Pro Glu Thr Ala
 1               5

<210> SEQ ID NO 162
<211> LENGTH: 11
<212> TYPE: PRT
<213> ORGANISM: Human immunodeficiency virus type 1

<400> SEQUENCE: 162

Glu Ser Glu Leu Val Asn Gln Ile Ile Glu Gly
 1               5                   10

<210> SEQ ID NO 163
<211> LENGTH: 9
<212> TYPE: PRT
<213> ORGANISM: Human immunodeficiency virus type 1

<400> SEQUENCE: 163

Lys Ile Arg Leu Arg Pro Gly Gly Lys
 1               5

<210> SEQ ID NO 164
<211> LENGTH: 9
<212> TYPE: PRT
```

<213> ORGANISM: Human immunodeficiency virus type 1

<400> SEQUENCE: 164

Arg Leu Arg Pro Gly Gly Lys Lys Lys
 1 5

<210> SEQ ID NO 165
<211> LENGTH: 11
<212> TYPE: PRT
<213> ORGANISM: Human immunodeficiency virus type 1

<400> SEQUENCE: 165

Ala Leu Val Glu Ile Cys Thr Glu Met Glu Lys
1 5 10

<210> SEQ ID NO 166
<211> LENGTH: 9
<212> TYPE: PRT
<213> ORGANISM: Human immunodeficiency virus type 1

<400> SEQUENCE: 166

Ala Ile Phe Gln Ser Ser Met Thr Lys
1 5

<210> SEQ ID NO 167
<211> LENGTH: 10
<212> TYPE: PRT
<213> ORGANISM: Human immunodeficiency virus type 1

<400> SEQUENCE: 167

Asp Leu Glu Ile Gly Gln His Arg Thr Lys
1 5 10

<210> SEQ ID NO 168
<211> LENGTH: 10
<212> TYPE: PRT
<213> ORGANISM: Human immunodeficiency virus type 1

<400> SEQUENCE: 168

Gln Val Pro Leu Arg Pro Met Thr Tyr Lys
1 5 10

<210> SEQ ID NO 169
<211> LENGTH: 10
<212> TYPE: PRT
<213> ORGANISM: Human immunodeficiency virus type 1

<400> SEQUENCE: 169

Thr Val Tyr Tyr Gly Val Pro Val Trp Lys
1 5 10

<210> SEQ ID NO 170
<211> LENGTH: 11
<212> TYPE: PRT
<213> ORGANISM: Human immunodeficiency virus type 1

<400> SEQUENCE: 170

Arg Leu Arg Asp Leu Leu Leu Ile Val Thr Arg
1 5 10

<210> SEQ ID NO 171
<211> LENGTH: 9
<212> TYPE: PRT
<213> ORGANISM: Human immunodeficiency virus type 1

<400> SEQUENCE: 171

Lys Ile Arg Leu Arg Pro Gly Gly Lys
 1               5

<210> SEQ ID NO 172
<211> LENGTH: 9
<212> TYPE: PRT
<213> ORGANISM: Human immunodeficiency virus type 1

<400> SEQUENCE: 172

Ala Ile Phe Gln Ser Ser Met Thr Lys
 1               5

<210> SEQ ID NO 173
<211> LENGTH: 11
<212> TYPE: PRT
<213> ORGANISM: Human immunodeficiency virus type 1

<400> SEQUENCE: 173

Gln Ile Tyr Gln Glu Pro Phe Lys Asn Leu Lys
 1               5                  10

<210> SEQ ID NO 174
<211> LENGTH: 10
<212> TYPE: PRT
<213> ORGANISM: Human immunodeficiency virus type 1

<400> SEQUENCE: 174

Gln Val Pro Leu Arg Pro Met Thr Tyr Lys
 1               5                  10

<210> SEQ ID NO 175
<211> LENGTH: 9
<212> TYPE: PRT
<213> ORGANISM: Human immunodeficiency virus type 1

<400> SEQUENCE: 175

Ala Val Asp Leu Ser His Phe Leu Lys
 1               5

<210> SEQ ID NO 176
<211> LENGTH: 10
<212> TYPE: PRT
<213> ORGANISM: Human immunodeficiency virus type 1

<400> SEQUENCE: 176

Ala Cys Gln Val Gly Gly Pro Gly His Lys
 1               5                  10

<210> SEQ ID NO 177
<211> LENGTH: 9
<212> TYPE: PRT
<213> ORGANISM: Human immunodeficiency virus type 1

<400> SEQUENCE: 177

Ala Thr Leu Tyr Cys Val His Gln Arg
 1               5

<210> SEQ ID NO 178
<211> LENGTH: 10
<212> TYPE: PRT
<213> ORGANISM: Human immunodeficiency virus type 1

<400> SEQUENCE: 178

-continued

```
Leu Phe Cys Ala Ser Asp Ala Lys Ala Tyr
 1               5                  10

<210> SEQ ID NO 179
<211> LENGTH: 9
<212> TYPE: PRT
<213> ORGANISM: Human immunodeficiency virus type 1

<400> SEQUENCE: 179

Arg Tyr Leu Lys Asp Gln Gln Leu Leu
 1               5

<210> SEQ ID NO 180
<211> LENGTH: 8
<212> TYPE: PRT
<213> ORGANISM: Human immunodeficiency virus type 1

<400> SEQUENCE: 180

Tyr Leu Lys Asp Gln Gln Leu Leu
 1               5

<210> SEQ ID NO 181
<211> LENGTH: 9
<212> TYPE: PRT
<213> ORGANISM: Human immunodeficiency virus type 1

<400> SEQUENCE: 181

Val Tyr Tyr Asp Pro Ser Lys Asp Leu
 1               5

<210> SEQ ID NO 182
<211> LENGTH: 9
<212> TYPE: PRT
<213> ORGANISM: Human immunodeficiency virus type 1

<400> SEQUENCE: 182

Ile Tyr Gln Glu Pro Phe Lys Asn Leu
 1               5

<210> SEQ ID NO 183
<211> LENGTH: 11
<212> TYPE: PRT
<213> ORGANISM: Human immunodeficiency virus type 1

<400> SEQUENCE: 183

Glu Ser Glu Leu Val Asn Gln Ile Ile Glu Gly
 1               5                  10

<210> SEQ ID NO 184
<211> LENGTH: 10
<212> TYPE: PRT
<213> ORGANISM: Human immunodeficiency virus type 1

<400> SEQUENCE: 184

Glu Thr Ile Asn Glu Glu Ala Ala Glu Trp
 1               5                  10

<210> SEQ ID NO 185
<211> LENGTH: 9
<212> TYPE: PRT
<213> ORGANISM: Human immunodeficiency virus type 1

<400> SEQUENCE: 185

Glu Val Ile Pro Met Phe Ser Ala Leu
 1               5
```

```
<210> SEQ ID NO 186
<211> LENGTH: 9
<212> TYPE: PRT
<213> ORGANISM: Human immunodeficiency virus type 1

<400> SEQUENCE: 186

Arg Ala Ile Arg His Ile Pro Arg Arg
 1               5

<210> SEQ ID NO 187
<211> LENGTH: 11
<212> TYPE: PRT
<213> ORGANISM: Human immunodeficiency virus type 1

<400> SEQUENCE: 187

Arg Leu Arg Asp Leu Leu Leu Ile Val Thr Arg
 1               5                  10

<210> SEQ ID NO 188
<211> LENGTH: 9
<212> TYPE: PRT
<213> ORGANISM: Human immunodeficiency virus type 1

<400> SEQUENCE: 188

Arg Ile Lys Gln Ile Ile Asn Met Trp
 1               5

<210> SEQ ID NO 189
<211> LENGTH: 9
<212> TYPE: PRT
<213> ORGANISM: Human immunodeficiency virus type 1

<400> SEQUENCE: 189

His Arg Leu Arg Asp Leu Leu Leu Ile
 1               5

<210> SEQ ID NO 190
<211> LENGTH: 10
<212> TYPE: PRT
<213> ORGANISM: Human immunodeficiency virus type 1

<400> SEQUENCE: 190

Pro Ile Gln Lys Glu Thr Trp Glu Thr Trp
 1               5                  10

<210> SEQ ID NO 191
<211> LENGTH: 10
<212> TYPE: PRT
<213> ORGANISM: Human immunodeficiency virus type 1

<400> SEQUENCE: 191

Ile Ile Leu Gly Leu Asn Lys Ile Val Arg
 1               5                  10

<210> SEQ ID NO 192
<211> LENGTH: 9
<212> TYPE: PRT
<213> ORGANISM: Human immunodeficiency virus type 1

<400> SEQUENCE: 192

Tyr Leu Ala Trp Val Pro Ala His Lys
 1               5
```

```
<210> SEQ ID NO 193
<211> LENGTH: 10
<212> TYPE: PRT
<213> ORGANISM: Human immunodeficiency virus type 1

<400> SEQUENCE: 193

Thr Pro Gly Pro Gly Val Arg Tyr Pro Leu
 1               5                  10

<210> SEQ ID NO 194
<211> LENGTH: 9
<212> TYPE: PRT
<213> ORGANISM: Human immunodeficiency virus type 1

<400> SEQUENCE: 194

Phe Pro Val Thr Gln Val Pro Leu Arg
 1               5

<210> SEQ ID NO 195
<211> LENGTH: 10
<212> TYPE: PRT
<213> ORGANISM: Human immunodeficiency virus type 1

<400> SEQUENCE: 195

Arg Pro Asn Asn Asn Thr Arg Lys Ser Ile
 1               5                  10

<210> SEQ ID NO 196
<211> LENGTH: 9
<212> TYPE: PRT
<213> ORGANISM: Human immunodeficiency virus type 1

<400> SEQUENCE: 196

Ile Pro Arg Arg Ile Arg Gln Gly Leu
 1               5

<210> SEQ ID NO 197
<211> LENGTH: 9
<212> TYPE: PRT
<213> ORGANISM: Human immunodeficiency virus type 1

<400> SEQUENCE: 197

Tyr Leu Ala Trp Val Pro Ala His Lys
 1               5

<210> SEQ ID NO 198
<211> LENGTH: 9
<212> TYPE: PRT
<213> ORGANISM: Human immunodeficiency virus type 1

<400> SEQUENCE: 198

Arg Val Lys Glu Lys Tyr Gln His Leu
 1               5

<210> SEQ ID NO 199
<211> LENGTH: 9
<212> TYPE: PRT
<213> ORGANISM: Human immunodeficiency virus type 1

<400> SEQUENCE: 199

Gly Gly Lys Lys Lys Tyr Lys Leu Lys
 1               5

<210> SEQ ID NO 200
<211> LENGTH: 8
```

<212> TYPE: PRT
<213> ORGANISM: Human immunodeficiency virus type 1

<400> SEQUENCE: 200

Phe Leu Lys Glu Lys Gly Gly Leu
 1               5

<210> SEQ ID NO 201
<211> LENGTH: 9
<212> TYPE: PRT
<213> ORGANISM: Human immunodeficiency virus type 1

<400> SEQUENCE: 201

Gly Glu Ile Tyr Lys Arg Trp Ile Ile
 1               5

<210> SEQ ID NO 202
<211> LENGTH: 8
<212> TYPE: PRT
<213> ORGANISM: Human immunodeficiency virus type 1

<400> SEQUENCE: 202

Tyr Leu Lys Asp Gln Gln Leu Leu
 1               5

<210> SEQ ID NO 203
<211> LENGTH: 8
<212> TYPE: PRT
<213> ORGANISM: Human immunodeficiency virus type 1

<400> SEQUENCE: 203

Pro Arg Arg Ile Arg Gln Gly Leu
 1               5

<210> SEQ ID NO 204
<211> LENGTH: 10
<212> TYPE: PRT
<213> ORGANISM: Human immunodeficiency virus type 1

<400> SEQUENCE: 204

Arg Ile Arg Gln Gly Leu Glu Arg Ile Leu
 1               5                  10

<210> SEQ ID NO 205
<211> LENGTH: 9
<212> TYPE: PRT
<213> ORGANISM: Human immunodeficiency virus type 1

<400> SEQUENCE: 205

Asp Cys Lys Thr Ile Leu Lys Ala Leu
 1               5

<210> SEQ ID NO 206
<211> LENGTH: 9
<212> TYPE: PRT
<213> ORGANISM: Human immunodeficiency virus type 1

<400> SEQUENCE: 206

Gly Pro Lys Val Lys Gln Trp Pro Leu
 1               5

<210> SEQ ID NO 207
<211> LENGTH: 8
<212> TYPE: PRT
<213> ORGANISM: Human immunodeficiency virus type 1

<400> SEQUENCE: 207

Glu Trp Arg Phe Asp Ser Arg Leu
 1               5

<210> SEQ ID NO 208
<211> LENGTH: 9
<212> TYPE: PRT
<213> ORGANISM: Human immunodeficiency virus type 1

<400> SEQUENCE: 208

Glu Arg Tyr Leu Lys Asp Gln Gln Leu
 1               5

<210> SEQ ID NO 209
<211> LENGTH: 9
<212> TYPE: PRT
<213> ORGANISM: Human immunodeficiency virus type 1

<400> SEQUENCE: 209

Asp Leu Asn Thr Met Leu Asn Thr Val
 1               5

<210> SEQ ID NO 210
<211> LENGTH: 9
<212> TYPE: PRT
<213> ORGANISM: Human immunodeficiency virus type 1

<400> SEQUENCE: 210

Asp Arg Phe Tyr Lys Thr Leu Arg Ala
 1               5

<210> SEQ ID NO 211
<211> LENGTH: 11
<212> TYPE: PRT
<213> ORGANISM: Human immunodeficiency virus type 1

<400> SEQUENCE: 211

Leu Arg Ala Glu Gln Ala Ser Val Gln Glu Val
 1               5                  10

<210> SEQ ID NO 212
<211> LENGTH: 10
<212> TYPE: PRT
<213> ORGANISM: Human immunodeficiency virus type 1

<400> SEQUENCE: 212

Arg Ala Glu Gln Ala Ser Val Gln Glu Val
 1               5                  10

<210> SEQ ID NO 213
<211> LENGTH: 9
<212> TYPE: PRT
<213> ORGANISM: Human immunodeficiency virus type 1

<400> SEQUENCE: 213

Tyr Pro Leu Thr Phe Gly Trp Cys Tyr
 1               5

<210> SEQ ID NO 214
<211> LENGTH: 9
<212> TYPE: PRT
<213> ORGANISM: Human immunodeficiency virus type 1

<400> SEQUENCE: 214

```
Tyr Pro Leu Thr Phe Gly Trp Cys Phe
 1               5
```

<210> SEQ ID NO 215
<211> LENGTH: 10
<212> TYPE: PRT
<213> ORGANISM: Human immunodeficiency virus type 1

<400> SEQUENCE: 215

```
Gln Val Pro Leu Arg Pro Met Thr Tyr Lys
 1               5                   10
```

<210> SEQ ID NO 216
<211> LENGTH: 7
<212> TYPE: PRT
<213> ORGANISM: Human immunodeficiency virus type 1

<400> SEQUENCE: 216

```
Tyr Pro Leu Thr Phe Gly Trp
 1               5
```

<210> SEQ ID NO 217
<211> LENGTH: 9
<212> TYPE: PRT
<213> ORGANISM: Human immunodeficiency virus type 1

<400> SEQUENCE: 217

```
Glu Arg Tyr Leu Lys Asp Gln Gln Leu
 1               5
```

<210> SEQ ID NO 218
<211> LENGTH: 10
<212> TYPE: PRT
<213> ORGANISM: Human immunodeficiency virus type 1

<400> SEQUENCE: 218

```
Gly Arg Arg Gly Trp Glu Ala Leu Lys Tyr
 1               5                   10
```

<210> SEQ ID NO 219
<211> LENGTH: 9
<212> TYPE: PRT
<213> ORGANISM: Human immunodeficiency virus type 1

<400> SEQUENCE: 219

```
Asp Pro Asn Pro Gln Glu Val Val Leu
 1               5
```

<210> SEQ ID NO 220
<211> LENGTH: 9
<212> TYPE: PRT
<213> ORGANISM: Human immunodeficiency virus type 1

<400> SEQUENCE: 220

```
Arg Pro Val Val Ser Thr Gln Leu Leu
 1               5
```

<210> SEQ ID NO 221
<211> LENGTH: 10
<212> TYPE: PRT
<213> ORGANISM: Human immunodeficiency virus type 1

<400> SEQUENCE: 221

```
Val Pro Leu Asp Lys Asp Phe Arg Lys Tyr
```

-continued

```
                1               5                  10
```

<210> SEQ ID NO 222
<211> LENGTH: 9
<212> TYPE: PRT
<213> ORGANISM: Human immunodeficiency virus type 1

<400> SEQUENCE: 222

```
Ser Pro Ala Ile Phe Gln Ser Ser Met
 1               5
```

<210> SEQ ID NO 223
<211> LENGTH: 9
<212> TYPE: PRT
<213> ORGANISM: Human immunodeficiency virus type 1

<400> SEQUENCE: 223

```
Asn Pro Asp Ile Val Thr Tyr Gln Tyr
 1               5
```

<210> SEQ ID NO 224
<211> LENGTH: 9
<212> TYPE: PRT
<213> ORGANISM: Human immunodeficiency virus type 1

<400> SEQUENCE: 224

```
Ile Pro Leu Thr Glu Glu Ala Glu Leu
 1               5
```

<210> SEQ ID NO 225
<211> LENGTH: 10
<212> TYPE: PRT
<213> ORGANISM: Human immunodeficiency virus type 1

<400> SEQUENCE: 225

```
Glu Pro Ile Val Gly Ala Glu Thr Phe Tyr
 1               5                  10
```

<210> SEQ ID NO 226
<211> LENGTH: 9
<212> TYPE: PRT
<213> ORGANISM: Human immunodeficiency virus type 1

<400> SEQUENCE: 226

```
Phe Pro Val Arg Pro Gln Val Pro Leu
 1               5
```

<210> SEQ ID NO 227
<211> LENGTH: 9
<212> TYPE: PRT
<213> ORGANISM: Human immunodeficiency virus type 1

<400> SEQUENCE: 227

```
Thr Ala Val Pro Trp Asn Ala Ser Trp
 1               5
```

<210> SEQ ID NO 228
<211> LENGTH: 11
<212> TYPE: PRT
<213> ORGANISM: Human immunodeficiency virus type 1

<400> SEQUENCE: 228

```
Val Pro Val Trp Lys Glu Ala Thr Thr Thr Leu
 1               5                  10
```

-continued

<210> SEQ ID NO 229
<211> LENGTH: 9
<212> TYPE: PRT
<213> ORGANISM: Human immunodeficiency virus type 1

<400> SEQUENCE: 229

Asn Ser Ser Gln Val Ser Gln Asn Tyr
 1               5

<210> SEQ ID NO 230
<211> LENGTH: 9
<212> TYPE: PRT
<213> ORGANISM: Human immunodeficiency virus type 1

<400> SEQUENCE: 230

Ser Glu Gly Ala Thr Pro Gln Asp Leu
 1               5

<210> SEQ ID NO 231
<211> LENGTH: 10
<212> TYPE: PRT
<213> ORGANISM: Human immunodeficiency virus type 1

<400> SEQUENCE: 231

Leu Glu Ser Gly Ala Thr Pro Gln Asp Leu
 1               5                   10

<210> SEQ ID NO 232
<211> LENGTH: 9
<212> TYPE: PRT
<213> ORGANISM: Human immunodeficiency virus type 1

<400> SEQUENCE: 232

Arg Ala Ile Glu Ala Gln Gln His Leu
 1               5

<210> SEQ ID NO 233
<211> LENGTH: 9
<212> TYPE: PRT
<213> ORGANISM: Human immunodeficiency virus type 1

<400> SEQUENCE: 233

Ala Leu Val Glu Ile Cys Thr Glu Met
 1               5

<210> SEQ ID NO 234
<211> LENGTH: 9
<212> TYPE: PRT
<213> ORGANISM: Human immunodeficiency virus type 1

<400> SEQUENCE: 234

Glu Lys Glu Gly Lys Ile Ser Lys Ile
 1               5

<210> SEQ ID NO 235
<211> LENGTH: 8
<212> TYPE: PRT
<213> ORGANISM: Human immunodeficiency virus type 1

<400> SEQUENCE: 235

Thr Ala Phe Thr Ile Pro Ser Ile
 1               5

<210> SEQ ID NO 236

```
<211> LENGTH: 10
<212> TYPE: PRT
<213> ORGANISM: Human immunodeficiency virus type 1

<400> SEQUENCE: 236

Val Pro Val Trp Lys Glu Ala Thr Thr Thr
 1               5                  10

<210> SEQ ID NO 237
<211> LENGTH: 10
<212> TYPE: PRT
<213> ORGANISM: Human immunodeficiency virus type 1

<400> SEQUENCE: 237

Thr Ser Leu Thr Gln Glu Gln Ile Gly Trp
 1               5                  10

<210> SEQ ID NO 238
<211> LENGTH: 10
<212> TYPE: PRT
<213> ORGANISM: Human immunodeficiency virus type 1

<400> SEQUENCE: 238

His Thr Gln Gly Tyr Phe Pro Asp Trp Gln
 1               5                  10

<210> SEQ ID NO 239
<211> LENGTH: 9
<212> TYPE: PRT
<213> ORGANISM: Human immunodeficiency virus type 1

<400> SEQUENCE: 239

His Thr Gln Gly Tyr Phe Pro Asp Trp
 1               5

<210> SEQ ID NO 240
<211> LENGTH: 9
<212> TYPE: PRT
<213> ORGANISM: Human immunodeficiency virus type 1

<400> SEQUENCE: 240

Ile Ser Pro Arg Thr Leu Asn Ala Trp
 1               5

<210> SEQ ID NO 241
<211> LENGTH: 9
<212> TYPE: PRT
<213> ORGANISM: Human immunodeficiency virus type 1

<400> SEQUENCE: 241

Phe Ser Pro Glu Val Ile Pro Met Phe
 1               5

<210> SEQ ID NO 242
<211> LENGTH: 10
<212> TYPE: PRT
<213> ORGANISM: Human immunodeficiency virus type 1

<400> SEQUENCE: 242

Arg Leu Arg Pro Gly Gly Lys Lys Lys Tyr
 1               5                  10

<210> SEQ ID NO 243
<211> LENGTH: 12
<212> TYPE: PRT
```

<213> ORGANISM: Human immunodeficiency virus type 1

<400> SEQUENCE: 243

Leu Val Gly Lys Leu Asn Trp Ala Ser Gln Asn Tyr
1               5                   10

<210> SEQ ID NO 244
<211> LENGTH: 9
<212> TYPE: PRT
<213> ORGANISM: Human immunodeficiency virus type 1

<400> SEQUENCE: 244

Ser Phe Asn Cys Gly Gly Glu Phe Phe
1               5

<210> SEQ ID NO 245
<211> LENGTH: 10
<212> TYPE: PRT
<213> ORGANISM: Human immunodeficiency virus type 1

<400> SEQUENCE: 245

Val Thr Asp Ser Gln Tyr Ala Leu Gly Ile
1               5                   10

<210> SEQ ID NO 246
<211> LENGTH: 9
<212> TYPE: PRT
<213> ORGANISM: Human immunodeficiency virus type 1

<400> SEQUENCE: 246

Arg Ala Glu Gln Ala Ser Gln Glu Val
1               5

<210> SEQ ID NO 247
<211> LENGTH: 10
<212> TYPE: PRT
<213> ORGANISM: Human immunodeficiency virus type 1

<400> SEQUENCE: 247

Lys Ala Ala Leu Asp Leu Ser His Pro Leu
1               5                   10

<210> SEQ ID NO 248
<211> LENGTH: 9
<212> TYPE: PRT
<213> ORGANISM: Human immunodeficiency virus type 1

<400> SEQUENCE: 248

Gln Ala Thr Gln Glu Val Lys Asn Trp
1               5

<210> SEQ ID NO 249
<211> LENGTH: 9
<212> TYPE: PRT
<213> ORGANISM: Homo sapiens

<400> SEQUENCE: 249

Met Leu Leu Ala Val Leu Tyr Cys Leu
1               5

<210> SEQ ID NO 250
<211> LENGTH: 9
<212> TYPE: PRT
<213> ORGANISM: Homo sapiens

```
<400> SEQUENCE: 250

Tyr Met Asn Gly Thr Met Ser Gln Val
 1               5

<210> SEQ ID NO 251
<211> LENGTH: 9
<212> TYPE: PRT
<213> ORGANISM: Homo sapiens

<400> SEQUENCE: 251

Ala Phe Leu Pro Trp His Arg Leu Phe
 1               5

<210> SEQ ID NO 252
<211> LENGTH: 9
<212> TYPE: PRT
<213> ORGANISM: Homo sapiens

<400> SEQUENCE: 252

Tyr Met Asp Gly Thr Met Ser Gln Val
 1               5

<210> SEQ ID NO 253
<211> LENGTH: 9
<212> TYPE: PRT
<213> ORGANISM: Homo sapiens

<400> SEQUENCE: 253

Ser Glu Ile Trp Arg Asp Ile Asp Phe
 1               5

<210> SEQ ID NO 254
<211> LENGTH: 15
<212> TYPE: PRT
<213> ORGANISM: Homo sapiens

<400> SEQUENCE: 254

Gln Asn Ile Leu Leu Ser Asn Ala Pro Leu Gly Pro Gln Phe Pro
 1               5                  10                  15

<210> SEQ ID NO 255
<211> LENGTH: 13
<212> TYPE: PRT
<213> ORGANISM: Homo sapiens

<400> SEQUENCE: 255

Ser Tyr Leu Gln Asp Ser Asp Pro Asp Ser Phe Gln Asp
 1               5                  10

<210> SEQ ID NO 256
<211> LENGTH: 9
<212> TYPE: PRT
<213> ORGANISM: Homo sapiens

<400> SEQUENCE: 256

Lys Thr Trp Gly Gln Tyr Trp Gln Val
 1               5

<210> SEQ ID NO 257
<211> LENGTH: 10
<212> TYPE: PRT
<213> ORGANISM: Homo sapiens

<400> SEQUENCE: 257
```

Ala Met Leu Gly Thr His Thr Met Glu Val
1               5                   10

<210> SEQ ID NO 258
<211> LENGTH: 9
<212> TYPE: PRT
<213> ORGANISM: Homo sapiens

<400> SEQUENCE: 258

Met Leu Gly Thr His Thr Met Glu Val
1               5

<210> SEQ ID NO 259
<211> LENGTH: 9
<212> TYPE: PRT
<213> ORGANISM: Homo sapiens

<400> SEQUENCE: 259

Ile Thr Asp Gln Val Pro Phe Ser Val
1               5

<210> SEQ ID NO 260
<211> LENGTH: 9
<212> TYPE: PRT
<213> ORGANISM: Homo sapiens

<400> SEQUENCE: 260

Tyr Leu Glu Pro Gly Pro Val Thr Ala
1               5

<210> SEQ ID NO 261
<211> LENGTH: 10
<212> TYPE: PRT
<213> ORGANISM: Homo sapiens

<400> SEQUENCE: 261

Leu Leu Asp Gly Thr Ala Thr Leu Arg Leu
1               5                   10

<210> SEQ ID NO 262
<211> LENGTH: 10
<212> TYPE: PRT
<213> ORGANISM: Homo sapiens

<400> SEQUENCE: 262

Val Leu Tyr Arg Tyr Gly Ser Phe Ser Val
1               5                   10

<210> SEQ ID NO 263
<211> LENGTH: 10
<212> TYPE: PRT
<213> ORGANISM: Homo sapiens

<400> SEQUENCE: 263

Ser Leu Ala Asp Thr Asn Ser Leu Ala Val
1               5                   10

<210> SEQ ID NO 264
<211> LENGTH: 9
<212> TYPE: PRT
<213> ORGANISM: Homo sapiens

<400> SEQUENCE: 264

Ala Leu Leu Ala Val Gly Ala Thr Lys
1               5

<210> SEQ ID NO 265
<211> LENGTH: 9
<212> TYPE: PRT
<213> ORGANISM: Homo sapiens

<400> SEQUENCE: 265

Ala Ala Gly Ile Gly Ile Leu Thr Val
 1               5

<210> SEQ ID NO 266
<211> LENGTH: 10
<212> TYPE: PRT
<213> ORGANISM: Homo sapiens

<400> SEQUENCE: 266

Glu Ala Ala Gly Ile Gly Ile Leu Thr Val
 1               5                  10

<210> SEQ ID NO 267
<211> LENGTH: 9
<212> TYPE: PRT
<213> ORGANISM: Homo sapiens

<400> SEQUENCE: 267

Ile Leu Thr Val Ile Leu Gly Val Leu
 1               5

<210> SEQ ID NO 268
<211> LENGTH: 9
<212> TYPE: PRT
<213> ORGANISM: Homo sapiens

<400> SEQUENCE: 268

Met Ser Leu Gln Arg Gln Phe Leu Arg
 1               5

<210> SEQ ID NO 269
<211> LENGTH: 9
<212> TYPE: PRT
<213> ORGANISM: Homo sapiens

<400> SEQUENCE: 269

Leu Leu Gly Pro Gly Arg Pro Tyr Arg
 1               5

<210> SEQ ID NO 270
<211> LENGTH: 9
<212> TYPE: PRT
<213> ORGANISM: Homo sapiens

<400> SEQUENCE: 270

Glu Glu Lys Leu Ile Val Val Leu Phe
 1               5

<210> SEQ ID NO 271
<211> LENGTH: 10
<212> TYPE: PRT
<213> ORGANISM: Homo sapiens

<400> SEQUENCE: 271

Ala Cys Asp Pro His Ser Gly His Phe Val
 1               5                  10

```
<210> SEQ ID NO 272
<211> LENGTH: 9
<212> TYPE: PRT
<213> ORGANISM: Homo sapiens

<400> SEQUENCE: 272

Ser Tyr Leu Asp Ser Gly Ile His Phe
 1               5

<210> SEQ ID NO 273
<211> LENGTH: 9
<212> TYPE: PRT
<213> ORGANISM: Homo sapiens

<400> SEQUENCE: 273

Phe Pro Ser Asp Ser Trp Cys Tyr Phe
 1               5

<210> SEQ ID NO 274
<211> LENGTH: 9
<212> TYPE: PRT
<213> ORGANISM: Homo sapiens

<400> SEQUENCE: 274

Glu Ala Asp Pro Thr Gly His Ser Tyr
 1               5

<210> SEQ ID NO 275
<211> LENGTH: 9
<212> TYPE: PRT
<213> ORGANISM: Homo sapiens

<400> SEQUENCE: 275

Ser Ala Tyr Gly Glu Pro Arg Lys Leu
 1               5

<210> SEQ ID NO 276
<211> LENGTH: 9
<212> TYPE: PRT
<213> ORGANISM: Homo sapiens

<400> SEQUENCE: 276

Glu Val Asp Pro Ile Gly His Leu Tyr
 1               5

<210> SEQ ID NO 277
<211> LENGTH: 9
<212> TYPE: PRT
<213> ORGANISM: Homo sapiens

<400> SEQUENCE: 277

Phe Leu Trp Gly Pro Arg Ala Leu Val
 1               5

<210> SEQ ID NO 278
<211> LENGTH: 10
<212> TYPE: PRT
<213> ORGANISM: Homo sapiens

<400> SEQUENCE: 278

Met Glu Val Asp Pro Ile Gly His Leu Tyr
 1               5                  10

<210> SEQ ID NO 279
<211> LENGTH: 9
```

```
<212> TYPE: PRT
<213> ORGANISM: Homo sapiens

<400> SEQUENCE: 279

Ala Ala Arg Ala Val Phe Leu Ala Leu
  1               5

<210> SEQ ID NO 280
<211> LENGTH: 8
<212> TYPE: PRT
<213> ORGANISM: Homo sapiens

<400> SEQUENCE: 280

Tyr Arg Pro Arg Pro Arg Arg Tyr
  1               5

<210> SEQ ID NO 281
<211> LENGTH: 10
<212> TYPE: PRT
<213> ORGANISM: Homo sapiens

<400> SEQUENCE: 281

Ser Pro Ser Ser Asn Arg Ile Arg Asn Thr
  1               5                  10

<210> SEQ ID NO 282
<211> LENGTH: 9
<212> TYPE: PRT
<213> ORGANISM: Homo sapiens

<400> SEQUENCE: 282

Val Leu Pro Asp Val Phe Ile Arg Cys
  1               5

<210> SEQ ID NO 283
<211> LENGTH: 20
<212> TYPE: PRT
<213> ORGANISM: Homo sapiens

<400> SEQUENCE: 283

Pro Asp Thr Arg Pro Ala Pro Gly Ser Thr Ala Pro Pro Ala His Gly
  1               5                  10                  15

Val Thr Ser Ala
             20

<210> SEQ ID NO 284
<211> LENGTH: 14
<212> TYPE: PRT
<213> ORGANISM: Human papillomavirus

<400> SEQUENCE: 284

Gly Gln Ala Glu Pro Asp Arg Ala His Asn Ile Val Thr Phe
  1               5                  10

<210> SEQ ID NO 285
<211> LENGTH: 9
<212> TYPE: PRT
<213> ORGANISM: Epstein-Barr virus

<400> SEQUENCE: 285

Ile Val Thr Asp Phe Ser Val Ile Lys
  1               5
```